(12) United States Patent
Enomura

(10) Patent No.: US 8,992,981 B2
(45) Date of Patent: Mar. 31, 2015

(54) METHOD FOR PRODUCING MICROPARTICLES AND THE MICROPARTICLES

(75) Inventor: Masakazu Enomura, Izumi (JP)

(73) Assignee: M Technique Co., Ltd., Osaka (JP)

( * ) Notice: Subject to any disclaimer, the term of this patent is extended or adjusted under 35 U.S.C. 154(b) by 965 days.

(21) Appl. No.: 12/679,172

(22) PCT Filed: Sep. 11, 2008

(86) PCT No.: PCT/JP2008/066386
§ 371 (c)(1),
(2), (4) Date: Apr. 14, 2010

(87) PCT Pub. No.: WO2009/038008
PCT Pub. Date: Mar. 26, 2009

(65) Prior Publication Data
US 2010/0215958 A1    Aug. 26, 2010

(30) Foreign Application Priority Data

Sep. 21, 2007   (JP) .................................. 2007-244568

(51) Int. Cl.
| | |
|---|---|
| *A61K 9/14* | (2006.01) |
| *B01D 9/00* | (2006.01) |
| *A61K 9/50* | (2006.01) |
| *B01J 19/10* | (2006.01) |
| *B01J 19/12* | (2006.01) |
| *B01J 19/18* | (2006.01) |

(52) U.S. Cl.
CPC .............. *B01D 9/0013* (2013.01); *A61K 9/146* (2013.01); *A61K 9/5089* (2013.01); *B01D 9/0031* (2013.01); *B01D 9/0081* (2013.01); *B01J 19/10* (2013.01); *B01J 19/123* (2013.01); *B01J 19/1887* (2013.01); *B01J 2219/00094* (2013.01); *B01J 2219/00137* (2013.01)
USPC ......................................................... 424/489

(58) Field of Classification Search
CPC ............................................... B01F 2003/0846
USPC ......................................................... 424/489
See application file for complete search history.

(56) References Cited

U.S. PATENT DOCUMENTS

| | | | |
|---|---|---|---|
| 2004/0032792 A1 | 2/2004 | Enomura | |
| 2004/0152663 A1* | 8/2004 | Byun et al. ..................... | 514/56 |
| 2004/0230000 A1* | 11/2004 | Misumi et al. ................ | 525/128 |
| 2004/0241430 A1 | 12/2004 | Jachuck et al. | |
| 2006/0024379 A1* | 2/2006 | Brown et al. ................. | 424/490 |
| 2006/0266847 A1 | 11/2006 | Enomura | |

FOREIGN PATENT DOCUMENTS

| | | |
|---|---|---|
| EP | 2179791 A1 | 4/2010 |
| EP | 2180021 A1 | 4/2010 |

(Continued)

*Primary Examiner* — Benjamin Packard
(74) *Attorney, Agent, or Firm* — Birch, Stewart, Kolasch & Birch, LLP

(57) ABSTRACT

It is an object of the present invention to provide a method for producing microparticles, which can produce monodispersed microparticles, causes no clogging with a product due to self-dischargeability, requires no great pressure, and is excellent in productivity, wherein a fluid in which at least one kind of microparticle materials is dissolved is introduced between two processing surfaces arranged to be opposite to each other to be able to approach to and separate from each other, at least one of which rotates relative to the other, to be formed into a thin film fluid, and the thin film fluid is cooled or heated (warmed) to allow saturation solubility to change, thereby separating microparticles.

20 Claims, 29 Drawing Sheets

(56) References Cited

FOREIGN PATENT DOCUMENTS

| | | | |
|---|---|---|---|
| JP | 2004-49957 A | 2/2004 | |
| JP | 2004-534649 A | 11/2004 | |
| JP | 2005-313102 A | 11/2005 | |
| WO | WO 00/48730 A2 | 8/2000 | |
| WO | WO 2009/008388 A1 | 1/2009 | |
| WO | WO 2009/008389 A1 | 1/2009 | |

* cited by examiner

FIG. 1A
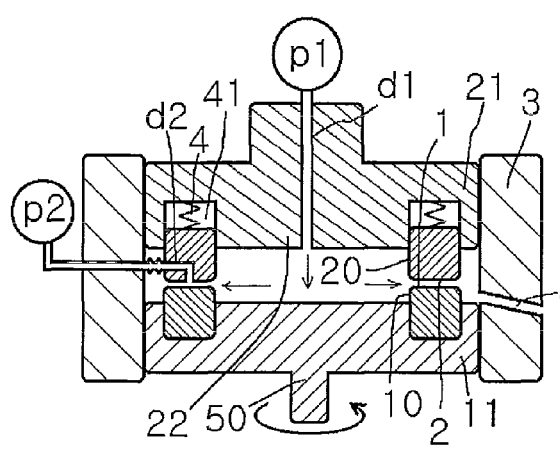
FIG. 1B
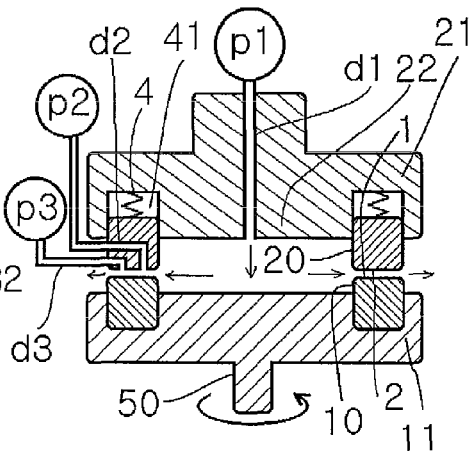
FIG. 1C
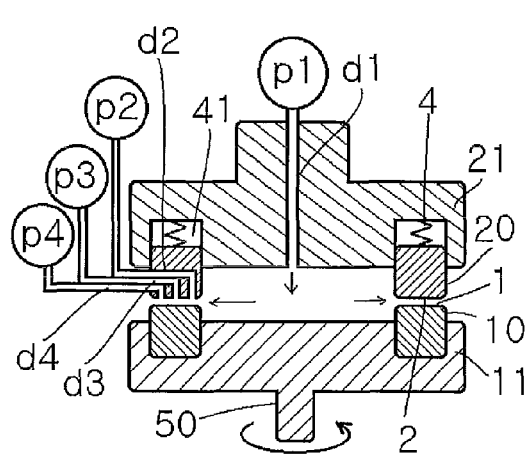
FIG. 1D

FIG. 2A
FIG. 2B
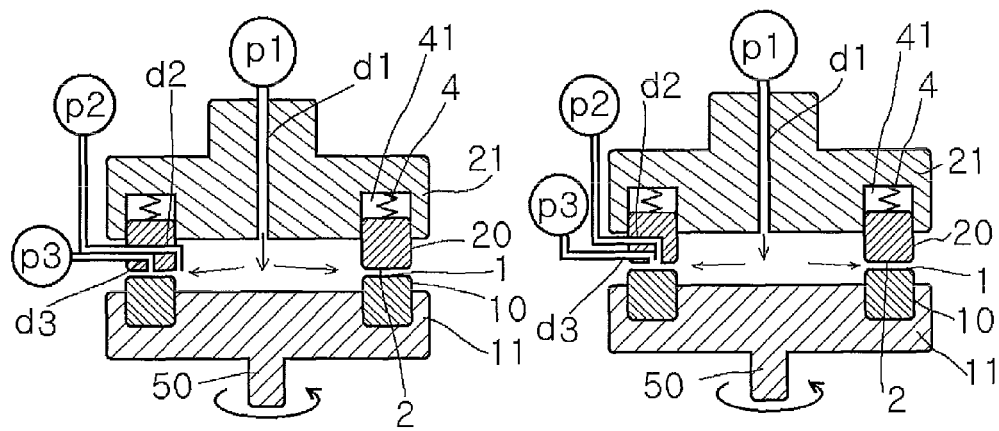
FIG. 2C
FIG. 2D
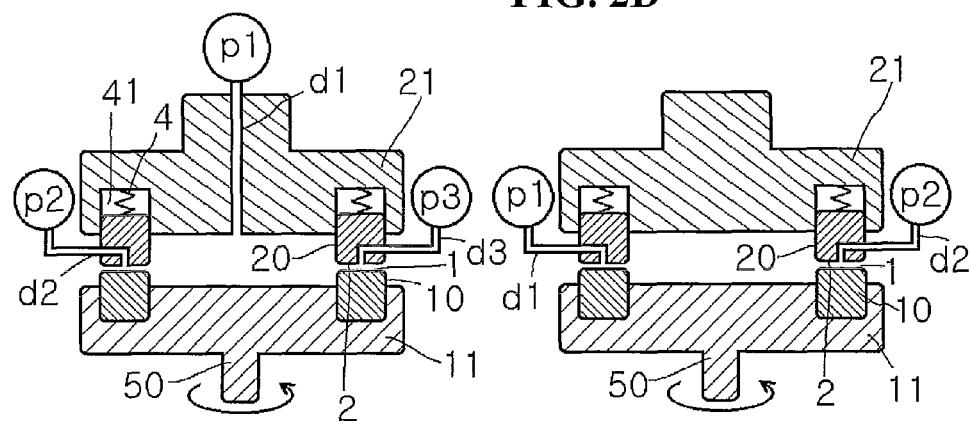

FIG. 18A
FIG. 18B
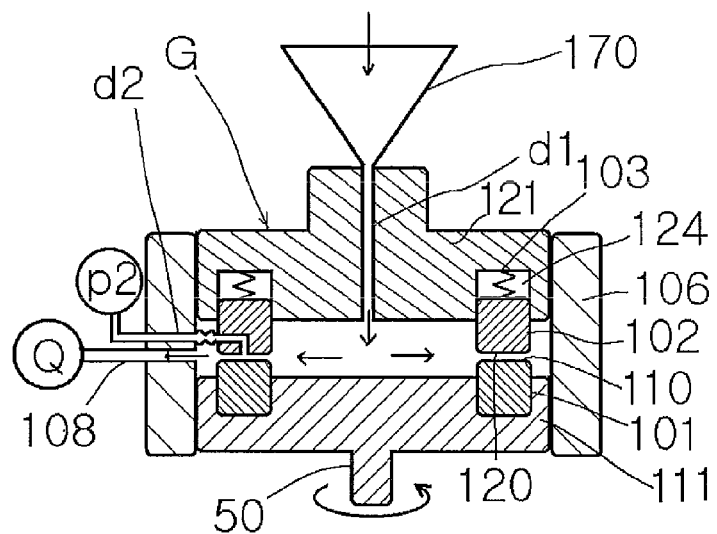
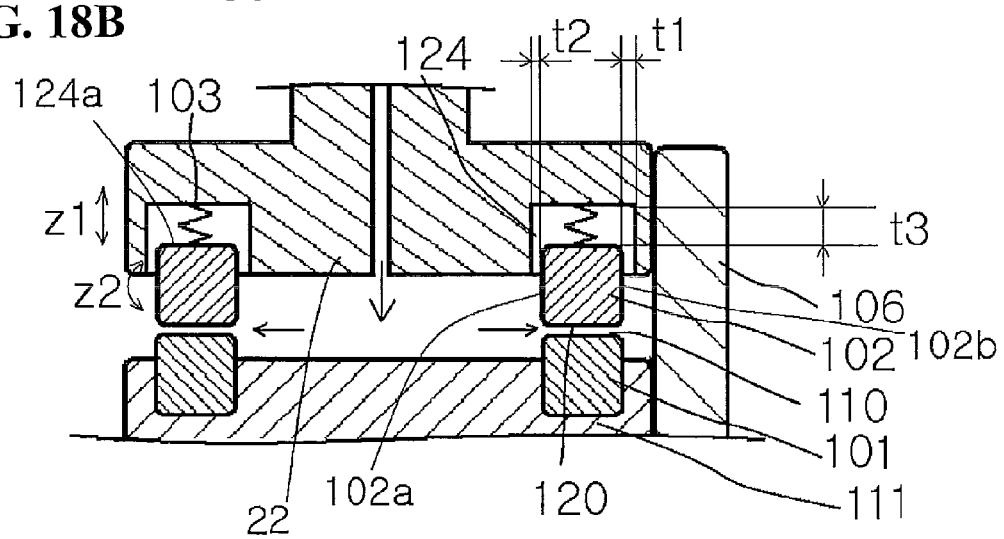

FIG. 23A
FIG. 23B
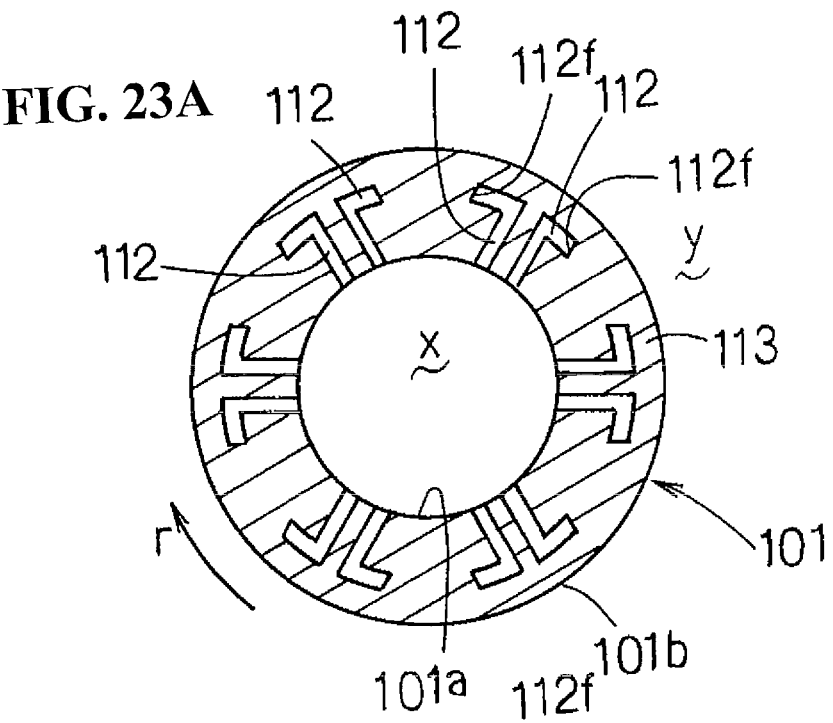
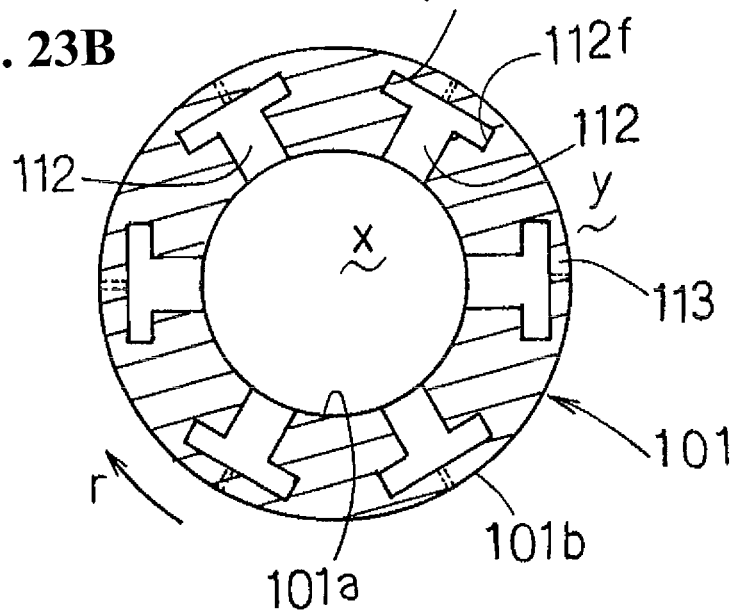

METHOD FOR PRODUCING MICROPARTICLES AND THE MICROPARTICLES

TECHNICAL FIELD

The present invention relates to a method for producing microparticles having excellent re-dispersibility, which can produce uniform microparticles and is easily capable of production with energy efficiency and capable of mass production.

BACKGROUND ART

Non-Patent Document 1: "Current Techniques of Nanomaterials" written by Mitsue Koizumi et al., first edition, CMC Publishing Co., Ltd., April, 2001
Non-Patent Document 2: "Nanotechnology Handbook, Part I, Creation", first edition, edited by Nanotechnology Handbook Editorial Committee, Ohmsha, Ltd., May, 2003
Patent Document 1: JP-A H07-144102
Patent Document 2: JP-A 2002-97281
Patent Document 3: JP-A 2007-8924

Microparticles, particularly 100 nm or less nanoparticles, have a significantly high ratio of the surface area to volume of the particle, thus bringing about new characteristics, and thus nanomaterials such as nanoparticles themselves, their aggregates or organic-inorganic complexes are highly expected as materials in the 21st century (Non-Patent Document 1). That is, conventional materials can exhibit new functions by mere microparticulation, so the nanoparticles become an important theme in the industrial world, and the advance of nanotechnology is naturally inseparable from microparticles, particularly nanoparticles (Non-Patent Document 2).

Accordingly, a new method for producing microparticles has been desired. Further, it is the most important task in nanotechnology to establish a production method capable of stable large-production in order to utilize the method in industry.

As a method of preparing microparticles in liquid, there is a method of separating microparticles wherein a solution having a specific solute dissolved therein is stirred, while the difference in solubility of the solute in the solvent caused by temperature difference is utilized, as shown in Patent Document 1. This method utilizes the phenomenon that the solubility of the solute in the solvent at a predetermined temperature is decreased by decreasing the temperature of the solvent so that the solute in an amount over saturation solubility is separated. However, since this method uses a general-purpose iron pot having a Faudora vane, preparation of nano size particles is substantially difficult, and when separation of crystals is intended, it is difficult to make their crystal form uniform. Accordingly, a method of obtaining microparticles by dissolving an organic matter in an organic solvent and then pouring the resulting organic matter solution into a solvent in which the organic matter is lower soluble in the organic solvent is becoming popular as shown in Patent Document 2 wherein a good solvent in which a solute is highly soluble is mixed with a poor solvent in which the solute is low soluble, thereby decreasing the apparent solubility of the solute in the good solvent and separating the solute over saturation solubility to obtain microparticles. However, both the two methods described above are those separating a substance in a batch reaction container and a reaction iron pot, wherein stable production of microparticles of nano size or of uniform crystal form is extremely difficult. This is because, in the case of a separating reaction in a batch system generally using stirring operation, temperature gradient or concentration gradient and its accompanying disproportionation of a reaction site inevitably occur. Accordingly, temperature control and concentration control in a batch system are extremely difficult, thus inevitably a uniform reaction difficult. As a result, there arises necessity for prolongation of the reaction time, etc., to make control of all reaction conditions very difficult.

As shown in Patent Document 3, there is a method of obtaining microparticles by utilizing solubility difference with a micromixer or a microreactor. When the general microreactor is used, there are many advantages in the microdevice and system, but as the micro-flow path diameter is decreased, pressure loss is inversely proportional to the biquadrate of the flow path; that is, an extremely high feeding pressure becomes necessary thus making a pump for actually feeding a fluid hardly available. In addition, there are many problems; for example, a phenomena of clogging of a flow path with a product occurs when the reaction is accompanied by separation, a micro-flow path is clogged with bubbles generated by a reaction, a microscopic space is not effective or applicable to every reaction although the speed of molecular diffusion is fundamentally expected for the reaction. Actually, the reaction should be attempted by trial and error in order to select good results. Scaling up has been coped with a method of increasing the number of microreactors, that is numbering up, but the number of microreactors which can be stuck is limited to several dozen, thus inherently aiming exclusively at products of high value, and the increase in the number of devices leads to an increase the absolute number of failure causes, and when the problem of clogging actually occurs, it can be very difficult to detect a problem site such as failure site.

In light of this situation, it is an object of the present invention to provide a method for producing microparticles obtained through separation of lysates by using the change of saturation solubility due to the temperature difference of fluids in a thin film fluid formed between two processing surfaces arranged opposite to each other to be able to approach to and separate from each other, at least one of which rotates relative to the other, wherein the temperature in the thin film fluid is highly uniform and the stirring in a reactor is highly uniform so that the temperature distribution and concentration distribution in the reactor is remarkably uniform, whereby monodispersed microparticles can be produced depending on its purpose, and wherein clogging with a product does not occur due to self-dischargeability, great pressure is not necessary, and productivity is high. Further, it is another object to produce microparticles at a lower energy, as compared with the conventional production methods.

DISCLOSURE OF INVENTION

An aspect of the invention according to claim 1 in the present application is a method for producing microparticles, wherein a fluid in which at least one kind of microparticle materials is dissolved is introduced between two processing surfaces arranged opposite to each other to be able to approach to and separate from each other, at least one of which rotates relative to the other, to be formed into a thin film fluid, and the thin film fluid is cooled or heated (warmed) to allow saturation solubility to change thereby separating microparticles.

An aspect of the invention according to claim 2 in the present application is a method for producing microparticles, wherein at least two fluids are used, wherein at least one kind of the fluids contains at least one kind of microparticle materials, and at least one kind of the fluids other than the above fluid is a fluid has a temperature difference to the fluid containing a microparticle material, and the respective fluids join together in a thin film fluid between two processing surfaces arranged opposite to each other to be able to approach to and separate from each other, at least one of which rotates relative to the other, whereby microparticles are separated in the thin film fluid by using the change of saturation solubility due to the temperature difference of the fluid containing the particle material.

An aspect of the invention according to claim 3 in the present application is the method for producing microparticles according to claim 1 or 2, wherein the separation reaction includes a fluid pressure imparting mechanism that imparts predetermined pressure to a fluid to be processed, at least two processing members of a first processing member and a second processing member capable of approaching to and separating from the first processing member, and a rotation drive mechanism that rotates the first processing member and the second processing member relative to each other, wherein each of the processing members is provided with at least two processing surfaces of a first processing surface and a second processing surface disposed in a position they are faced with each other; each of the processing surfaces constitutes part of a sealed flow path through which the fluid under the predetermined pressure is passed; two or more fluids to be processed, at least one of which contains a microparticle material, are uniformly mixed and positively reacted between the processing surfaces; of the first and second processing members, at least the second processing member is provided with a pressure-receiving surface, and at least part of the pressure-receiving surface is comprised of the second processing surface, the pressure-receiving surface receives pressure applied to the fluid by the fluid pressure imparting mechanism thereby generating a force to move in the direction of separating the second processing surface from the first processing surface; and the fluid under the predetermined pressure is passed between the first and second processing surfaces being capable of approaching to and separating from each other and rotating relative to each other, whereby the processed fluid forms a fluid film of predetermined thickness while passing between both the processing surfaces, and the separation reaction further includes another introduction path independent of the flow path through which the fluid to be processed under the predetermined pressure is passed, and at least one opening leading to the introduction path and being arranged in at least either the first processing surface or the second processing surface, wherein at least one processed fluid sent from the separate introduction path is introduced into between the processing surfaces, whereby the microparticle material contained in at least any one of the aforementioned processed fluids, and a fluid other than said processed fluid enable a state of desired reaction by mixing under uniform stirring in the fluid film.

An aspect of the invention according to claim 4 in the present application is the method for producing microparticles according to any one of claims 1 to 3, wherein at least one kind of the fluids contains a surfactant.

An aspect of the invention according to claim 5 in the present application is the method for producing microparticles according to any one of claims 1 to 4, wherein heat (warmth) is added between the processing surfaces; ultraviolet ray (UV) is irradiated between the processing surfaces; or ultrasonic energy is supplied between the processing surfaces.

An aspect of the invention according to claim 6 in the present application is the method for producing microparticles according to any one of claims 1 to 5, wherein the separation reaction is conducted in a container capable of securing a depressurized or vacuum state, at least to form a depressurized or vacuum state of a secondary side at which the fluid after processing is discharged thereby removing a gas generated during the reaction and a gas contained in the fluid, or removing a solvent of the fluid.

An aspect of the invention according to claim 7 in the present application is the method for producing microparticles according to any one of claims 1 to 6, wherein the microparticles obtained by the production method are excellent in re-dispersibility.

An aspect of the invention according to claim 8 in the present application is the method for producing microparticles according to any one of claims 1 to 7, wherein the average primary particle size of the obtained microparticles is 0.5 nm to 10000 nm.

An aspect of the invention according to claim 9 in the present application is a microparticle obtained by the method according to any one of claims 1 to 8.

The present invention relates to a method for producing microparticles obtained through separation of lysates by changing saturation solubility due to the temperature difference of fluids in a thin film fluid formed between two processing surfaces arranged to be opposite to each other to be able to approach to and separate from each other, at least one of which rotates relative to the other, and to microparticles produced by the production method. The obtained particles have a particle size smaller than that of the microparticles obtained by the conventional method, and it is possible to obtain monodispersed microparticles excellent in re-dispersibility and with no aggregation. The present invention can provide microparticles at a lower cost by processing continuously, briefly and at a lower energy than that of the conventional production method. Further, the present invention can grow in size by using general scale-up concept depending on a necessary amount of production.

BRIEF DESCRIPTION OF DRAWINGS

FIG. 1(A) is a schematic vertical sectional view showing the concept of the apparatus used for carrying out the present invention, FIG. 1(B) is a schematic vertical sectional view showing the concept of another embodiment of the apparatus, FIG. 1(C) is a schematic vertical sectional view showing the concept of still another embodiment of the apparatus, and FIG. 1(D) is a schematic vertical sectional view showing the concept of still another embodiment of the apparatus.

FIG. 2(A) to FIG. 2(D) each show a schematic vertical sectional view showing the concept of still another embodiment of the apparatus shown in FIG. 1.

FIG. 18(A) is a schematic vertical sectional view showing the concept of still another embodiment of the apparatus used for carrying out the present invention, and FIG. 18(B) is a partially cut explanatory view showing an important part of the apparatus.

FIG. 23(A) is a plane view of still another embodiment of the first processing member, and FIG. 23(B) is a plane view of still another embodiment of the first processing member.

FIG. 29 is a diagram for explaining a pressure-receiving surface arranged in the processing member.

BEST MODE FOR CARRYING OUT THE INVENTION

Figure 3A:
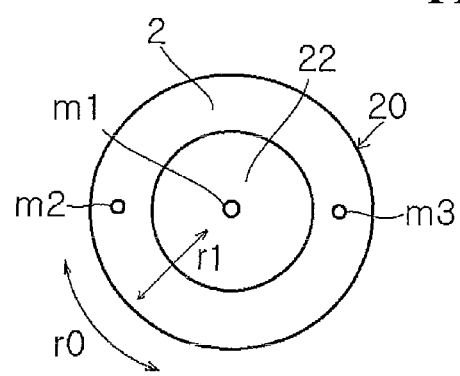
FIG. 3(A) is a schematic bottom view showing an important part of the apparatus shown in FIG. 2(C)

Hereinafter, the method for producing microparticles according to the present invention will be described in detail.

The method of the present invention comprises using a fluid in which at least one kind of microparticle materials is dissolved in a solvent, utilizing the change of saturation solubility due to the temperature difference of the fluid solvent, and separating, in the fluid, lysates to thereby produce microparticles, wherein the fluid is introduced between two processing surfaces arranged so as to be able to approach to and separate from each other, at least one of which rotates relative to the other, to be formed into a thin film fluid, and lysates are separated in the thin film fluid by utilizing the change of saturation solubility due to the temperature difference of the fluid. Further, "dissolution" as used in this specification includes dissolution in which a solute is decomposed into positive and negative ions in water such as dissolution into water, and blending or mixing of solute molecules into solvent molecules such as molecular dispersion without decomposing into ions.

An apparatus of the same principle as described in JP-A 2004-49957 filed by the present applicant, for example, can be used in the method of uniform stirring and mixing in a thin film fluid formed between processing surfaces arranged to be opposite to each other so as to be able to approach to and separate from each other, at least one of which rotates relative to the other.

Hereinafter, the fluid processing apparatus suitable for carrying out this method is described.

As shown in FIG. 1(A), this apparatus includes opposing first and second processing members 10 and 20, at least one of which rotates to the other. The opposing surfaces of both the processing members 10 and 20 serve as processing surfaces 1 and 2 to process a fluid to be processed therebetween. The first processing member 10 includes a first processing surface 1, and the second processing member 20 includes a second processing surface 2.

Both the processing surfaces 1 and 2 are connected to a flow path of the fluid to constitute a part of the flow path of the fluid.

Specifically, this apparatus constitutes flow paths of at least two fluids to be processed and joins the flow paths together.

That is, this apparatus is connected to a flow path of a first fluid to form a part of the flow path of the first fluid and simultaneously forms a part of a flow path of a second fluid different from the first fluid. This apparatus joins both the flow paths together thereby mixing and reacting, when the mixing is accompanied by reaction, both the fluids between the processing surfaces 1 and 2. In the embodiment shown in FIG. 1(A), each of the flow paths is hermetically closed and made liquid-tight (when the processed fluid is a liquid) or air-tight (when the processed fluid is a gas).

Specifically, this apparatus as shown in FIG. 1(A) includes the first processing member 10, the second processing member 20, a first holder 11 for holding the first processing member 10, a second holder 21 for holding the second processing member 20, a surface-approaching pressure imparting mechanism 4, a rotation drive member, a first introduction part d1, a second introduction part d2, a fluid pressure imparting mechanism p1, a second fluid supply part p2, and a case 3.

Illustration of the rotation drive member is omitted.

At least one of the first processing member 10 and the second processing member 20 is able to approach to and separate from each other, and the processing surfaces 1 and 2 are able to approach to and separate from each other.

In this embodiment, the second processing member 20 approaches to and separates from the first processing member 10. On the contrary, the first processing member 10 may approach to and separate from the second processing member 20, or both the processing members 10 and 20 may approach to and separate from each other.

The second processing member 20 is disposed over the first processing member 10, and the lower surface of the second processing member 20 serves as the second processing surface 2, and the upper surface of the first processing member 10 serves as the first processing surface 1.

As shown in FIG. 1(A), the first processing member 10 and the second processing member 20 in this embodiment are circular bodies, that is, rings. Hereinafter, the first processing member 10 is referred to as a first ring 10, and the second processing member 20 as a second ring 20.

Both the rings 10 and 20 in this embodiment are metallic members having, at one end, a mirror-polished surface, respectively, and their mirror-polished surfaces are referred to as the first processing surface 1 and the second processing surface 2, respectively. That is, the upper surface of the first ring 10 is mirror-polished as the first processing surface 1, and the lower surface of the second ring is mirror-polished as the second processing surface 2.

At least one of the holders can rotate relative to the other holder by the rotation drive member. In FIG. 1(A), numerical 50 indicates a rotary shaft of the rotation drive member. The rotation drive member may use an electric motor. By the rotation drive member, the processing surface of one ring can rotate relative to the processing surface of the other ring.

In this embodiment, the first holder 11 receives drive power on the rotary shaft 50 from the rotation drive member and rotates relative to the second holder 21, whereby the first ring 10 integrated with the first holder 11 rotates relative to the second ring 20. Inside the first ring 10, the rotary shaft 50 is disposed in the first holder 11 so as to be concentric, in a plane, with the center of the circular first ring 10.

The first ring 10 rotates centering on the shaft center of the ring 10. The shaft center (not shown) is a virtual line referring to the central line of the ring 10.

In this embodiment, as described above, the first holder 11 holds the first ring 10 such that the first processing surface 1 of the first ring 10 is directed upward, and the second holder 21 holds the second ring 20 such that the second processing surface 2 of the second ring 20 is directed downward.

Specifically, the first and second holders 11 and 21 include a ring-accepting concave part, respectively. In this embodiment, the first ring 10 is fitted in the ring-accepting part of the first holder 11, and the first ring 10 is fixed in the ring-accepting part so as not to rise from, and set in, the ring-accepting part of the first holder 11.

That is, the first processing surface 1 is exposed from the first holder 11 and faces the second holder 21.

Examples of the material for the first ring 10 include metal, ceramics, sintered metal, abrasion-resistant steel, metal subjected to hardening treatment, and rigid materials subjected to lining, coating or plating. Particularly, the first processing member 10 is preferably formed of a lightweight material for rotation. A material for the second ring 20 may be the same as that for the first ring 10.

On the other hand, the ring-accepting part 41 arranged in the second holder 21 accepts the processing member 2 of the second ring 20 such that the processing member can rise and set.

The ring-accepting part 41 of the second holder 21 is a concave portion for mainly accepting that side of the second ring 20 opposite to the processing surface 2, and this concave portion is a groove which has been formed into a circle when viewed in a plane.

The ring-accepting part 41 is formed larger in size than the second ring 20 and accepts the second ring 20 with sufficient clearance between itself and the second ring 20.

By this clearance, the second ring 20 in the ring-accepting part 41 can be displaced not only in the axial direction of the circular ring-accepting part 41 but also in a direction perpendicular to the axial direction. In other words, the second ring 20 can, by this clearance, be displaced relative to the ring-accepting part 41 to make the central line of the ring 20 unparallel to the axial direction of the ring-accepting part 41.

Hereinafter, that portion of the second holder 21 which is surrounded by the second ring 20 is referred to as a central portion 22.

In other words, the second ring 20 is displaceably accepted within the ring-accepting part 41 not only in the thrust direction of the ring-accepting part 41, that is, in the direction in which the ring 20 rises from and sets in the part 41, but also in the decentering direction of the ring 20 from the center of the ring-accepting part 41. Further, the second ring 20 is accepted in the ring-accepting part 41 such that the ring 20 can be displaced (i.e. run-out) to vary the width between itself upon rising or setting and the ring-accepting part 41, at each position in the circumferential direction of the ring 20.

The second ring 20, while maintaining the degree of its move in the above three directions, that is, the axial direction, decentering direction and run-out direction of the second ring 20 relative to the ring-accepting part 41, is held on the second holder 21 so as not to follow the rotation of the first ring 10. For this purpose, suitable unevenness (not shown) for regulating rotation in the circumferential direction of the ring-accepting part 41 may be arranged both in the ring-accepting part 41 and in the second ring 20. However, the unevenness should not deteriorate displacement in the degree of its move in the three directions.

The surface-approaching pressure imparting mechanism 4 supplies the processing members with force exerted in the direction of approaching the first processing surface 1 and the second processing surface 2 each other. In this embodiment, the surface-approaching pressure imparting mechanism 4 is disposed in the second holder 21 and biases the second ring 20 toward the first ring 10.

The surface-approaching pressure imparting mechanism 4 uniformly biases each position in the circumferential direction of the second ring 20, that is, each position of the processing surface 2, toward the first ring 10. A specific structure of the surface-approaching pressure imparting mechanism 4 will be described later.

As shown in FIG. 1(A), the case 3 is arranged outside the outer circumferential surfaces of both the rings 10 and 20, and accepts a product formed between the processing surfaces 1 and 2 and discharged to the outside of both the rings 10 and 20. As shown in FIG. 1(A), the case 3 is a liquid-tight container for accepting the first holder 10 and the second holder 20. However, the second holder 20 may be that which as a part of the case, is integrally formed with the case 3.

As described above, the second holder 21 whether formed as a part of the case 3 or formed separately from the case 3 is not movable so as to influence the distance between both the rings 10 and 20, that is, the distance between the processing surfaces 1 and 2. In other words, the second holder 21 does not influence the distance between the processing surfaces 1 and 2.

The case 3 is provided with an outlet 32 for discharging a product to the outside of the case 3.

The first introduction part d1 supplies a first fluid to the space between the processing surfaces 1 and 2.

The fluid pressure imparting mechanism p1 is connected directly or indirectly to the first introduction part d1 to impart fluid pressure to the first processed fluid. A compressor or a pump can be used in the fluid pressure imparting mechanism p1.

In this embodiment, the first introduction part d1 is a fluid path arranged inside the central portion 22 of the second holder 21, and one end of the first introduction part d1 is open at the central position of a circle, when viewed in a plane, of the second ring 20 on the second holder 21. The other end of the first introduction part d1 is connected to the fluid pressure imparting mechanism p1 outside the second holder 20, that is, outside the case 3.

The second introduction part d2 supplies a second fluid to be mixed with the first fluid to the space between the processing surfaces 1 and 2. In this embodiment, the second introduction part is a fluid passage arranged inside the second ring 20, and one end of the second introduction part is open at the side of the second processing surface 2, and a second fluid-feeding part p2 is connected to the other end.

A compressor or a pump can be used in the second fluid-feeding part p2.

The first processed fluid pressurized with the fluid pressure imparting mechanism p1 is introduced from the first introduction part d1 to the space between the rings 10 and 20 and will pass through the space between the first processing surface 1 and the second processing surface 2 to the outside of the rings 10 and 20.

At this time, the second ring 20 receiving the supply pressure of the first fluid stands against the bias of the surface-approaching pressure imparting mechanism 4, thereby receding from the first ring 10 and making a minute space between the processing surfaces. The space between both the processing surfaces 1 and 2 by approach and separation of the surfaces 1 and 2 will be described in detail later.

A second fluid is supplied from the second introduction part d2 to the space between the processing surfaces 1 and 2, flows into the first fluid, and is subjected to a mixing (reaction) promoted by rotation of the processing surface. Then, a reaction product formed by the mixing (reaction) of both the fluids is discharged from the space between the processing surfaces 1 and 2 to the outside of the rings 10 and 20. The product discharged to the outside of the rings 10 and 20 is discharged finally through the outlet of the case to the outside of the case (self-discharge).

The mixing and reaction (when the mixing is accompanied by reaction) of the processed fluid are effected between the first processing surface 1 and the second processing surface 2 by rotation, relative to the second processing member 20, of the first processing member 10 with the drive member 5.

Between the first and second processing surfaces 1 and 2, a region downstream from an opening m2 of the second introduction part d2 serves as a processing chamber where the first and second processed fluids are mixed with each other. Specifically, as shown in FIG. 11(C) illustrating a bottom face of the second ring 20, a region H shown by oblique lines, outside the second opening m2 of the second introduction part in the radial direction r1 of the second ring 20, serves as the processing chamber. Accordingly, this processing chamber is located downstream from the openings m1 and m2 of the first introduction part d1 and the second introduction part d2 between the processing surfaces 1 and 2.

The first fluid introduced from the first opening m1 through a space inside the ring into the space between the processing surfaces 1 and 2, and the second fluid introduced from the second opening m2 into the space between the processing surfaces 1 and 2, are mixed with each other in the region H serving as the processing chamber, and if the mixing is accompanied by reaction, both the processed fluids are reacted with each other. The fluid will, upon receiving supply pressure from the fluid pressure imparting mechanism p1, move through the minute space between the processing surfaces 1 and 2 to the outside of the rings, but because of rotation of the first ring 10, the fluid mixed in the reaction region H does not move linearly from the inside to the outside of the rings in the radial direction, but moves from the inside to the outside of the ring spirally around the rotary shaft of the ring when the processing surfaces are viewed in a plane. In the region H where the fluids are thus mixed (reacted), the fluids can move spirally from inside to outside to secure a zone necessary for sufficient mixing (reaction) in the minute space between the processing surfaces 1 and 2, thereby promoting their uniform reaction.

The product formed by the mixing (reaction) becomes a uniform reaction product in the minute space between the first processing surface 1 and the second processing surface 2 and appears as microparticles particularly in the case of crystallization or separation.

By the balance among at least the supply pressure applied by the fluid pressure imparting mechanism p1, the bias of the surface-approaching pressure imparting mechanism 4, and the centrifugal force resulting from rotation of the ring, the distance between the processing surfaces 1 and 2 can be balanced to attain a preferable minute space, and further the processed fluid receiving the supply pressure applied by the fluid pressure imparting mechanism p1 and the centrifugal force by rotation of the ring moves spirally in the minute space between the processing surfaces 1 and 2, so that their mixing (reaction) is promoted.

The mixing (reaction) is forcedly effected by the supply pressure applied by the fluid pressure imparting mechanism p1 and the rotation of the ring. That is, the mixing (reaction) occurs under forced uniform mixing between the processing surfaces 1 and 2 arranged opposite to each other so as to be able to approach to and separate from each other, at least one of which rotates relative to the other.

Accordingly, the crystallization and separation of the product formed by the reaction can be regulated by relatively easily controllable methods such as regulation of supply pressure applied by the fluid pressure imparting mechanism p1 and regulation of the rotation speed of the ring, that is, the number of rotations of the ring.

As described above, this fluid processing apparatus is excellent in that the space between the processing surfaces 1 and 2, which can exert influence on the size of a product, and the distance in which the processed fluid moves in the region H, which can exert influence on formation of a uniform product, can be regulated by the supply pressure and the centrifugal force.

The processing gives not only deposit of the product but also liquids. When the product is fine mass such as microparticles, it may be a deposit in the fluid after processing or may be in a dispersion state in which a dispersed phase is present in a continuous phase.

The rotary shaft 50 is not limited to the vertically arranged one and may be arranged in the horizontal direction or arranged at a slant. This is because during processing, the mixing (reaction) occurs in such a minute space between the processing surfaces 1 and 2 that the influence of gravity can be substantially eliminated.

In FIG. 1(A), the first introduction part d1 extends vertically and coincides with the shaft center of the second ring 20 in the second holder 21. However, the first introduction part d1 is not limited to the one having a center coinciding with the shaft center of the second ring 20 and may be arranged in other positions in the central portion 22 of the second holder 21 as long as the first fluid can be supplied into the space surrounded by the rings 10 and 20, and the first introduction part d1 may extend obliquely as well as vertically.

Figure 12A:
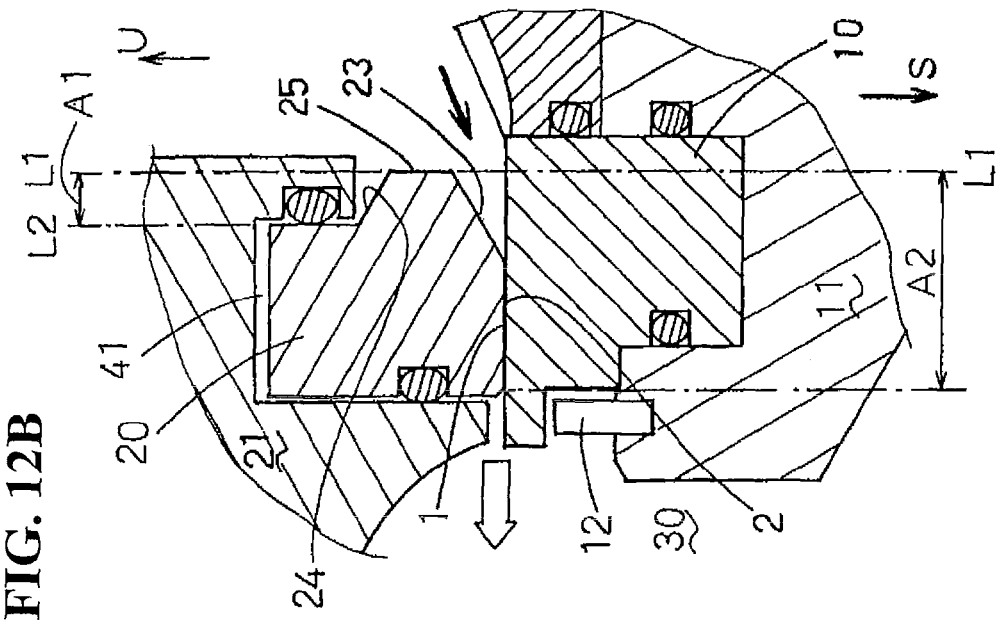
FIG. 12(A) is a schematic vertical sectional view showing an important part of another embodiment of a pressure-receiving surface in the apparatus shown in FIG. 1(A)

A more preferable embodiment of the apparatus is shown in FIG. 12(A). As shown in this figure, the second processing member 20 has the second processing surface 2 and a pressure-receiving surface 23 which is positioned inside, and situated next to, the second processing surface 2. Hereinafter, the pressure-receiving surface 23 is also referred to as a separation-regulating surface 23. As shown in the figure, the separation regulating surface 23 is an inclined surface.

As described above, the ring-accepting part 41 is formed in the bottom (i.e. a lower part) of the second holder 21, and the second processing member 20 is accepted in the ring-accepting part 41. The second processing member 20 is accepted by the second holder 21 so as not to be rotated with a baffle (not shown). The second processing surface 2 is exposed from the second holder 21.

In this embodiment, a material to be processed is introduced inside the first processing member 10 and the second processing member 20 between the processing surfaces 1 and 2, and the processed material is discharged to the outside of the first processing member 10 and the second processing member 20.

The surface-approaching pressure imparting mechanism 4 presses by pressure the second processing surface 2 against the first processing surface 1 to make them contacted with or close to each other, and generates a fluid film of predetermined thickness by the balance between the surface-approaching pressure and the force, e.g. fluid pressure, of separating the processing surfaces 1 and 2 from each other. In other words, the distance between the processing surfaces 1 and 2 is kept in a predetermined minute space by the balance between the forces.

Specifically, the surface-approaching pressure imparting mechanism 4 in this embodiment is comprised of the ring-accepting part 41, a spring-accepting part 42 arranged in the depth of the ring-accepting part 41, that is, in the deepest part of the ring-accepting part 41, a spring 43, and an air introduction part 44.

However, the surface-approaching pressure imparting mechanism 4 may be the one including at least one member selected from the ring accepting part 41, the spring-accepting part 42, the spring 43, and the air introduction part 44.

The ring-accepting part 41 has the second processing member 20 fit into it with play to enable the second processing member 20 to be displaced vertically deeply or shallowly, that is, vertically in the ring-accepting part 41.

One end of the spring 43 is abutted against the depth of the spring-accepting part 42, and the other end of the spring 43 is abutted against the front (i.e. the upper part) of the second processing member 20 in the ring-accepting part 41. In FIG. 1, only one spring 43 is shown, but a plurality of springs 44 are preferably used to press various parts of the second processing member 20. This is because as the number of the springs 43 increases, pressing pressure can be given more uniformly to the second processing member 20. Accordingly, several to a few dozen springs 43 comprising a multi-spring type preferably attach to the second holder 21.

In this embodiment, air can be introduced through the air introduction part 44 into the ring-accepting part 41. By such introduction of air, air pressure together with pressure by the spring 43 can be given as pressing pressure from the space, as a pressurizing chamber, between the ring-accepting part 41 and the second processing member 20 to the second processing member 20. Accordingly, adjusting the pressure of air introduced through the air introduction part 44 can regulate the surface-approaching pressure of the second processing surface 2 toward the first processing surface 1 during operation. A mechanism of generating pressing pressure with another fluid pressure such as oil pressure can be utilized in place of the air introduction part 44 utilizing air pressure.

The surface-approaching pressure imparting mechanism 4 not only supplies and regulates apart of the pressing pressure, that is, the surface-approaching pressure, but also serves as a displacement regulating mechanism and a buffer mechanism.

Specifically, the surface-approaching pressure imparting mechanism 4 as a displacement regulating mechanism can maintain initial pressing pressure by regulating air pressure against the change in the axial direction caused by elongation or abrasion at the start of or in the operation. As described above, the surface-approaching pressure imparting mechanism 4 uses a floating mechanism of maintaining the second processing member 20 so as to be displaced, thereby also functioning as a buffer mechanism for micro-vibration or rotation alignment.

Now, the state of the thus constituted processing apparatus during use is described with reference to FIG. 1(A).

At the outset, a first processed fluid is pressurized with the fluid pressure imparting mechanism p1 and introduced through the first introduction part d1 into the internal space of the sealed case. On the other hand, the first processing member 10 is rotated with the rotation of the rotary shaft 50 by the rotation drive member. The first processing surface 1 and the second processing surface 2 are thereby rotated relatively with a minute space kept therebetween.

The first processed fluid is formed into a fluid film between the processing surfaces 1 and 2 with a minute space kept therebetween, and a second processed fluid which is introduced through the second introduction part d2 flows into the fluid film between the processing surfaces 1 and 2 to comprise a part of the fluid film. By this, the first and second processed fluids are mixed with each other to form a product. When the mixing is accompanied by reaction, a uniform reaction of both of the fluids being reacted with each other is promoted to form a reaction product. When the reaction is accompanied by separation, relatively uniform and fine particles can be formed. Even when the reaction is not accompanied by separation, a uniform mixing (uniform reaction when the mixing is accompanied by reaction) can be realized. The separated product may be further finely pulverized by shearing between the first processing surface 1 and the second processing surface 2 with the rotation of the first processing surface 1. The first processing surface 1 and the second processing surface 2 are regulated to form a minute space of 1 µm to 1 mm, particularly 1 µm to 10 µm, thereby realizing a uniform mixing (uniform reaction when the mixing is accompanied by reaction) and enabling formation of superfine particles of several nm in diameter.

The product is discharged from the processing surfaces 1 and 2 through an outlet 33 of the case 3 to the outside of the case. The discharged product is atomized in a vacuum or depressurized atmosphere with a well-known decompression device and converted into liquid in the atmosphere to hit each other, then what trickled down in the liquid is able to be collected as degassed liquid.

In this embodiment, the processing apparatus is provided with a case, but may be carried out without a case. For example, a decompression tank for degassing, that is, a vacuum tank, is arranged, and the processing apparatus may be arranged in this tank. In this case, the outlet mentioned above is naturally not arranged in the processing apparatus.

As described above, the first processing surface 1 and the second processing surface 2 can be regulated to form a minute space in the order of µm which cannot be formed by arranging mechanical clearance. Now, this mechanism is described.

The first processing surface 1 and the second processing surface 2 are capable of approaching to and separating from each other, and simultaneously rotate relative to each other. In this example, the first processing surface 1 rotates, and the second processing surface 2 approaches to and separates from the first processing surface with a structure capable of moving in the axial direction (floating structure).

In this example, therefore, the position of the second processing surface 2 in the axial direction is arranged accurately in the order of µm by the balance between forces, that is, the balance between the surface-approaching pressure and the separating pressure, thereby establishing a minute space between the processing surfaces 1 and 2.

As shown in FIG. 12(A), the surface-approaching pressure includes the pressure by air pressure (positive pressure) from the air introduction part 44 by the surface-approaching pressure imparting mechanism 4, the pressing pressure with the spring 43, and the like.

Figure 13:
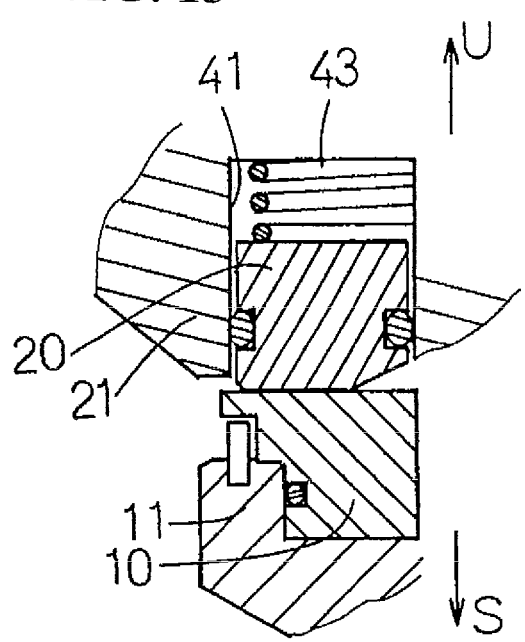
FIG. 13 is a schematic vertical sectional view showing an important part of another embodiment of a surface-approaching pressure imparting mechanism 4 in the apparatus shown in FIG. 12(A).
Figure 14:
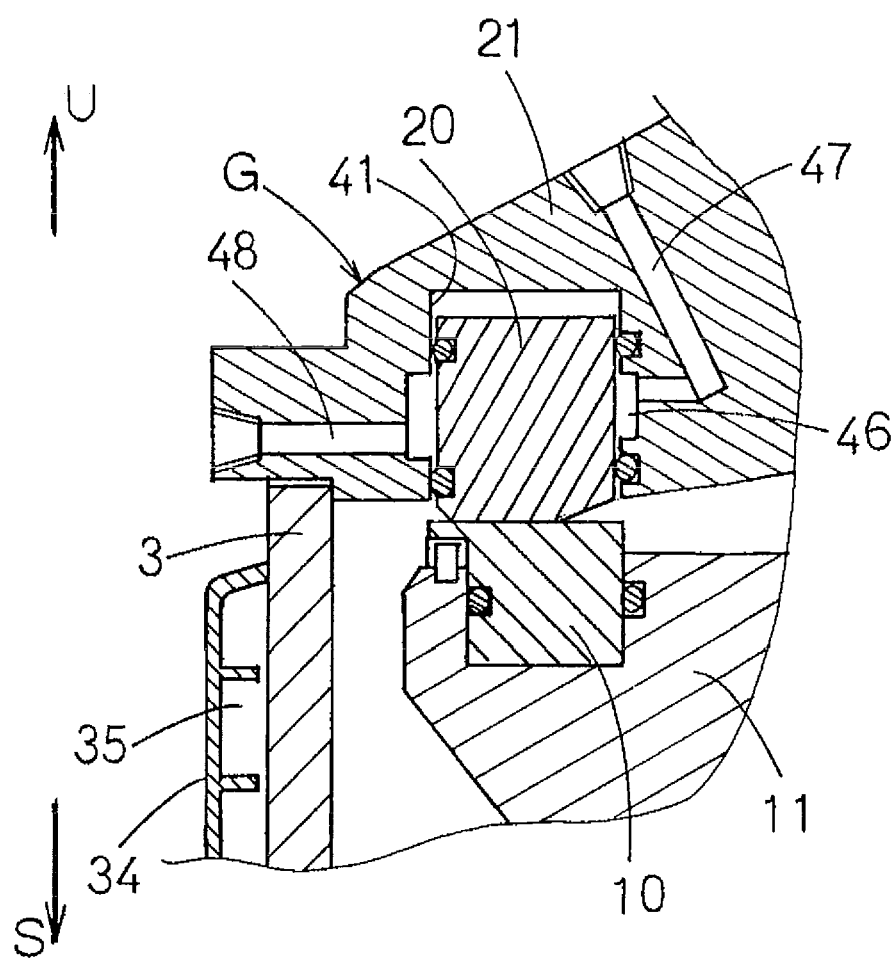
FIG. 14 is a schematic vertical sectional view showing an important part of another embodiment of the apparatus shown in FIG. 12(A), which is provided with a temperature regulating jacket.
Figure 15:
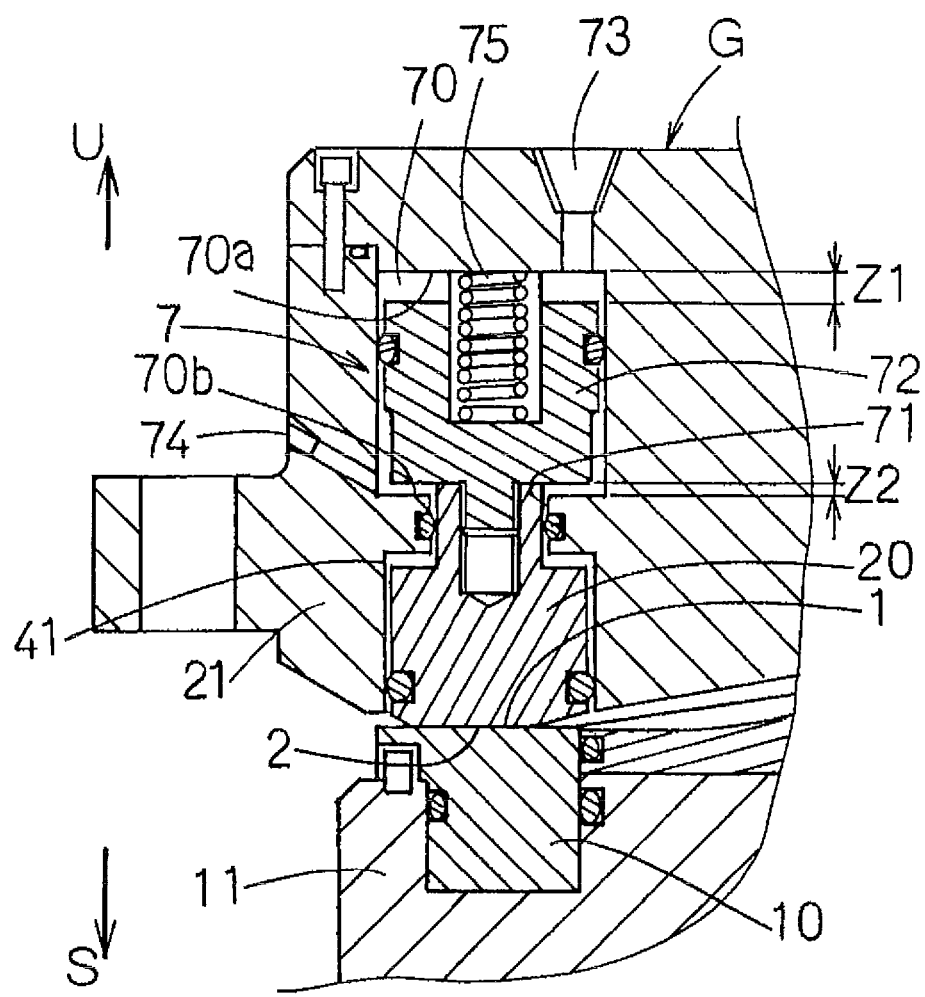
FIG. 15 is a schematic vertical sectional view showing an important part of still another embodiment of the surface-approaching pressure imparting mechanism 4 in the apparatus shown in FIG. 12(A).

The embodiments shown in FIG. 13 to FIG. 15 are shown by omitting the second introduction part d2 to simplify the drawings. In this respect, these drawings may be assumed to show sections at a position not provided with the second introduction part d2. In the figures, U and S show upward and downward directions respectively.

On the other hand, the separating force include the fluid pressure acting on the pressure-receiving surface at the separating side, that is, on the second processing surface 2 and the separation regulating surface 23, the centrifugal force resulting from rotation of the first processing member 1, and the negative pressure when negative pressure is applied to the air introduction part 44.

When the apparatus is washed, the negative pressure applied to the air introduction part 44 can be increased to significantly separate the processing surfaces 1 and 2 from each other, thereby facilitating washing.

By the balance among these forces, the second processing surface 2 while being remote by a predetermined minute space from the first processing surface 1 is stabilized, thereby realizing establishment with accuracy in the order of µm.

The separating force is described in more detail.

With respect to fluid pressure, the second processing member 20 in a closed flow path receives feeding pressure of a processed fluid, that is, fluid pressure, from the fluid pressure imparting mechanism p. In this case, the surfaces opposite to the first processing surface in the flow path, that is, the second processing surface 2 and the separation regulating surface 23, act as pressure-receiving surfaces at the separating side, and the fluid pressure is applied to the pressure-receiving surfaces to generate a separating force due to the fluid pressure.

With respect to centrifugal force, the first processing member 10 is rotated at high speed, centrifugal force is applied to the fluid, and a part of this centrifugal force acts as a separating force in the direction in which the processing surfaces 1 and 2 are separated from each other.

When negative pressure is applied from the air introduction part 44 to the second processing member 20, the negative pressure acts as a separating force.

In the foregoing description of the present invention, the force of separating the first and second processing surfaces 1 and 2 from each other has been described as a separating force, and the above-mentioned force is not excluded from the separating force.

By forming a balanced state of the separating force and the surface-approaching pressure applied by the surface-approaching pressure imparting mechanism 4 via the processed fluid between the processing surfaces 1 and 2 in the flow path of the closed processed fluid, a uniform mixing (when the mixing is accompanied by reaction, uniform reaction) is realized between the processing surfaces 1 and 2, and simultaneously a fluid film suitable for crystallization and separation of microscopic products is formed as described above. In this manner, this apparatus can form a forced fluid film between the processing surfaces 1 and 2 via which a minute space not achievable with a conventional mechanical apparatus can be kept between the processing surfaces 1 and 2, and microparticles can be formed highly accurately as the reaction product.

In other words, the thickness of the fluid film between the processing surfaces 1 and 2 is regulated as desired by regulating the separating force and surface-approaching pressure, thereby realizing a necessary uniform mixing (when the mixing is accompanied by reaction, uniform reaction) to form and process microscopic products. Accordingly, when the thickness of the fluid film is to be decreased, the surface-approaching pressure or separating force may be regulated such that the surface-approaching pressure is made relatively higher than the separating force. When the thickness of the fluid film is to be increased, the separating force or surface-approaching pressure may be regulated such that the separating force is made relatively higher than the surface-approaching pressure.

When the surface-approaching pressure is increased, air pressure, that is, positive pressure is applied from the air introduction part 44 by the surface-approaching pressure imparting mechanism 4, or the spring 43 is changed to the one having higher pressing pressure, or the number of the springs may be increased.

When the separating force is to be increased, the feeding pressure of the fluid pressure imparting mechanism p1 is increased, or the area of the second processing surface 2 or the separation regulating surface 23 is increased, or in addition, the rotation of the second processing member 20 is regulated to increase centrifugal force or reduce pressure from the air introduction part 44. Alternatively, negative pressure may be applied. The spring 43 shown is a pressing spring that generates pressing pressure in an extending direction, but may be a pulling spring that generates a force in a compressing direction to constitute a part or the whole of the surface-approaching pressure imparting mechanism 4.

When the separating force is to be decreased, the feeding pressure of the fluid pressure imparting mechanism p1 is reduced, or the area of the second processing surface 2 or the separation regulating surface 23 is reduced, or in addition, the rotation of the second processing member 20 is regulated to decrease centrifugal force or increase pressure from the air introduction part 44. Alternatively, negative pressure may be reduced.

Further, properties of a processed fluid, such as viscosity, can be added as a factor for increasing or decreasing the surface-approaching pressure and separating force, and regulation of such properties of a processed fluid can be performed as regulation of the above factor.

In the separating force, the fluid pressure exerted on the pressure-receiving surface at the separating side, that is, the second processing surface 2 and the separation regulating surface 23 is understood as a force constituting an opening force in mechanical seal.

In the mechanical seal, the second processing member 20 corresponds to a compression ring, and when fluid pressure is applied to the second processing member 2, the force of separating the second processing member 2 from the first processing member 1 is regarded as an opening force.

More specifically, when the pressure-receiving surfaces at a separating side, that is, the second processing surface 2 and the separation regulating surface 23 only are arranged in the second processing member 20 as shown in the first embodiment, all feeding pressure constitutes the opening force. When a pressure-receiving surface is also arranged at the backside of the second processing member 20, specifically in the case of FIG. 12(B) and FIG. 17 described later, the difference between the feeding pressure acting as a separating force and the feeding pressure acting as surface-approaching pressure is the opening force.

Now, other embodiments of the second processing member 20 are described with reference to FIG. 12(B).

Figure 12B:
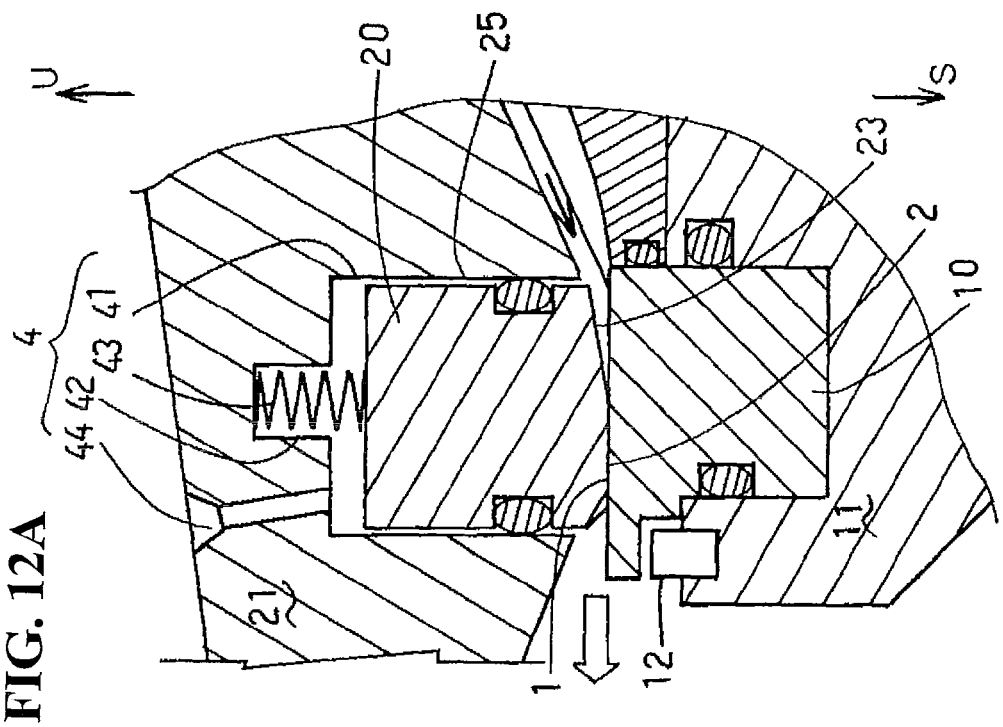
FIG. 12(B) is a schematic vertical sectional view showing an important part of still another embodiment of the apparatus.

As shown in FIG. 12(B), an approach regulating surface 24 facing upward, that is, at the other side of the second processing surface 2, is disposed at the inner periphery of the second processing member 20 exposed from the ring-accepting part 41.

That is, the surface-approaching pressure imparting mechanism 4 in this embodiment is comprised of a ring-accepting part 41, an air introduction part 44, and the approach regulating surface 24. However, the surface-approaching pressure imparting mechanism 4 may be one including at least one member selected from the ring-accepting part 41, the spring-accepting part 42, the spring 43, the air introduction part 44, and the approach regulating surface 24.

The approach regulating surface 24 receives predetermined pressure applied to a processed fluid to generate a force of approaching the second processing surface 2 to the first processing surface 1, thereby functioning in feeding surface-approaching pressure as a part of the surface-approaching pressure imparting mechanism 4. On the other hand, the second processing surface 2 and the separation regulating surface 23 receive predetermined pressure applied to a processed fluid to generate a force of separating the second processing surface 2 from the first processing surface 1, thereby functioning in feeding a part of the separating force.

The approach regulating surface 24, the second processing surface 2 and the separation regulating surface 23 are pressure-receiving surfaces receiving feeding pressure of the processed fluid, and depending on its direction, exhibits different actions, that is, generation of the surface-approaching pressure and generation of a separating force.

The ratio (area ratio A1/A2) of a projected area A1 of the approach regulating surface 24 projected on a virtual plane perpendicular to the direction of approaching and separating the processing surfaces, that is, in the direction of rising and setting of the second ring 20, to a total area A2 of the projected area of the second processing surface 2 and the separating side pressure-receiving surface 23 of the second processing member 20 projected on the virtual plane is called balance ratio K which is important for regulation of the opening force.

Both the top of the approach regulating surface 24 and the top of the separating side pressure-receiving surface 23 are defined by the inner periphery 25 of the circular second regulating part 20, that is, by top line L1. Accordingly, the balance ratio K is regulated for deciding the place where base line L2 of the approach regulating surface 24 is to be placed.

That is, in this embodiment, when the feeding pressure of the processed fluid is utilized as an opening force, the total projected area of the second processing surface 2 and the separation regulating surface 23 is made larger than the projected area of the approach regulating surface 24, thereby generating an opening force in accordance with the area ratio.

The opening force can be regulated by the pressure of the processed fluid, that is, the fluid pressure, by changing the balance line, that is, by changing the area A1 of the approach regulating surface 24.

Sliding surface actual surface pressure P, that is, the fluid pressure out of the surface-approaching pressure, is calculated according to the following equation:

$$P = P1 \times (K-k) + Ps$$

wherein P1 represents the pressure of a processed fluid, that is, fluid pressure, K represents the balance ratio, k represents an opening force coefficient, and Ps represents a spring and back pressure.

By regulating this balance line to regulate the sliding surface actual surface pressure P, the space between the processing surfaces 1 and 2 is formed as a desired minute space, thereby forming a fluid film of a processed fluid to make the product minute and effecting uniform mixing (reaction) processing.

Usually, as the thickness of a fluid film between the processing surfaces 1 and 2 is decreased, the product can be made finer. On the other hand, as the thickness of the fluid film is increased, processing becomes rough and the throughput per unit time is increased. By regulating the sliding surface actual surface pressure P on the sliding surface, the space between the processing surfaces 1 and 2 can be regulated to realize the desired uniform mixing (when the mixing is accompanied by reaction, uniform reaction) and to give the minute product. Hereinafter, the sliding surface actual surface pressure P is referred to as surface pressure P.

From this relation, it is concluded that when the product is to be made coarse, the balance ratio may be decreased, the surface pressure P may be decreased, the space may be increased and the thickness of the film may be increased. On the other hand, when the product is to be made finer, the balance ratio K may be increased, the surface pressure P may be increased, the space may be decreased and the thickness of the film may be decreased.

As a part of the surface-approaching pressure imparting mechanism 4, the approach regulating surface 24 is formed, and at the position of the balance line, the surface-approaching pressure may be regulated, that is, the space between the processing surfaces may be regulated.

As described above, the space is regulated in consideration of the pressing pressure of the spring 43 and the air pressure of the air introduction part 44. Regulation of the fluid pressure, that is, the feeding pressure of the processed fluid, and regulation of the rotation of the first processing member 10 for regulating centrifugal force, that is, the rotation of the first holder 11, are also important factors to regulate the space.

As described above, this apparatus is constituted such that for the second processing member 20 and the first processing member 10 that rotates relative to the second processing member 20, a predetermined fluid film is formed between the processing surfaces by pressure balance among the feeding pressure of the processed fluid, the rotation centrifugal force, and the surface-approaching pressure. At least one of the rings is formed in a floating structure by which alignment such as run-out is absorbed to eliminate the risk of abrasion and the like.

The embodiment shown in FIG. 1(A) also applies to the embodiment in FIG. 12(B) except that the regulating surface is arranged.

Figure 17:
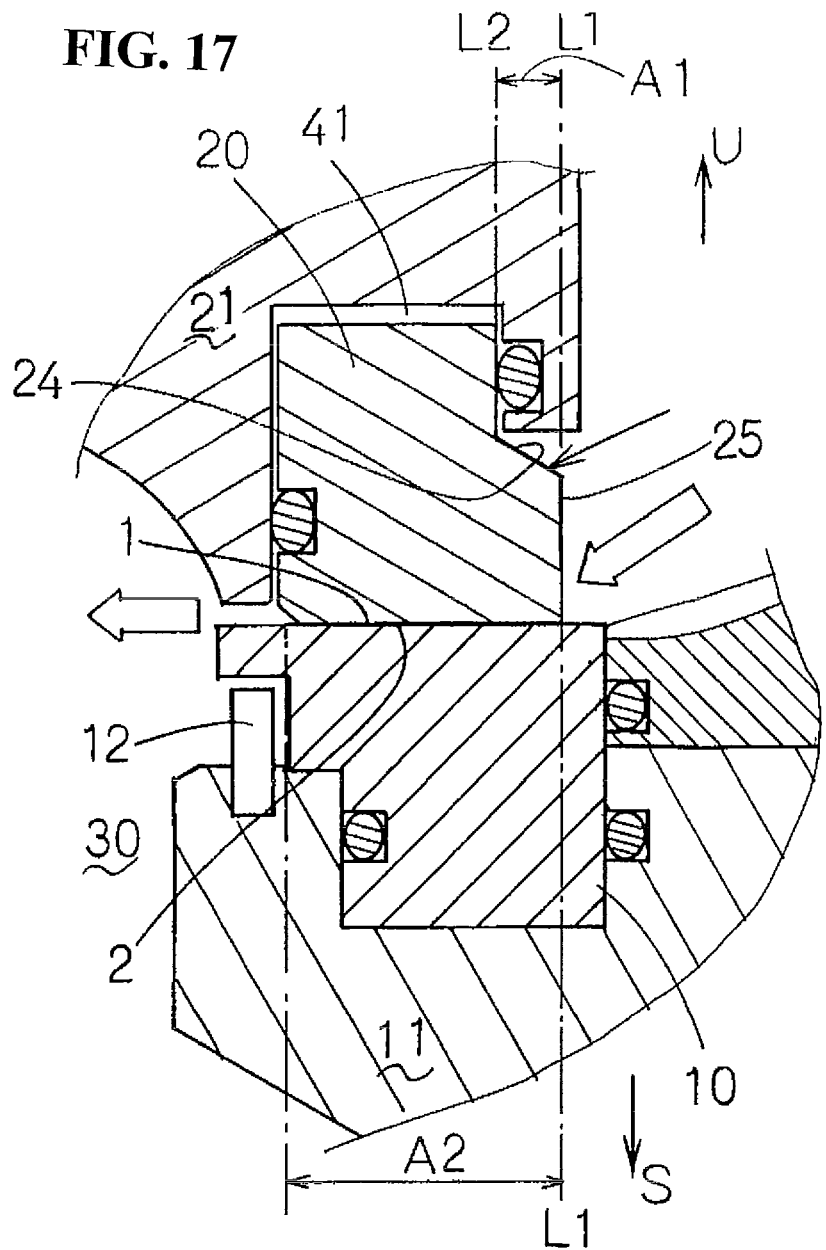
FIG. 17 is a schematic vertical sectional view showing an important part of still another embodiment of the apparatus shown in FIG. 12(A).

The embodiment shown in FIG. 12(B) can be carried out without arranging the pressure-receiving surface 23 on the separating side, as shown in FIG. 17.

When the approach regulating surface 24 is arranged as shown in the embodiment shown in FIG. 12(B) and FIG. 17, the area A1 of the approach regulating surface 24 is made larger than the area A2, whereby all of the predetermined pressure exerted on the processed fluid functions as surface-approaching pressure, without generating an opening force. This arrangement is also possible, and in this case, both the processing surfaces 1 and 2 can be balanced by increasing other separating force.

With the area ratio described above, the force acting in the direction of separating the second processing surface 2 from the first processing surface 1 is fixed as the resultant force exerted by the fluid.

In this embodiment, as described above, the number of the springs 43 is preferably larger in order to impart uniform stress on the sliding surface, that is, the processing surface. However, the spring 43 may be a single coil-type spring as shown in FIG. 13. As shown in the figure, this spring is a single coil spring having a center concentric with the circular second processing member 20.

The space between the second processing member 20 and the second holder 21 is sealed air-tightly with methods well known in the art.

As shown in FIG. 14, the second holder 21 is provided with a temperature regulation jacket 46 capable of regulating the temperature of the second processing member 20 by cooling or heating. Numerical 3 in FIG. 14 is the above-mentioned case, and the case 3 is also provided with a jacket 35 for the same purpose of temperature regulation.

The temperature regulation jacket 46 for the second holder 21 is a water-circulating space formed at a side of the ring-accepting part 41 and communicates with paths 47 and 48 leading to the outside of the second holder 21. One of the paths 47 and 48 introduces a cooling or heating medium into the temperature regulation jacket 46, and the other discharges the medium.

The temperature regulation jacket 35 for the case 3 is a path for passing heating water or cooling water, which is arranged between outer periphery of the case 3 and a covering part 34 for covering the outer periphery of the case 3.

In this embodiment, the second holder 21 and the case 3 are provided with the temperature regulation jacket, but the first holder 11 can also be provided with such a jacket.

As a part of the surface-approaching pressure imparting mechanism 4, a cylinder mechanism 7 shown in FIG. 15 may be arranged besides the members described above.

The cylinder mechanism 7 includes a cylinder space 70 arranged in the second holder 21, a communicating part 71 that communicates the cylinder space 70 with the ring-accepting part 41, a piston 72 that is accepted in the cylinder space 70 and connected via the communication part 71 to the second processing member 20, a first nozzle 73 that communicates to the upper part of the cylinder space 70, a second nozzle 74 in a lower part of the cylinder space 70, and a pressing body 75 such as spring between the upper part of the cylinder space 70 and the piston 72.

The piston 72 can slide vertically in the cylinder space 70, and the second processing member 20 can slide vertically with sliding of the piston 72, to change the gap between the first processing surface 1 and the second processing surface 2.

Although not shown in the figure, specifically, a pressure source such as a compressor is connected to the first nozzle 73, and air pressure, that is, positive pressure is applied from the first nozzle 73 to the upper part of the piston 72 in the cylinder space 70, thereby sliding the piston 72 downward, to allow the second processing member 20 to narrow the gap between the first and second processing surfaces 1 and 2. Although not shown in the figure, a pressure source such as a compressor is connected to the second nozzle 74, and air pressure, that is, positive pressure is applied from the second nozzle 74 to the lower part of the piston 72 in the cylinder space 70, thereby sliding the piston 72 upward, to allow the second processing member 20 to widen the gap between the first and second processing surfaces 1 and 2, that is, to enable it to move in the direction of opening the gap. In this manner, the surface-approaching pressure can be regulated by air pressure with the nozzles 73 and 74.

Even if there is a space between the upper part of the second processing member 20 in the ring-accepting part 41 and the uppermost part of the ring-accepting part 41, the piston 7 is arranged so as to abut against an uppermost part 70a of the cylinder space 70, whereby the uppermost part 70a of the cylinder space 70 defines the upper limit of the width of the gap between the processing surfaces 1 and 2. That is, the piston 7 and the uppermost part 70a of the cylinder space 70 function as a separation preventing part for preventing the separation of the processing surfaces 1 and 2 from each other, in other words, function in regulating the maximum opening of the gap between both the processing surfaces 1 and 2.

Even if the processing surfaces 1 and 2 do not abut on each other, the piston 7 is arranged so as to abut against a lowermost part 70b of the cylinder space 70, whereby the lowermost part 70b of the cylinder space 70 defines the lower limit of the width of the gap between the processing surfaces 1 and 2. That is, the piston 7 and the lowermost part 70b of the cylinder space 70 function as an approach preventing part for preventing the approaching of the processing surfaces 1 and 2 each other, in other words, function in regulating the minimum opening of the gap between both the processing surfaces 1 and 2.

In this manner, the maximum and minimum openings of the gap are regulated, while a distance z1 between the piston 7 and the uppermost part 70a of the cylinder space 70, in other words, a distance z2 between the piston 7 and the lowermost part 70b of the cylinder space 70, is regulated with air pressure by the nozzles 73 and 74.

The nozzles 73 and 74 may be connected to a different pressure source respectively, and further may be connected to a single pressure source alternatively or switched the connections to the sources.

The pressure source may be a source applying positive or negative pressure. When a negative pressure source such as a vacuum is connected to the nozzles 73 and 74, the action described above goes to the contrary.

In place of the other surface-approaching pressure imparting mechanism 4 or as a part of the surface-approaching pressure imparting mechanism 4, such cylinder mechanism 7 is provided to set the pressure of the pressure source connected to the nozzle 73 and 74, and the distances z1 and z2 according to the viscosity and properties of the fluid to be processed in a fashion to bring the thickness value of fluid film of the fluid to a desired level under a shear force to realize a uniform mixing (uniform reaction when the mixing is accompanied by reaction) for forming fine particles. Particularly, such cylinder mechanism 7 can be used to increase the reliability of cleaning and sterilization by forcing the sliding part open and close during cleaning and steam sterilization.

As shown in FIG. 16(A) to FIG. 16(C), the first processing surface 1 of the first processing member 10 may be provided with groove-like depressions 13 . . . 13 extending in the radial direction, that is, in the direction from the center to the outside of the first processing member 10. In this case, as shown in FIG. 16(A), the depressions 13 . . . 13 can be curved or spirally elongated on the first processing surface 1, and as shown in FIG. 16(B), the individual depression 13 may be bent at a right angle, or as shown in FIG. 16(C), the depressions 13 . . . 13 may extend straight radially.

As shown in FIG. 16(D), the depressions 13 in FIG. 16(A) to FIG. 16(C) preferably deepen gradually in the direction toward the center of the first processing surface 1. The groove-like depressions 13 may continue in sequence or intermittence.

Formation of such depression 13 may correspond to the increase of delivery of the processed fluid or to the decrease of calorific value, while having effects of cavitation control and fluid bearing.

Figure 16:
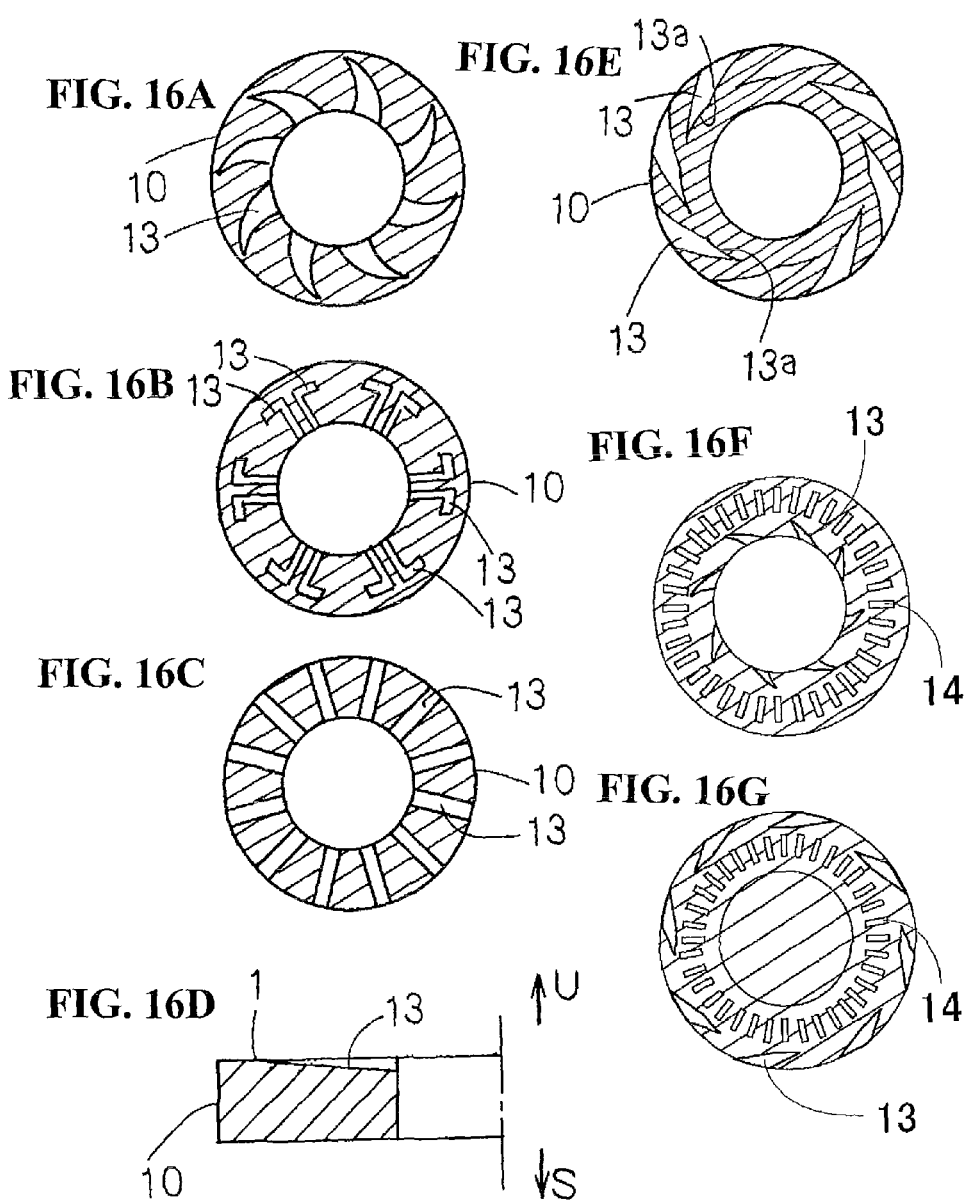
FIG. 16(A) is a schematic transverse sectional view showing an important part of still another embodiment of the apparatus shown in FIG. 12(A), FIG. 16(B), FIG. 16(C), and FIG. 16(E) to FIG. 16(G) are schematic transverse sectional views each showing an important part of still another embodiment of the apparatus.
FIG. 16(D) is a partially cut schematic vertical sectional view showing an important part of still another embodiment of the apparatus.

In the embodiments shown in FIG. 16, the depressions 13 are formed on the first processing surface 1, but may be formed on the second processing surface 2 or may be formed on both the first and second processing surfaces 1 and 2.

When the depressions 13 or tapered sections are not provided on the processing surface or are arranged unevenly on a part of the processing surface, the influence exerted by the surface roughness of the processing surfaces 1 and 2 on the processed fluid is greater than that by the above depressions 13. Accordingly, in this case, the surface roughness should be reduced, that is, the surface should be fine-textured, as the particle size of the processed fluid are to be decreased. Particularly, regarding the surface roughness of the processing surface, the mirror surface, that is, a surface subjected to mirror polishing is advantageous in realizing uniform mixing (when the mixing is accompanied by reaction, uniform reaction) for the purpose of uniform mixing (reaction), and in realizing crystallization and separation of fine monodisperse products for the purpose of obtaining microparticles.

In the embodiments shown in FIG. 12 to FIG. 17, structures other than those particularly shown are the same as in the embodiments shown in FIG. 1(A) or FIG. 11(C).

In the embodiments described above, the case is closed. Alternatively, the first processing member 10 and the second processing member 20 may be closed inside but may be open outside. That is, the flow path is sealed until the processed fluid has passed through the space between the first processing surface 1 and the second processing surface 2, to allow the processed fluid to receive the feeding pressure, but after the passing, the flow path may be opened so that the processed fluid after processing does not receive feeding pressure.

The fluid pressure imparting mechanism p1 preferably uses a compressor as a pressure device described above, but if predetermined pressure can always be applied to the processed fluid, another means may be used. For example, the own weight of the processed fluid can be used to apply certain pressure constantly to the processed fluid.

In summary, the processing apparatus in each embodiment described above is characterized in that predetermined pressure is applied to a fluid to be processed, at least two processing surfaces, that is, a first processing surface 1 and a second processing surface 2 capable of approaching to and separating from each other are connected to a sealed flow path through which the processed fluid receiving the predetermined pressure flows, a surface-approaching pressure of approaching the processing surfaces 1 and 2 each other is applied to rotate the first processing surface 1 and the second processing surface 2 relative to each other, thereby allowing a fluid film used for seal in mechanical seal to be generated out of the processed fluid, and the fluid film is leaked out consciously (without using the fluid film as seal) from between the first processing surface 1 and the second processing surface 2, contrary to mechanical seal, whereby mixing (reaction) processing is realized between the processed fluid formed into a film between the surfaces 1 and 2, and the product is recovered.

By this epoch-making method, the space between the processing surfaces 1 and 2 can be regulated in the range of 1 μm to 1 mm, particularly 1 μm to 10 μm.

In the embodiment described above, a flow path for a sealed fluid is constituted in the apparatus, and the processed fluid is pressurized with the fluid pressure imparting mechanism p1 arranged at the side of the introduction part (for the first processing fluid) in the processing apparatus.

Alternatively, the flow path for the processed fluid may be opened without pressurization with the fluid pressure imparting mechanism p1.

One embodiment of the processing apparatus is shown in FIG. 18 to FIG. 20. The processing apparatus illustrated in this embodiment is an apparatus including a degassing mechanism, that is, a mechanism of removing a liquid from the formed processed product thereby finally securing objective solids (crystals) only.

FIG. 18(A) is a schematic vertical sectional view of the processing apparatus, and FIG. 18(B) is its partially cut enlarged sectional view. FIG. 19 is a plane view of the first processing member 1 arranged in the processing apparatus in FIG. 18. FIG. 20 is a partially cut schematic vertical sectional view showing an important part of the first and second processing members 1 and 2 in the processing apparatus.

As described above, the apparatus shown in FIG. 18 to FIG. 20 is the one into which a fluid as the object of processing, that is, a processed fluid, or a fluid carrying the object of processing, is to be introduced at atmospheric pressure.

In FIG. 18(B) and FIG. 20, the second introduction part d2 is omitted for simplicity of the drawing (these drawings can be regarded as showing a section at the position where the second introduction part d2 is not arranged).

As shown in FIG. 18(A), this fluid processing apparatus includes a mixing apparatus G and a decompression pump Q. This mixing apparatus G includes a first processing member 101 as a rotating member, a first holder 111 for holding the processing member 101, a second processing member 102 that is a member fixed to the case, a second holder 121 having the second processing member 102 fixed thereto, a bias mechanism 103, a dynamical pressure generating mechanism 104 (FIG. 19(A)), a drive part which rotates the first processing member 101 with the first holder 111, a housing 106, a first introduction part d1 which supplies (introduces) a first processed fluid, and a discharge part 108 that discharges the fluid to the decompression pump Q. The drive part is not shown.

The first processing member 101 and the second processing member 102 are cylindrical bodies that are hollow in the center. The processing members 101 and 102 are members wherein the bottoms of the processing members 101 and 102 in a cylindrical form are processing surfaces 110 and 120 respectively.

Figure 19A:
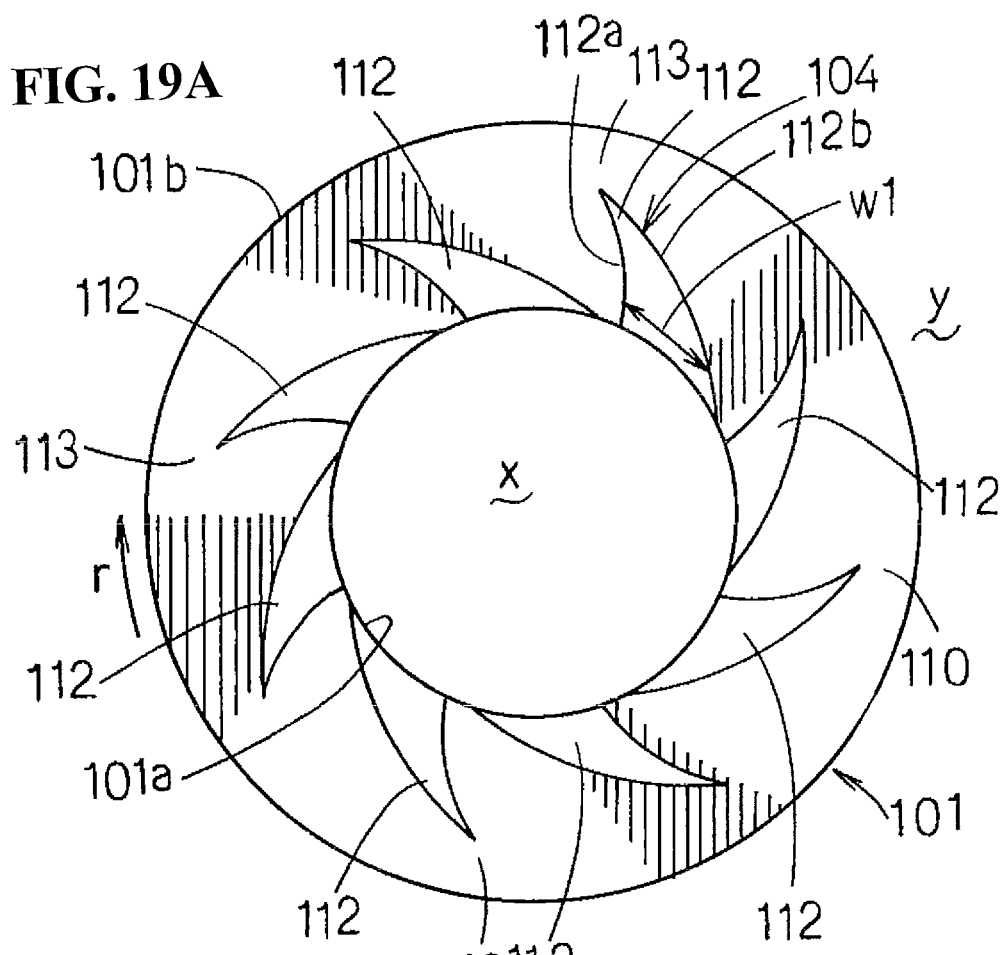
FIG. 19(A) is a plane view of a first processing member in the apparatus shown in FIG. 12(A)

The processing surfaces 110 and 120 have a mirror-polished flat part. In this embodiment, the processing surface 120 of the second processing member 102 is a flat surface subjected as a whole to mirror polishing. The processing surface 110 of the first processing member 101 is a flat surface as a whole like the second processing member 102, but has a plurality of grooves 112 ... 112 in the flat surface as shown in FIG. 19(A). The grooves 112 ... 112 while centering on the first processing member 101 in a cylindrical form extend radially toward the outer periphery of the cylinder.

The processing surfaces 110 and 120 of the first and second processing members 101 and 102 are mirror-polished such that the surface roughness Ra comes to be in the range of 0.01 µm to 1.0 µm. By this mirror polishing, Ra is regulated preferably in the range of 0.03 µm to 0.3 µm.

The material for the processing members 101 and 102 is one which is rigid and capable of mirror polishing. The rigidity of the processing members 101 and 102 is preferably at least 1500 or more in terms of Vickers hardness. A material having a low linear expansion coefficient or high thermal conductance is preferably used. This is because when the difference in coefficient of expansion between a part which generates heat upon processing and other parts is high, distortion is generated and securement of suitable clearance is influenced.

As the material for the processing members 101 and 102, it is preferable to use particularly SIC, that is, silicon carbide, SIC having a Vickers hardness of 2000 to 2500, SIC having a Vickers hardness of 3000 to 4000 coated thereon with DLC (diamond-like carbon), WC, that is, tungsten carbide having a Vickers hardness of 1800, WC coated thereon with DLC, and boron ceramics represented by $ZrB_2$, BTC and $B_4C$ having a Vickers hardness of 4000 to 5000.

The housing 106 shown in FIG. 18, the bottom of which is not shown though, is a cylinder with a bottom, and the upper part thereof is covered with the second holder 121. The second holder 121 has the second processing member 102 fixed to the lower surface thereof, and the introduction part d1 is arranged in the upper part thereof. The introduction part d1 is provided with a hopper 170 for introducing a fluid or a processed material from the outside.

Although not shown in the figure, the drive part includes a power source such as a motor and a shaft 50 that rotates by receiving power from the power source.

As shown in FIG. 18(A), the shaft 50 is arranged in the housing 106 and extends vertically. Then, the first holder 111 is arranged on the top of the shaft 50. The first holder 111 is to hold the first processing member 101 and is arranged on the shaft 50 as described above, thereby allowing the processing surface 110 of the first processing member 101 to correspond to the processing surface 120 of the second processing member 102.

The first holder 111 is a cylindrical body, and the first processing member 101 is fixed on the center of the upper surface. The first processing member 101 is fixed so as to be integrated with the first holder 111, and does not change its position relative to the first holder 111.

On the other hand, a receiving depression 124 for receiving the second processing member 102 is formed on the center of the upper surface of the second holder 121.

The receiving depression 124 has a circular cross-section. The second processing member 102 is accepted in the cylindrical receiving depression 124 so as to be concentric with the receiving depression 124.

The structure of the receiving depression 124 is similar to that in the embodiment as shown in FIG. 1(A) (the first processing member 101 corresponds to the first ring 10, the first holder 111 to the first holder 11, the second processing member 102 to the second ring 20, and the second holder 121 to the second holder 21).

Then, the second holder 121 is provided with the bias mechanism 103. The bias mechanism 103 preferably uses an elastic body such as spring. The bias mechanism 103 corresponds to the surface-approaching pressure imparting mechanism 4 in FIG. 1(A) and has the same structure. That is, the bias mechanism 103 presses that side (bottom) of the second processing member 102 which is opposite to the processing surface 120 and biases each position of the second processing member 102 uniformly downward to the first processing member 101.

On the other hand, the inner diameter of the receiving depression 124 is made larger than the outer diameter of the second processing member 102, so that when arranged concentrically as described above, a gap t1 is set between outer periphery 102b of the second processing member 102 and inner periphery of the receiving depression 124, as shown in FIG. 18(B).

Similarly, a gap t2 is set between inner periphery 102a of the second processing member 102 and outer periphery of the central portion 22 of the receiving depression 124, as shown in FIG. 18(B).

The gaps t1 and t2 are those for absorbing vibration and eccentric behavior and are set to be in a size to secure operational dimensions or more and to enable sealing. For example, when the diameter of the first processing member 101 is 100 mm to 400 mm, the gaps t1 and t2 are preferably 0.05 mm to 0.3 mm, respectively.

The first holder 111 is fixed integrally with the shaft 50 and rotated with the shaft 50. The second processing member 102 is not rotated relative to the second holder 121 by a baffle (not shown). However, for securing 0.1 µm to 10 µm clearance necessary for processing, that is, the minute gap t between the processing surfaces 110 and 120 as shown in FIG. 20(B), a gap t3 is, as shown in FIG. 18(B), arranged between the bottom of the receiving depression 124, that is, the top part, and the surface facing a top part 124a of the second processing member 102, that is, the upper part. The gap t3 is established in consideration of the clearance and the vibration and elongation of the shaft 50.

As described above, by the provision of the gaps t1 to t3, the first processing member 101, as shown in FIG. 18(B), can move not only in the direction z1 of approaching to and separating from the second processing member 102, but also in the direction z2 of inclination of the processing surface 110.

That is, in this embodiment, the bias mechanism 103 and the gaps t1 to t3 constitute a floating mechanism, and by this floating mechanism, the center and inclination of at least the second processing member 102 are made variable in the small range of several μm to several mm. The run-out and expansion of the rotary shaft and the surface vibration and vibration of the first processing member 101 are absorbed.

The groove 112 on the processing surface 110 of the first processing member 101 is described in more detail. The rear end of the groove 112 reaches the inner periphery 101a of the first processing member 101, and its top is elongated toward the outside y of the first processing member 101, that is, toward the outer periphery. As shown in FIG. 19(A), the sectional area of the groove 112 is gradually decreased in the direction from the center x of the circular first processing member 101 to the outside y of the first processing member 101, that is, toward the outer periphery.

Figure 19B:
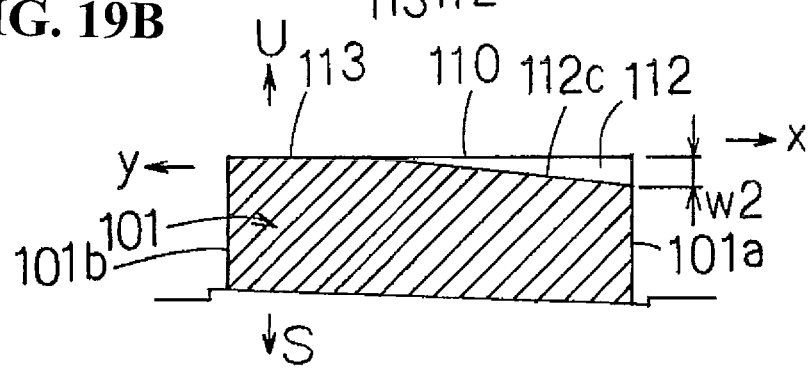
FIG. 19(B) is a schematic vertical sectional view showing an important part thereof.

The distance w1 of the left and right sides 112a and 112b of the groove 112 is decreased in the direction from the center x of the first processing member 101 to the outside y of the first processing member 101, that is, toward the outer periphery. As shown in FIG. 19(B), the depth w2 of the groove 112 is decreased in the direction from the center x of the first processing member 101 to the outside y of the first processing member 101, that is, toward the outer periphery. That is, the bottom 112c of the groove 112 is decreased in depth in the direction from the center x of the first processing member 101 to the outside y of the first processing member 101, that is, toward the outer periphery.

As described above, the groove 112 is gradually decreased both in width and depth toward the outside y, that is, toward the outer periphery, and its sectional area is gradually decreased toward the outside y. Then, the top of the groove 112, that is, the y side, is a dead end. That is, the top of the groove 112, that is, the y side does not reach the outer periphery 101b of the first processing member 101, and an outer flat surface 113 is interposed between the top of the groove 112 and the outer periphery 101b. The outer flat surface 113 is a part of the processing surface 110.

In the embodiment shown in FIG. 19, the left and right sides 112a and 112b and the bottom 112c of the groove 112 constitute a flow path limiting part. This flow path limiting part, the flat part around the groove 112 of the first processing member 101, and the flat part of the second processing member 102 constitute the dynamical pressure generating mechanism 104.

However, only one of the width and depth of the groove 112 may be constituted as described above to decrease the sectional area.

While the first processing member 101 rotates, the dynamical pressure generating mechanism 104 generates a force in the direction of separating the processing members 101 and 102 from each other to secure a desired minute space between the processing members 101 and 102 by a fluid passing through the space between the processing members 101 and 102. By generation of such dynamical pressure, a 0.1 μm to 10 μm minute space can be generated between the processing surfaces 110 and 120. A minute space like that can be regulated and selected depending on the object of processing, but is preferably 1 μm to 6 μm, more preferably 1 μm to 2 μm. This apparatus can realize a uniform mixing (uniform reaction when the mixing is accompanied by reaction) and form microparticles by the minute space, which are not achieved in the prior art.

The grooves 112 . . . 112 may extend straight from the center x to the outside y. In this embodiment, however, as shown in FIG. 19(A), the grooves 112 are curved to extend such that with respect to a rotation direction r of the first processing member 101, the center x of the groove 112 is positioned in front of the outside y of the groove 112.

In this manner, the grooves 112 . . . 112 are curved to extend so that the separation force by the dynamical pressure generating mechanism 104 can be effectively generated.

Then, the working of this apparatus is described.

As shown in FIG. 18(A), a first processed fluid R which has been introduced from a hopper 170 and has passed through the first introduction part d1, passes through the hollow part of the circular second processing member 102, and the fluid that has received the centrifugal force resulting from rotation of the first processing member 101 enters the space between the processing members 101 and 102, and uniform mixing (reaction) and, in any case, generation of microparticles are effected and processed between the processing surface 110 of the rotating first processing member 101 and the processing surface 120 of the second processing member 102, then exits from the processing members 101 and 102 and is then discharged from the discharge part 108 to the side of the decompression pump Q (hereinafter, the first processed fluid R is referred to simply as a fluid R, if necessary).

Figure 20A:
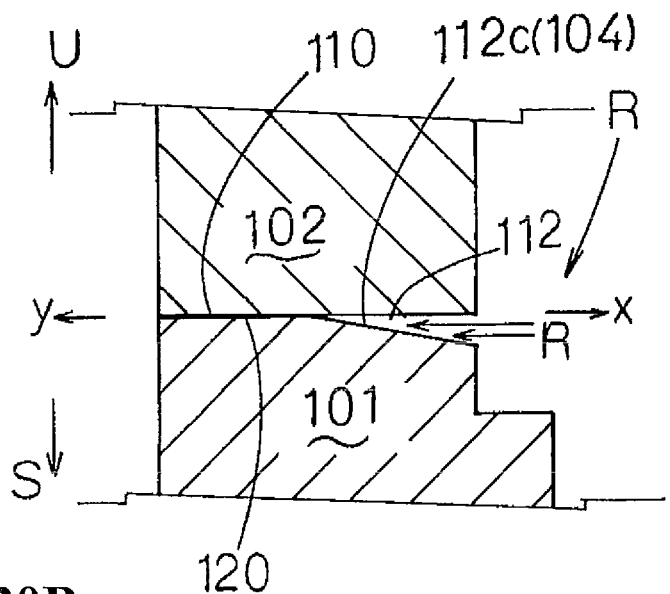
FIG. 20(A) is a vertical sectional view showing an important part of first and second processing members in the apparatus shown in FIG. 12(A)
Figure 20B:
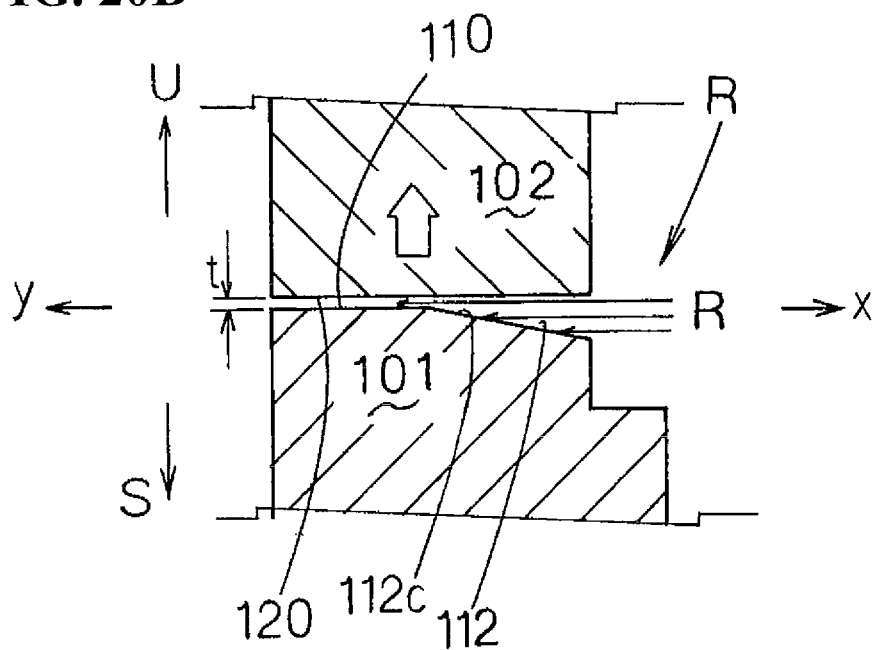
FIG. 20(B) is a vertical sectional view showing an important part of the first and second processing members with a minute gap.

In the foregoing description, the fluid R that has entered the hollow part of the circular second processing member 102 first enters the groove 112 of the rotating first processing member 101 as shown in FIG. 20(A). On the other hand, the processing surfaces 110 and 120 that are mirror-polished flat parts are kept airtight even by passing a gas such as air or nitrogen. Accordingly, even if the centrifugal force by rotation is received, the fluid R cannot enter through the groove 112 into the space between the processing surfaces 110 and 120 that are pushed against each other by the bias mechanism 103. However, the fluid R gradually runs against both the sides 112a and 112b and the bottom 112c of the groove 112 formed as a flow path limiting part to generate dynamical pressure acting in the direction of separating the processing surfaces 110 and 120 from each other. As shown in FIG. 20(B), the fluid R can thereby exude from the groove 112 to the flat surface, to secure a minute gap t, that is, clearance, between the processing surfaces 110 and 120. Then, a uniform mixing (reaction) and, in any cases, generation of microparticles are effected and processed between the mirror-polished flat surfaces. The groove 112 has been curved so that the centrifugal force is applied more accurately to the fluid to make generation of dynamical pressure more effectively.

In this manner, the fluid processing apparatus can secure a minute and uniform gap, that is, clearance, between the mirror surfaces, that is, the processing surfaces 110 and 120, by the balance between the dynamical pressure and the bias force by the bias mechanism 103. By the structure described above, the minute gap can be as superfine as 1 μm or less.

By utilizing the floating mechanism, the automatic regulation of alignment between the processing surfaces 110 and 120 becomes possible, and the clearance in each position between the processing surfaces 110 and 120 can be prevented from varying against physical deformation of each part by rotation or generated heat, and the minute gap in each position can be maintained.

In the embodiment described above, the floating mechanism is a mechanism arranged for the second holder 121 only.

Alternatively, the floating mechanism can be arranged in the first holder 111 instead of, or together with, the second holder 121.

Other embodiments of the groove 112 are shown in FIG. 21 to FIG. 23.

Figure 21A:
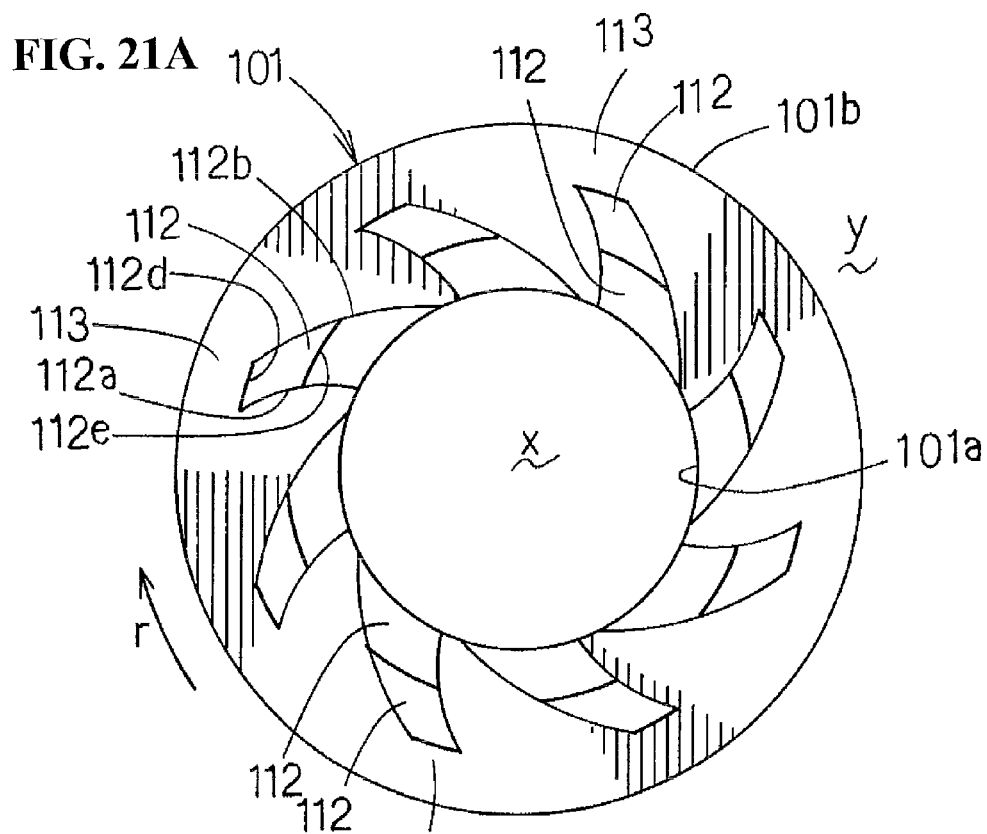
FIG. 21(A) is a plane view of another embodiment of the first processing member.
Figure 21B:
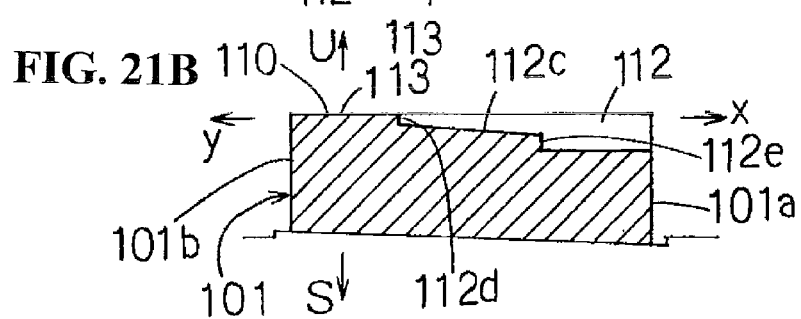
FIG. 21(B) is a vertical sectional view showing an important part thereof.

As shown in FIG. 21(A) and FIG. 21(B), the groove 112 can be provided at the top with a flat wall surface 112*d* as a part of the flow path limiting part. In the embodiment shown in FIG. 21, a step 112*e* is arranged between the first wall surface 112*d* and the inner periphery 101*a* in the bottom 112*c*, and the step 112*e* also constitutes a part of the flow path limiting part.

Figure 22A:
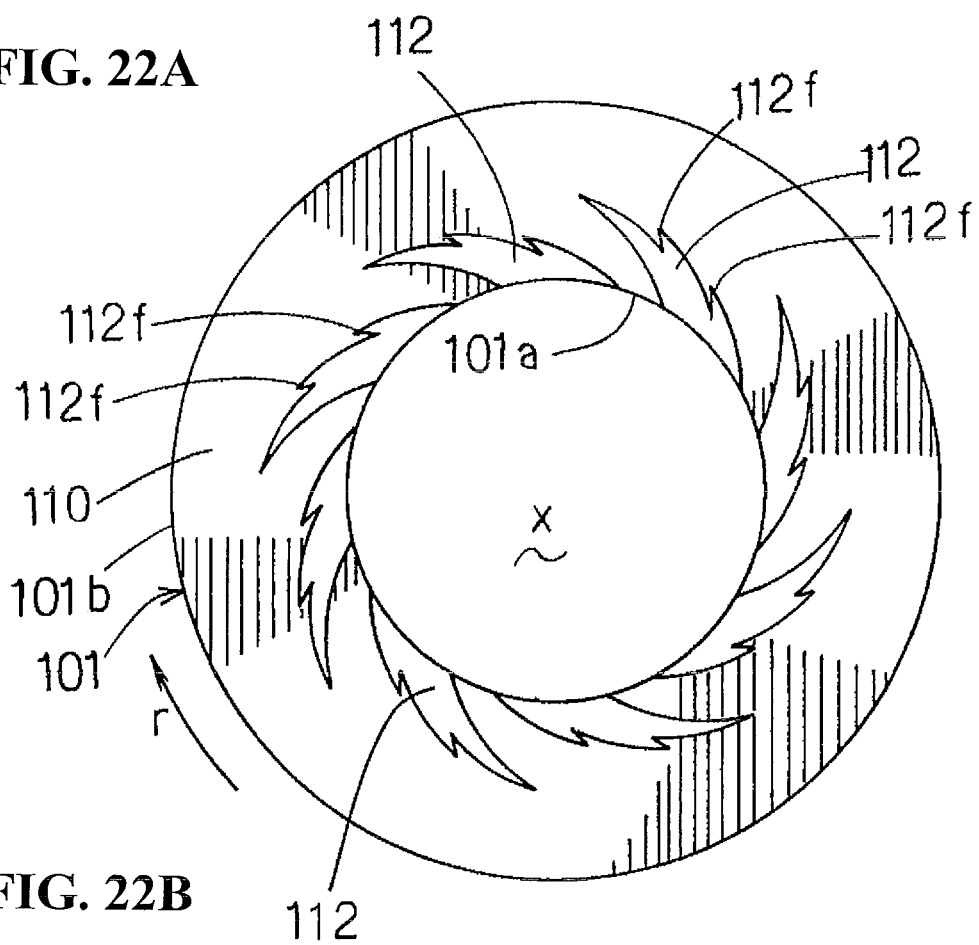
FIG. 22(A) is a plane view of still another embodiment of the first processing member.
Figure 22B:
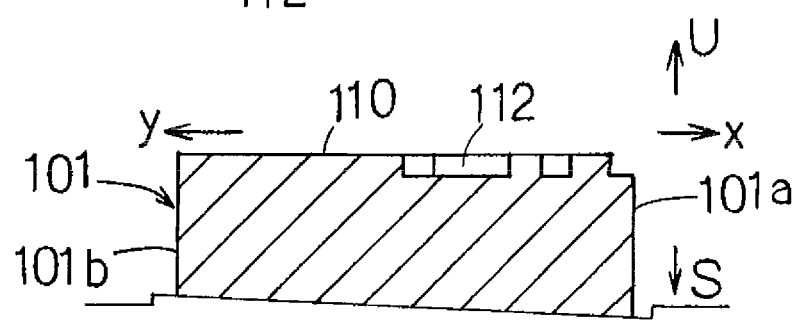
FIG. 22(B) is a vertical sectional view showing an important part thereof.

As shown in FIG. 22(A) and FIG. 22(B), the groove 112 includes a plurality of branches 112*f* . . . 112*f*, and each branch 112*f* narrows its width thereby being provided with a flow path limiting part.

With respect to the embodiments in FIG. 21 and FIG. 22, structures other than those particularly shown are similar to those of embodiments as shown in FIG. 1(A), FIG. 11(C), and FIG. 18 to FIG. 20.

In the embodiments described above, at least either the width or depth of the groove 112 is gradually decreased in size in the direction from inside to outside the first processing member 101, thereby constituting a flow path limiting part. Alternatively, as shown in FIG. 23(A) or FIG. 23(B), the groove 112 can be provided with a termination surface 112*f* without changing the width and depth of the groove 112, and the termination surface 112*f* of the groove 112 can serve as a flow path limiting part. As shown in the embodiments in FIG. 19, FIG. 21 and FIG. 22, the width and depth of the groove 112 can be changed as described above thereby slanting the bottom and both sides of the groove 112, so that the slanted surface serves as a pressure-receiving part toward the fluid to generate dynamical pressure. In the embodiment shown in FIG. 23(A) and FIG. 23(B), on the other hand, the termination surface of the groove 112 serves as a pressure-receiving part toward the fluid to generate dynamical pressure.

In the embodiment shown in FIG. 23(A) and FIG. 23(B), at least one of the width and depth of the groove 112 may also be gradually decreased in size.

The structure of the groove 112 is not limited to the one shown in FIG. 19 and FIG. 21 to FIG. 23 and can be provided with a flow path limiting part having other shapes.

For example, in the embodiments shown in FIG. 19 and FIG. 21 to FIG. 23, the groove 112 does not penetrate to the outer side of the first processing member 101. That is, there is an outer flat surface 113 between outer periphery of the first processing member 101 and the groove 112. However, the structure of the groove 112 is not limited to such embodiment, and the groove 112 may reach the outer periphery of the first processing member 101 as long as the dynamical pressure can be generated.

For example, in the case of the first processing member 101 shown in FIG. 23(B), as shown in the dotted line, a part having a smaller sectional area than other sites of the groove 112 can be formed on the outer flat surface 113.

The groove 112 may be formed so as to be gradually decreased in size in the direction from inside to outside as described above, and the part (terminal) of the groove 112 that had reached the outer periphery of the first processing member 101 may have the minimum sectional area (not shown). However, the groove 112 preferably does not penetrate to the outer periphery of the first processing member 101 as shown in FIG. 19 and FIG. 21 to FIG. 23, in order to effectively generate dynamical pressure.

Now, the embodiments shown in FIG. 18 to FIG. 23 are summarized.

This fluid processing apparatus is a processing apparatus wherein a rotating member having a flat processing surface and a fixed member having the same flat processing surface are opposite to each other so as to be concentric with each other, and while the rotating member is rotated, a raw material to be processed is fed through an opening of the fixed member and subjected to processing between the opposite flat processing surfaces of both members, wherein the rotating member is provided with a pressurizing mechanism by which pressure is generated to maintain clearance without mechanically regulating clearance and enables 1 μm to 6 μm microscopic clearance not attainable by mechanical regulation of clearance, thereby significantly improving an ability to uniformize the mixing (reaction) and in some cases, an ability to pulverize the formed particles.

That is, this fluid processing apparatus have a rotating member and a fixed member each having a flat processing surface in the outer periphery thereof and has a sealing mechanism in a plane on the flat processing surface, thereby providing a high speed rotation processing apparatus generating hydrostatic force, hydrodynamic force, or aerostatic-aerodynamic force. The force generates a minute space between the sealed surfaces, and provides a fluid processing apparatus with a function of non-contact and mechanically safe and high-level uniformization of mixing (reaction). One factor for forming this minute space is due to the rotation speed of the rotating member, and the other factor is due to a pressure difference between the introduction side and discharge side of a processed material (fluid). When a pressure imparting mechanism is arranged in the introduction side, when the pressure imparting mechanism is not arranged in the introduction side, that is, when the processed material (fluid) is introduced at atmospheric pressure, there is no pressure difference, and thus the sealed surfaces should be separated by only the rotation speed of the rotating member. This is known as hydrodynamic or aerodynamic force.

Figure 24A:
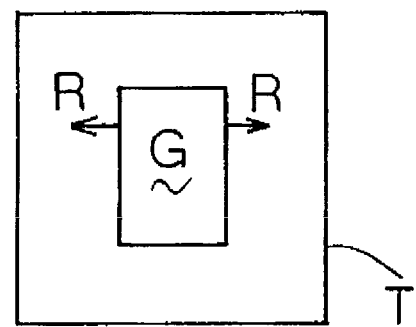
FIG. 24(A), FIG. 24(B), and FIG. 24(C) are diagrams showing embodiments other than those described above with respect to the method of separating a processed material after processing.

FIG. 18(A) shows the apparatus wherein a decompression pump Q is connected to the discharge part of the mixing apparatus G, but as described above, the mixing apparatus G may be arranged in a decompression tank T without arranging the housing 106 and the decomposition pump Q, as shown in FIG. 24(A).

In this case, the tank T is decompressed in a vacuum or in an almost vacuum, whereby the processed product formed in the mixing apparatus G is sprayed in a mist form in the tank T, and the processed material colliding with, and running down along, the inner wall of the tank T can be recovered, or a gas (vapor) separated from the processed material and filled in an upper part of the tank T, unlike the processed material running down along the wall, can be recovered to obtain the objective product after processing.

Figure 24B:
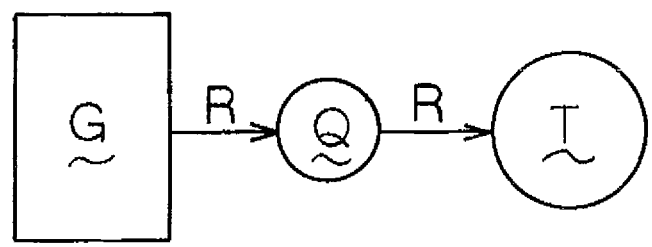

When the decompression pump Q is used, as shown in FIG. 24(B), an airtight tank T is connected via the decompression pump Q to the mixing apparatus G, whereby the processed material after processing can be formed into mist to separate and extract the objective product.

Figure 24C:
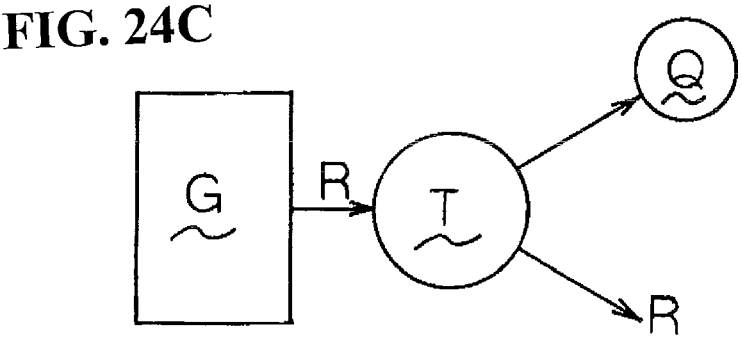

As shown in FIG. 24(C), the decompression pump Q is connected directly to the tank T, and the decompression pump Q and a discharge part for fluid R, different from the decompression pump Q, are connected to the tank T, whereby the objective product can be separated. In this case, a gasified portion is sucked by the decompression pump Q, while the fluid R (liquid portion) is discharged from the discharge part separately from the gasified portion.

In the embodiments described above, the first and second processed fluids are introduced via the second holders 21 and 121 and the second rings 20 and 102 respectively and mixed (reacted) with each other.

Now, other embodiments with respect to introduction of fluids to be processed into the apparatus are described.

As shown in FIG. 1(B), the processing apparatus shown in FIG. 1(A) is provided with a third introduction part d3 to introduce a third fluid to be processed into the space between the processing surfaces 1 and 2, and the third fluid is mixed (reacted) with the first processed fluid as well as the second processed fluid.

By the third introduction part d3, the third fluid to be mixed with the first processed fluid is fed to the space between the processing surfaces 1 and 2. In this embodiment, the third introduction part d3 is a fluid flow path arranged in the second ring 20 and is open at one end to the second processing surface 2 and has a third fluid feed part p3 connected to the other end.

In the third fluid feed part p3, a compressor or another pump can be used.

The opening of the third introduction part d3 in the second processing surface 2 is positioned outside, and more far from, the rotation center of the first processing surface 1 than the opening of the second introduction part d2. That is, in the second processing surface 2, the opening of the third introduction part d3 is located downstream from the opening of the second introduction part d2. A gap is arranged between the opening of the third introduction part d3 and the opening of the second introduction part d2 in the radial direction of the second ring 20.

With respect to structures other than the third introduction part d3, the apparatus shown in FIG. 1(B) is similar to that in the embodiment as in FIG. 1(A). In FIG. 1(B) and further in FIG. 1(C), FIG. 1(D) and FIG. 2 to FIG. 11 described later, the case 3 is omitted to simplify the drawings. In FIG. 9(B), FIG. 9(C), FIG. 10, FIG. 11(A) and FIG. 11(B), a part of the case 3 is shown.

As shown in FIG. 1(C), the processing apparatus shown in FIG. 1(B) is provided with a fourth introduction part d4 to introduce a fourth fluid to be processed into the space between the processing surfaces 1 and 2, and the fourth fluid is mixed (reacted) with the first processed fluid as well as the second and third processed fluids.

By the fourth introduction part d4, the fourth fluid to be mixed with the first processed fluid is fed to the space between the processing surfaces 1 and 2. In this embodiment, the fourth introduction part d4 is a fluid flow path arranged in the second ring 20, is open at one end to the second processing surface 2, and has a fourth fluid feed part p4 connected to the other end.

In the fourth fluid feed part p4, a compressor or another pump can be used.

The opening of the fourth introduction part d4 in the second processing surface 2 is positioned outside, and more far from, the rotation center of the first processing surface 1 than the opening of the third introduction part d3. That is, in the second processing surface 2, the opening of the fourth introduction part d4 is located downstream from the opening of the third introduction part d3.

With respect to structures other than the fourth introduction part d4, the apparatus shown in FIG. 1(C) is similar to that in the embodiment as in FIG. 1(B).

Further, five or more introduction parts further including a fifth introduction part, a sixth introduction part and the like can be arranged to mix (react) five or more fluids to be processed with one another (not shown).

As shown in FIG. 1(D), the first introduction part d1 arranged in the second holder 21 in the apparatus in FIG. 1(A) can, similarly in the second introduction part d2, be arranged in the second processing surface 2 in place of the second holder 21. In this case, the opening of the first introduction part d1 is located at the upstream side from the second introduction part d2, that is, it is positioned nearer to the rotation center than the second introduction part d2 in the second processing surface 2.

In the apparatus shown in FIG. 1(D), the opening of the second introduction part d2 and the opening of the third introduction part d3 both are arranged in the second processing surface 2 of the second ring 20. However, arrangement of the opening of the introduction part is not limited to such arrangement relative to the processing surface. Particularly as shown in FIG. 2(A), the opening of the second introduction part d2 can be arranged in a position adjacent to the second processing surface 2 in the inner periphery of the second ring 20. In the apparatus shown in FIG. 2(A), the opening of the third introduction part d3 is arranged in the second processing surface 2 similarly in the apparatus shown in FIG. 1(B), but the opening of the second introduction part d2 can be arranged inside the second processing surface 2 and adjacent to the second processing surface 2, whereby the second processed fluid can be immediately introduced onto the processing surfaces.

In this manner, the opening of the first introduction part d1 is arranged in the second holder 21, and the opening of the second introduction part d2 is arranged inside the second processing surface 2 and adjacent to the second processing surface 2 (in this case, arrangement of the third introduction part d3 is not essential), so that particularly in reaction of a plurality of processed fluids, the processed fluid introduced from the first introduction part d1 and the processed fluid introduced from the second introduction part d2 are introduced, without being reacted with each other, into the space between the processing surfaces 1 and 2, and then both the fluids can be reacted first between the processing surfaces 1 and 2. Accordingly, the structure described above is suitable for obtaining a particularly reactive processed fluid.

The term "adjacent" is not limited to the arrangement where the opening of the second introduction part d2 is contacted with the inner side of the second ring 20 as shown in FIG. 2(A). The distance between the second ring 20 and the opening of the second introduction part d2 may be such a degree that a plurality of processed fluids are not completely mixed (reacted) with one another prior to introduction into the space between the processing surfaces 1 and 2. For example, the opening of the second introduction part d2 may be arranged in a position near the second ring 20 of the second holder 21. Alternatively, the opening of the second introduction part d2 may be arranged on the side of the first ring 10 or the first holder 11.

In the apparatus shown in FIG. 1(B), a gap is arranged between the opening of the third introduction part d3 and the opening of the second introduction part d2 in the radial direction of the second ring 20, but as shown in FIG. 2(B), the second and third processed fluids can be introduced into the space between the processing surfaces 1 and 2, without providing such gap, thereby immediately joining both the fluids together. The apparatus shown in FIG. 2(B) can be selected depending on the object of processing.

In the apparatus shown in FIG. 1(D), a gap is also arranged between the opening of the first introduction part d1 and the opening of the second introduction part d2 in the radial direction of the second ring 20, but the first and second processed fluids can be introduced into the space between the processing surfaces 1 and 2, without providing such gap, thereby immediately joining both the fluids together (not shown). Such arrangement of the opening can be selected depending on the object of processing.

In the embodiment shown in FIG. 1(B) and FIG. 1(C), the opening of the third introduction part d3 is arranged in the second processing surface 2 downstream from the opening of the second introduction part d2, in other words, outside the opening of the second introduction part d2 in the radial direction of the second ring 20. Alternatively, as shown in FIG. 2(C) and FIG. 3(A), the opening of the third introduction part d3 and the opening of the second introduction part d2 can be arranged in the second processing surface 2 in positions different in a circumferential direction r0 of the second ring 20. In FIG. 3, numeral m1 is the opening (first opening) of the first introduction part d1, numeral m2 is the opening (second opening) of the second introduction part d2, numeral m3 is the opening (third opening) of the third introduction part d3, and numeral r1 is the radical direction of the ring.

When the first introduction part d1 is arranged in the second ring 20, as shown in FIG. 2(D), the opening of the first introduction part d1 and the opening of the second introduction part d2 can be arranged in the second processing surface 2 in positions different in the circumferential direction of the second ring 20.

Figure 3B:
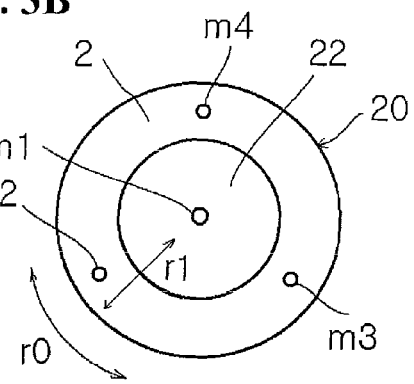
FIG. 3(B) is a schematic bottom view showing an important part of another embodiment of the apparatus.
Figure 3C:
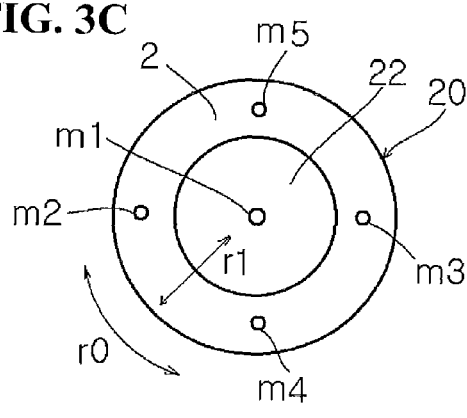
FIG. 3(C) is a schematic bottom view showing an important part of still another embodiment of the apparatus.

In the apparatus shown in FIG. 3(A), the openings of two introduction parts are arranged in the second processing surface 2 of the second ring 20 in positions different in the circumferential direction r0, but as shown in FIG. 3(B), the openings of three introduction parts can be arranged in positions different in the circumferential direction r0 of the ring, or as shown in FIG. 3(C), the openings of four introduction parts can be arranged in positions different in the circumferential direction r0 of the ring. In FIG. 3(B) and FIG. 3(C), numeral m4 is the opening of the fourth introduction part, and in FIG. 3(C), numeral m5 is the opening of the fifth introduction part. Five or more openings of introduction parts may be arranged in positions different in the circumferential direction r0 of the ring (not shown).

In the apparatuses shown in above, the second to fifth introduction parts can introduce different fluids, that is, the second, third, fourth and fifth fluids. On the other hand, the second to fifth openings m2 to m5 can introduce the same fluid, that is, the second fluid into the space between the processing surfaces. In this case, the second to fifth introduction parts are connected to the inside of the ring and can be connected to one fluid feed part, that is, the second fluid feed part p2 (not shown).

A plurality of openings of introduction parts arranged in positions different in the circumferential direction r0 of the ring can be combined with a plurality of openings of introduction parts arranged in positions different in the radial direction r1 of the ring.

Figure 3D:
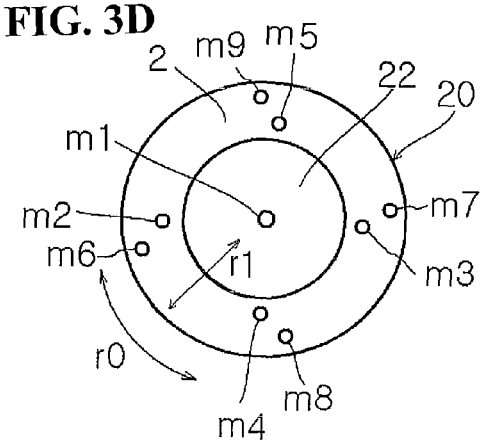
FIG. 3(D) is a schematic bottom view showing the concept of still another embodiment of the apparatus.

For example, as shown in FIG. 3(D), the openings m2 to m9 of eight introduction parts are arranged in the second processing surface 2, wherein four openings m2 to m5 of them are arranged in positions different in the circumferential direction r0 of the ring and identical in the radial direction r1 of the ring, and the other four openings m6 to m9 are arranged in positions different in the circumferential direction r0 of the ring and identical in the radial direction r1 of the ring. Then, the other openings m6 to m9 are arranged outside the radial direction r of the four openings m2 to m5. The outside openings and inside openings may be arranged in positions identical in the circumferential direction r0 of the ring, but in consideration of rotation of the ring, may be arranged in positions different in the circumferential direction r0 of the ring as shown in FIG. 3(D). In this case too, the openings are not limited to the arrangement and number shown in FIG. 3(D).

Figure 3E:
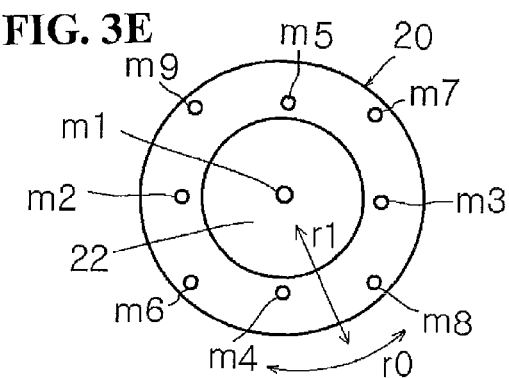
FIG. 3(E) is a schematic bottom view showing the concept of still another embodiment of the apparatus.

For example, as shown in FIG. 3(E), the outside opening in the radial direction can be arranged in the apex of a polygon, that is, in the apex of a rectangle in this case, and the inside opening in the radial direction can be positioned on one side of the rectangle. As a matter of course, other arrangements can also be used.

Figure 3F:
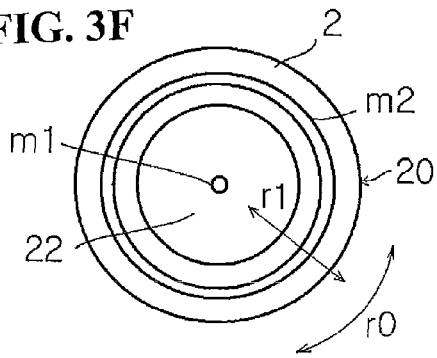
FIG. 3(F) is a schematic bottom view showing the concept of still another embodiment of the apparatus.

When the openings other than the first opening m1 feed the second processed fluid into the space between the processing surfaces, each of the openings may be arranged as continuous openings in the circumferential direction r0 as shown in FIG. 3(F), instead of being arranged discretely in the circumferential direction r0 of the processing surface.

Figure 4A:
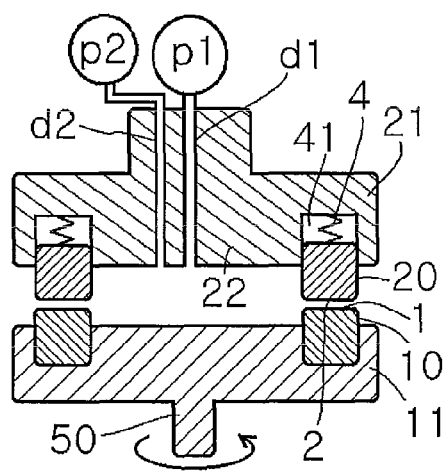
FIG. 4(A) to FIG. 4(D) each show a schematic vertical sectional view showing the concept of still another embodiment of the apparatus shown in FIG. 1.
Figure 4B:
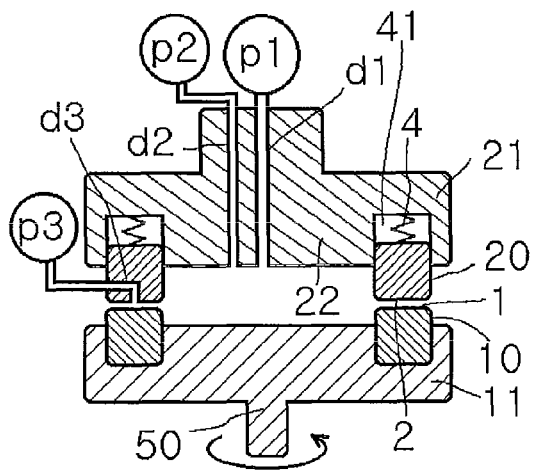
Figure 4C:
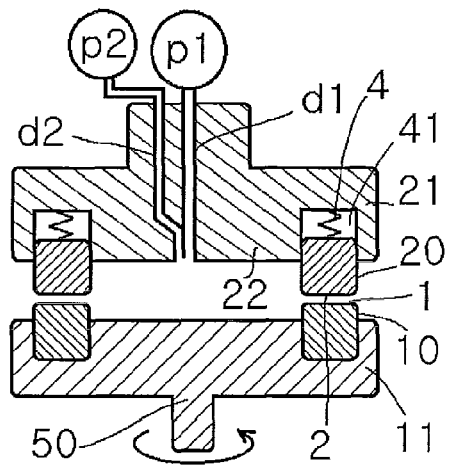
Figure 4D:
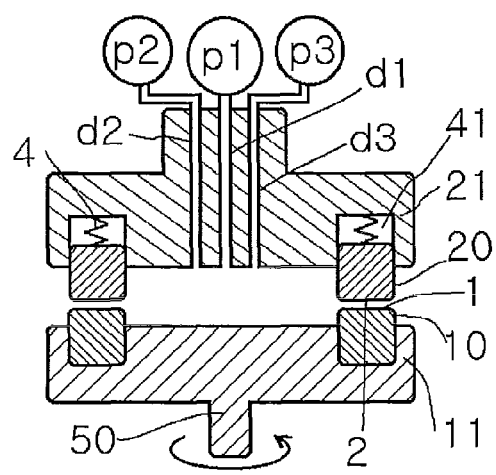

As shown in FIG. 4(A), depending on the object of processing, the second introduction part d2 arranged in the second ring 20 in the apparatus shown in FIG. 1(A) can be, similar to the first introduction part d1, arranged in the central portion 22 of the second holder 21. In this case, the opening of the second introduction part d2 is positioned with a gap outside the opening of the first introduction part d1 positioned in the center of the second ring 20. As shown in FIG. 4(B), in the apparatus shown in FIG. 4(A), the third introduction part d3 can be arranged in the second ring 20. As shown in FIG. 4(C), in the apparatus shown in FIG. 4(A), the second and third processed fluids can be introduced into the space inside the second ring 20 without arranging a gap between the opening of the first introduction part d1 and the opening of the second introduction part d2, so that both the fluids can immediately join together. As shown in FIG. 4(D), depending on the object of processing, in the apparatus shown in FIG. 4(A), the third introduction part d3 can be, similar to the second introduction part d2, arranged in the second holder 21. Four or more introduction parts may be arranged in the second holder 21 (not shown).

Figure 5A:
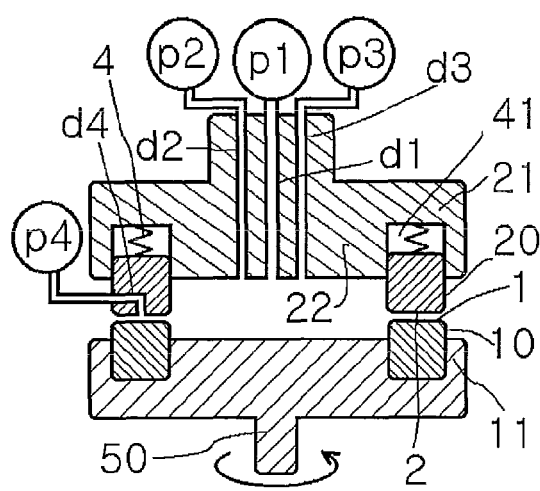
FIG. 5(A) to FIG. 5(D) each show a schematic vertical sectional view showing the concept of still another embodiment of the apparatus shown in FIG. 1.

As shown in FIG. 5(A), depending on the object of processing, in the apparatus shown in FIG. 4(D), the fourth introduction part d4 can be arranged in the second ring 20, so that the fourth processed fluid may be introduced into the space between the processing surfaces 1 and 2.

Figure 5B:
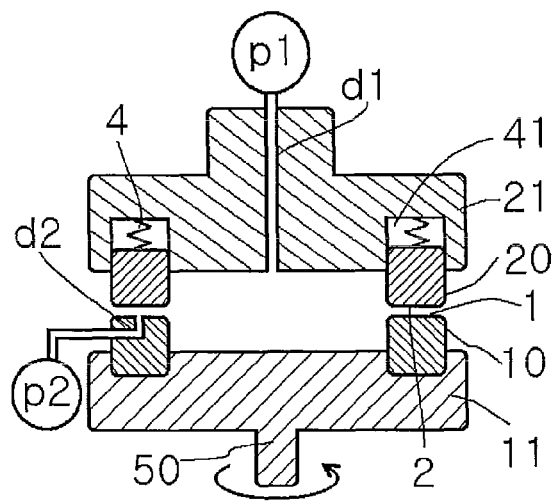

As shown in FIG. 5(B), in the apparatus shown in FIG. 1(A), the second introduction part d2 can be arranged in the first ring 10, and the opening of the second introduction part d2 can be arranged in the first processing surface 1.

Figure 5C:
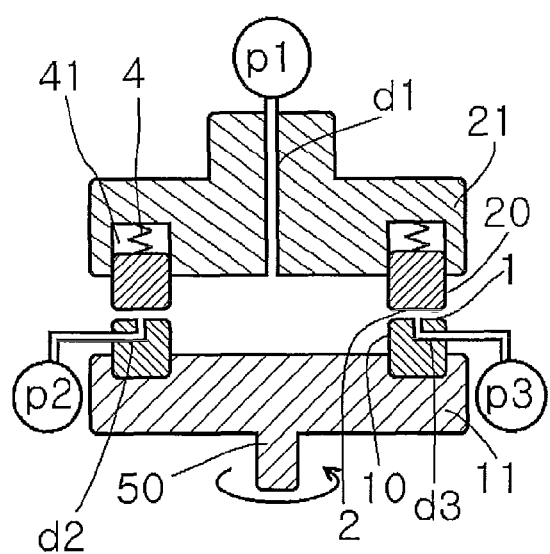

As shown in FIG. 5(C), in the apparatus shown in FIG. 5(B), the third introduction part d3 can be arranged in the first ring 10, and the opening of the third introduction part d3 and the opening of the second introduction part d2 can be arranged in the first processing surface 1 in positions different in the circumferential direction of the first ring 10.

Figure 5D:
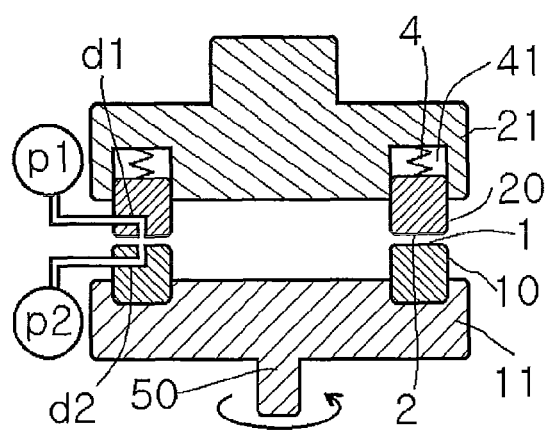

As shown in FIG. 5(D), in the apparatus shown in FIG. 5(B), the first introduction part d1 can be arranged in the second ring 20 instead of arranging the first introduction part d1 in the second holder 21, and the opening of the first introduction part d1 can be arranged in the second processing surface 2. In this case, the openings of the first and second introduction parts d1 and d2 are arranged in positions identical in the radial direction of the ring.

Figure 6A:
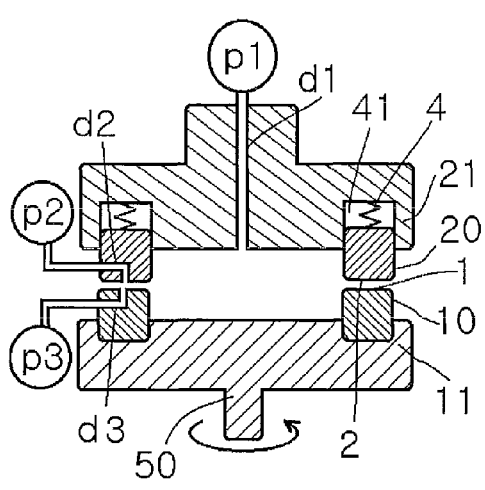
FIG. 6(A) to FIG. 6(D) each show a schematic vertical sectional view showing the concept of still another embodiment of the apparatus shown in FIG. 1.

As shown in FIG. 6(A), in the apparatus shown in FIG. 1(A), the third introduction part d3 can be arranged in the first ring 10, and the opening of the third introduction part d3 can be arranged in the first processing surface 1. In this case, both the openings of the second and third introduction parts d2 and d3 are arranged in positions identical in the radial direction of the ring. However, both the openings may be arranged in positions different in the radial direction of the ring.

Figure 6B:
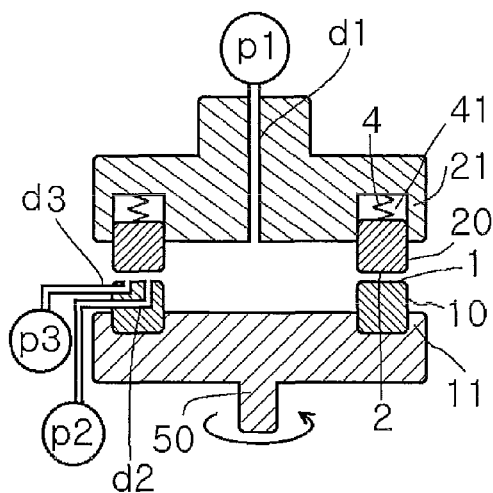

In the apparatus shown in FIG. 5(C), both the openings of the second and third introduction parts d2 and d3 are arranged in positions identical in the radial direction of the first ring 10 and simultaneously arranged in positions different in the circumferential direction (that is, rotation direction) of the first ring 10, however in this apparatus, as shown in FIG. 6(B), both the openings of the second and third introduction parts d2 and d3 can be arranged in positions identical in the circumferential direction of the first ring 10 and simultaneously arranged in positions different in the radical direction of the first ring 10. In this case, as shown in FIG. 6(B), a gap can be arranged between both the openings of the second and third introduction parts d2 and d3 in the radial direction of the first ring 10, or without arranging the gap, the second and third processed fluids may immediately join together (not shown).

Figure 6C:
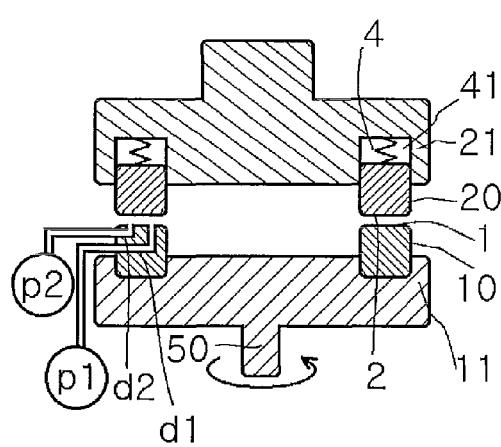

As shown in FIG. 6(C), the first introduction part d1 together with the second introduction part d2 can be arranged in the first ring 10 instead of arranging the first introduction part d1 in the second holder 21. In this case, in the first processing surface 1, the opening of the first introduction part d1 is arranged upstream (inside the radial direction of the first ring 11) from the opening of the second introduction part d2. A gap is arranged between the opening of the first introduction part d1 and the opening of the second introduction part d2 in the radial direction of the first ring 11. Alternatively, such gap may not be arranged (not shown).

Figure 6D:
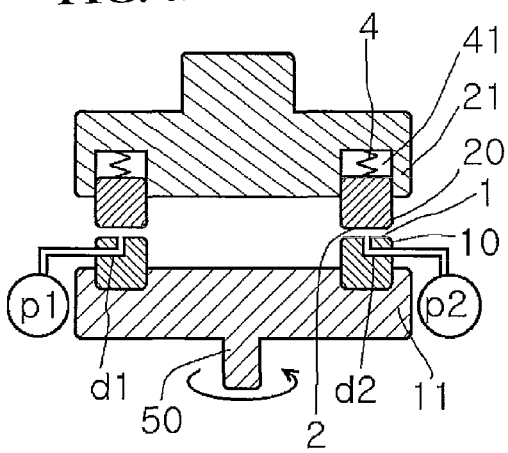

As shown in FIG. 6(D), both the openings of the first introduction part d1 and the second introduction part d2 can be arranged in positions different in the circumferential direction of the first ring 10 in the first processing surface 1 in the apparatus shown in FIG. 6(C).

In the embodiment shown in FIG. 6(C) and FIG. 6(D), three or more introduction parts may be arranged in the first ring 10, and in the second processing surface 2, so the respective openings may be arranged in positions different in the circumferential direction or in positions different in the radial direction of the ring (not shown). For example, the arrangement of openings in the second processing surface 2, shown in FIG. 3(B) to FIG. 3(F), can also be used in the first processing surface 1.

Figure 7A:
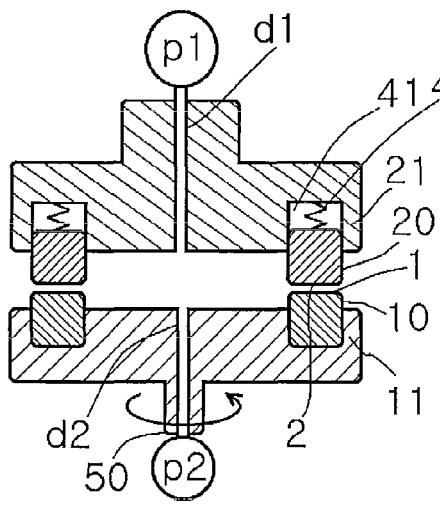
FIG. 7(A) to FIG. 7(D) each show a schematic vertical sectional view showing the concept of still another embodiment of the apparatus shown in FIG. 1.

As shown in FIG. 7(A), in the apparatus shown in FIG. 1(A), the second introduction part d2 can be arranged in the first holder 11 instead of arranging the part d2 in the second ring 20. In this case, the opening of the second introduction part d2 is arranged preferably in the center of the central shaft of rotation of the first ring 10, in the site surrounded with the first ring 10 on the upper surface of the first holder 11.

Figure 7B:
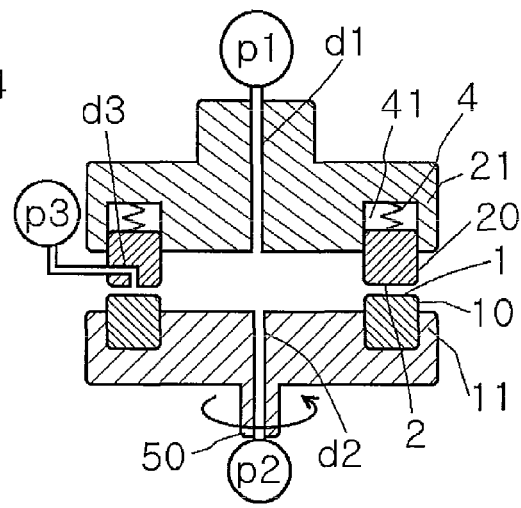

As shown in FIG. 7(B), in the embodiment shown in FIG. 7(A), the third introduction part d3 can be arranged in the second ring 20, and the opening of the third introduction part d3 can be arranged in the second processing surface 2.

Figure 7C:
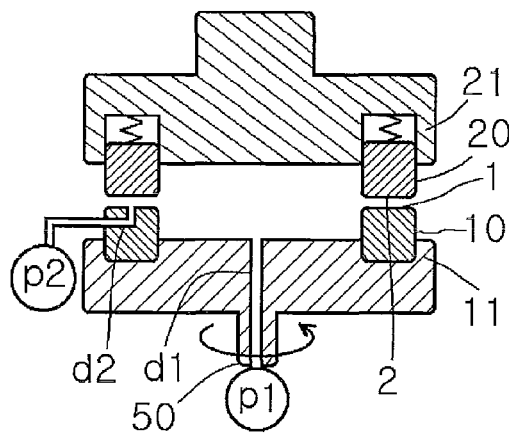

As shown in FIG. 7(C), the first introduction part d1 can be arranged in the first holder 11 instead of arranging the part d1 in the second holder 21. In this case, the opening of the first introduction part d1 is arranged preferably in the central shaft of rotation of the first ring 10, in the site surrounded with the first ring 10 on the upper surface of the first holder 11. In this case, as shown in the figure, the second introduction part d2 can be arranged in the first ring 10, and its opening can be arranged in the first processing surface 1. In this case, the second introduction part d2 can be arranged in the second ring 20, and its opening can be arranged in the second processing surface 2 (not shown).

Figure 7D:
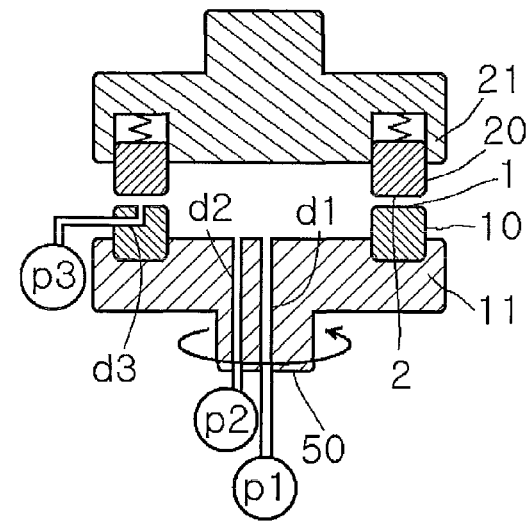

As shown in FIG. 7(D), the second introduction part d2 shown in FIG. 7(C) together with the first introduction part d1 can be arranged in the first holder 11. In this case, the opening of the second introduction part d2 is arranged in the site surrounded with the first ring 10 on the upper surface of the first holder 11. In this case, the second introduction part d2 arranged in the second ring 20 may serve as the third introduction part d3 in FIG. 7(C).

Figure 8A:
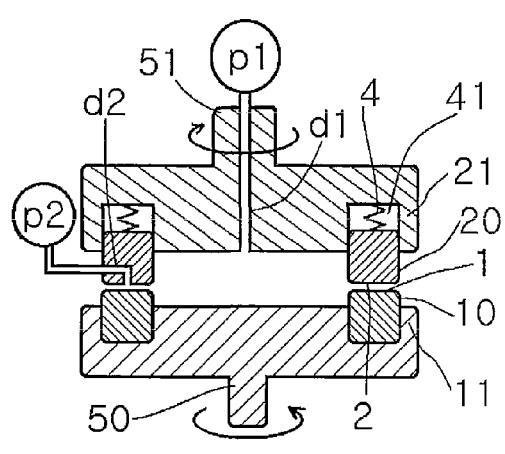
FIG. 8(A) to FIG. 8(D) each show a schematic vertical sectional view showing the concept of still another embodiment of the apparatus shown in FIG. 1.

In the embodiments shown in FIG. 1 to FIG. 7, the first holder 11 and the first ring 10 are rotated relative to the second holder 21 and the second ring 20, respectively. As shown in FIG. 8(A), in the apparatus shown in FIG. 1(A), the second holder 2 may be provided with a rotary shaft 51 rotating with the turning force from the rotation drive member, to rotate the second holder 21 in a direction opposite to the first holder 11. The rotation drive member in the rotary shaft 51 may be arranged separately from the one for rotating the rotary shaft 50 of the first holder 11 or may receive power from the drive part for rotating the rotary shaft 50 of the first holder 11 by a power transmission means such as a gear. In this case, the second holder 2 is formed separately from the case, and shall, like the first holder 11, be rotatably accepted in the case.

Figure 8B:
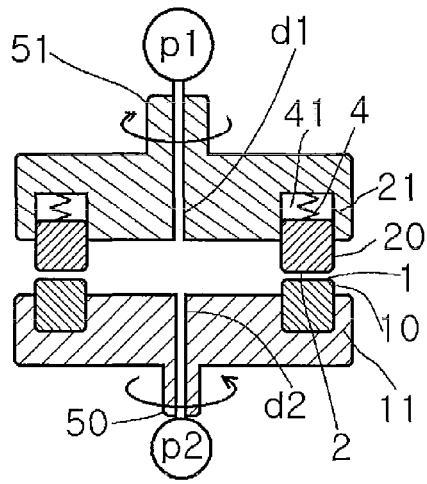

As shown in FIG. 8(B), in the apparatus shown in FIG. 8(A), the second introduction part d2 can be, similarly in the apparatus in FIG. 7(B), arranged in the first holder 11 in place of the second ring 20.

Figure 8C:
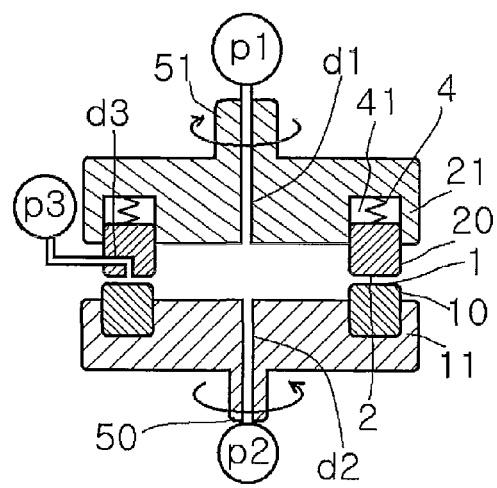

In the apparatus shown in FIG. 8(B), the second introduction part d2 can be arranged in the second holder 21 in place of the first holder 11 (not shown). In this case, the second introduction part d2 is the same as one in the apparatus in FIG. 4(A). As shown in FIG. 8(C), in the apparatus shown in FIG. 8(B), the third introduction part d3 can be arranged in the second ring 20, and the opening of the third introduction part d3 can be arranged in the second processing surface 2.

Figure 8D:
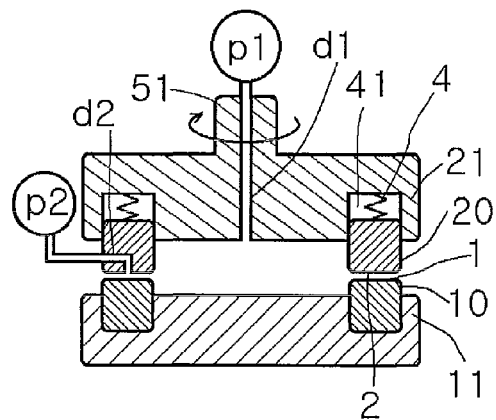

As shown in FIG. 8(D), the second holder 21 only can be rotated without rotating the first holder 11. Even in the apparatuses shown in FIG. 1(B) to FIG. 7, the second holder 21 together with the first holder 11, or the second holder 21 alone, can be rotated (not shown).

Figure 9A:
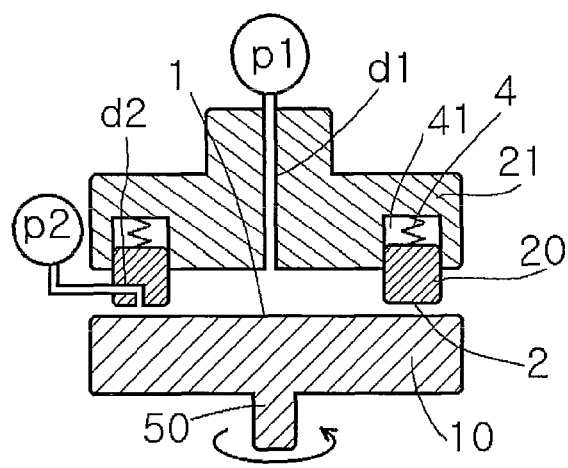
FIG. 9(A) to FIG. 9(C) each show a schematic vertical sectional view showing the concept of still another embodiment of the apparatus shown in FIG. 1.

As shown in FIG. 9(A), the second processing member 20 is a ring, while the first processing member 10 is not a ring and can be a rotating member provided directly with a rotary shaft 50 like that of the first holder 11 in other embodiments. In this case, the upper surface of the first processing member 10 serves as the first processing surface 1, and the processing surface is an evenly flat surface which is not circular (that is, hollow-free). In the apparatus shown in FIG. 9(A), similarly in the apparatus in FIG. 1(A), the second introduction part d2 is arranged in the second ring 20, and its opening is arranged in the second processing surface 2.

Figure 9B:
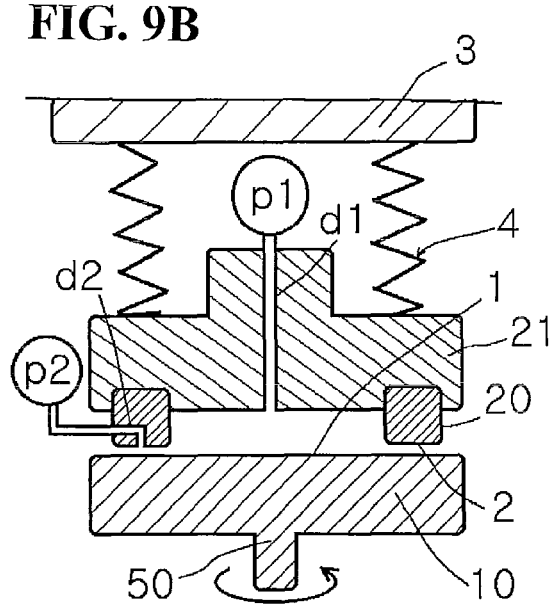
Figure 9C:
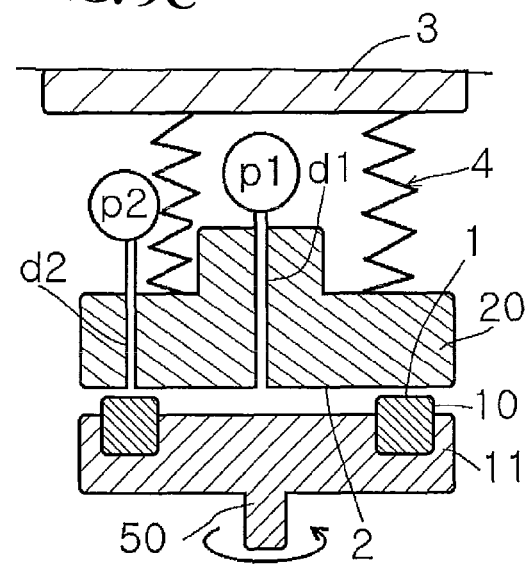
Figure 10A:
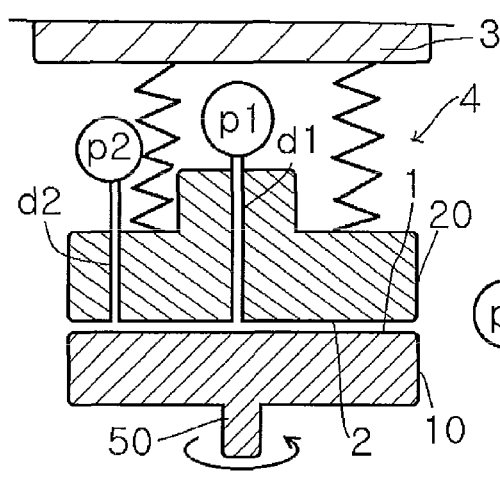
FIG. 10(A) to FIG. 10(D) each show a schematic vertical sectional view showing the concept of still another embodiment of the apparatus shown in FIG. 1.

As shown in FIG. 9(B), in the apparatus shown in FIG. 9(A), the second holder 21 is independent of the case 3, and a surface-approaching pressure imparting mechanism 4 such as an elastic body for approaching to and separating from the first processing member 10 provided with the second ring 20 can be provided between the case 3 and the second holder 21. In this case, as shown in FIG. 9(C), the second processing member 20 is not a ring, but is a member corresponding to the second holder 21, and the lower surface of the member can serve as the second processing surface 2. As shown in FIG. 10(A), in the apparatus shown in FIG. 9(C), the first processing member 10 is not a ring either, and in other embodiments similar to the apparatus shown in FIG. 9(A) and FIG. 9(B), the site corresponding to the first holder 11 can serve as the first processing member 10, and its upper surface can serve as the first processing surface 1.

In the embodiments described above, at least the first fluid is supplied from the first processing member 10 and the second processing member 20, that is, from the central part of the first ring 10 and the second ring 20, and after processing (mixing (reaction)) of the other fluids, the processed fluid is discharged to the outside in the radial direction.

Figure 10B:
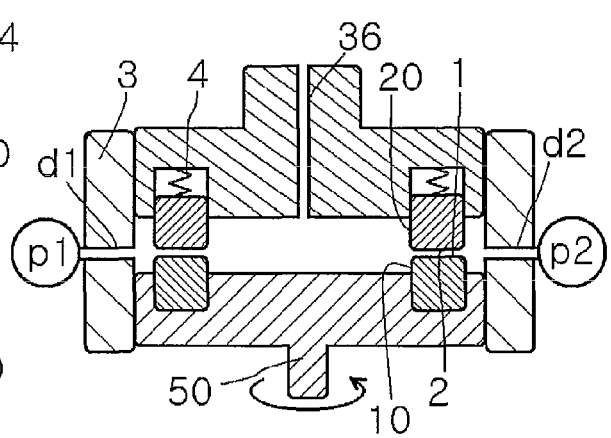

Alternatively, as shown in FIG. 10(B), the first fluid can be supplied in the direction from the outside to the inside of the first ring 10 and second ring 20. In this case, the outside of the first holder 11 and the second holder 21 is sealed with the case 3, the first introduction part d1 is arranged directly in the case 3, and the opening of the introduction part is arranged in a site inside the case and corresponding to the abutting position of the rings 10 and 20, as shown in the figure. In the apparatus in FIG. 1(A), a discharge part 36 is arranged in the position in which the first introduction part d1 is arranged, that is, in the central position of the ring 1 of the first holder 11. The opening of the second introduction part d2 is arranged in the opposite side of the opening of the case behind the central shaft of rotation of the holder. However, the opening of the second introduction part d may be, similar to the opening of the first introduction part d1, arranged in a site inside the case and corresponding to the abutting position of the rings 10 and 20. As described above, the embodiment is not limited to the one where the opening of the second introduction part d is formed to the opposite side of the opening of the first introduction part d1.

In this case, the outside of the diameter of both the rings 10 and 20 is on the upstream side, and the inside of both the rings 10 and 20 is on the downstream side.

As such, as shown in FIG. 16(E), when the processed fluid moves from outside to inside, the first processing surface 1 of the first processing member 10 may also be provided with groove-like depressions 13 . . . 13 extending in the direction from outside to inside of the first processing member 10. When the groove-like depressions 13 . . . 13 are formed, the balance ratio K described above is preferably set as 100% or more of unbalance type. As a result, dynamical pressure is generated in the groove-like depressions 13 . . . 13 upon rotating, the first and second processing surfaces 1 and 2 can rotate in a surely non-contact state, so that the risk of abrasion and the like due to contact can be eliminated. In the embodiment shown in FIG. 16(E), the separating force due to the pressure of the processed fluid is generated in an inner end 13a of the depressions 13.

Figure 10C:
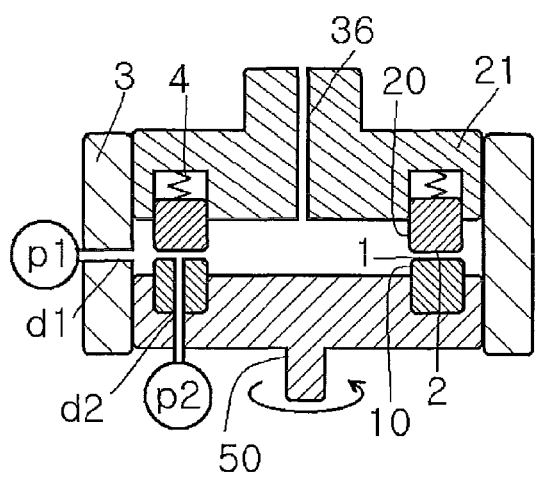
Figure 10D:
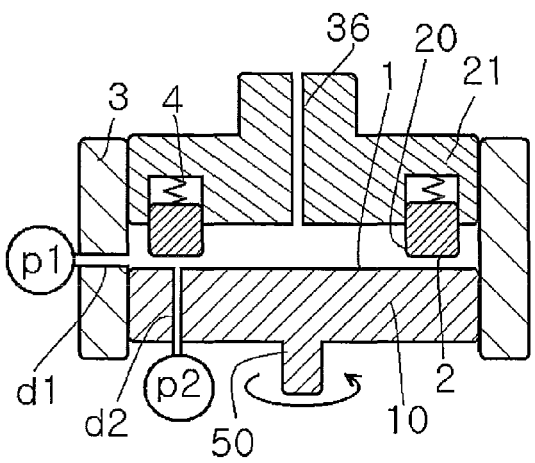

As shown in FIG. 10(C), in the apparatus shown in FIG. 10(B), the second introduction part d2, which is arranged in the side of the case 3, can be arranged in the first ring 11 in space of the mentioned position, and its opening can be arranged in the first processing surface 1. In this case, as shown in FIG. 10(D), the first processing member 10 is not formed as a ring. Similarly in the apparatuses shown in FIG. 9(A), FIG. 9(B) and FIG. 10(A), in other embodiments, the site corresponding to the first holder 11 is the first processing member 10, its upper surface being the first processing surface 1, the second introduction part d2 being arranged in the first processing member 10, and its opening may be arranged in the first processing surface 1.

Figure 11A:
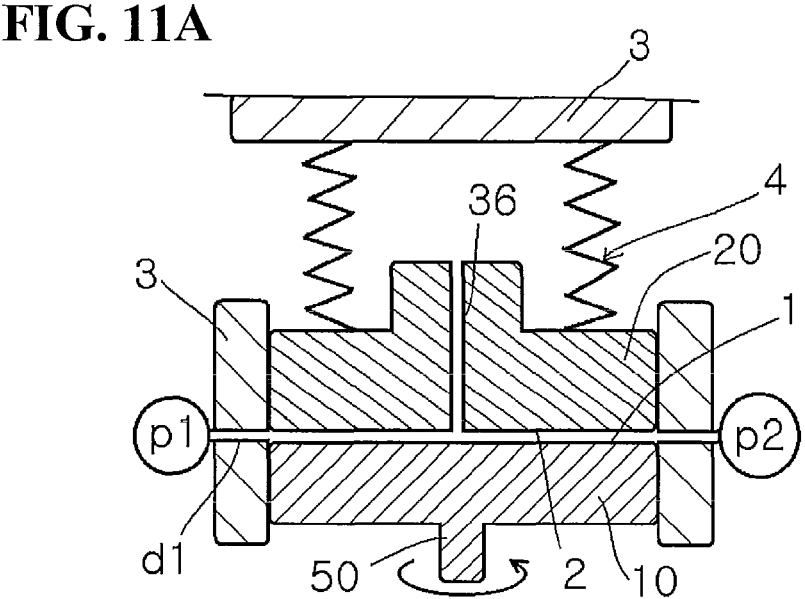
FIG. 11(A) and FIG. 11(B) each show a schematic vertical sectional view showing the concept of still another embodiment of the apparatus shown in FIG. 1.

As shown in FIG. 11(A), in the apparatus shown in FIG. 10(D), the second processing member 20 is not formed as a ring, and in other embodiments, the member corresponding to the second holder 21 serves as the second processing member 20, and its lower surface serves as the second processing surface 2. Then, the second processing member 20 is a member independent of the case 3, and the same surface-approaching pressure imparting mechanism 4 as one in the apparatuses shown in FIG. 9(B), FIG. 9(C) and FIG. 10(A) can be arranged between the case 3 and the second processing member 20.

Figure 11B:
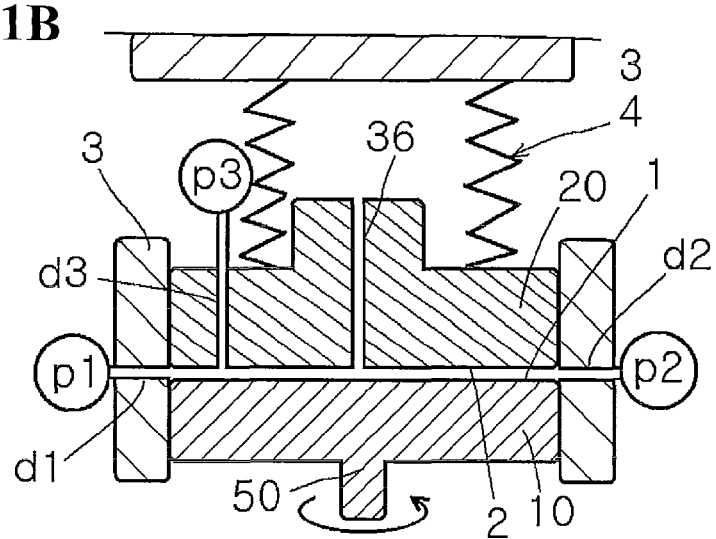
Figure 11C:
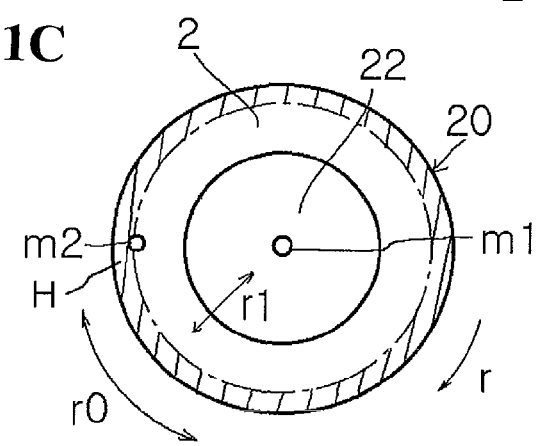
FIG. 11(C) is a schematic bottom view showing an important part of the apparatus shown in FIG. 1(A).

As shown in FIG. 11(B), the second introduction part d2 in the apparatus shown in FIG. 11(A) serves as the third introduction part d3, and separately the second introduction part d2 can be arranged. In this case, the opening of the second introduction part d2 is arranged downstream from the opening of the third introduction part d3 in the second processing surface 2.

In the apparatuses shown in FIG. 4 and the apparatuses shown in FIG. 5(A), FIG. 7(A), FIG. 7(B), FIG. 7(D), FIG. 8(B) and FIG. 8(C), other processed fluids flow into the first processed fluid before reaching the processing surfaces 1 and 2, and these apparatuses are not suitable for the fluid which is rapidly crystallized or separated. However, these apparatuses can be used for the fluid having a low reaction speed.

The fluid processing apparatus suitable for carrying out the method according to the present invention is summarized as follows.

As described above, the fluid processing apparatus comprises a fluid pressure imparting mechanism that imparts predetermined pressure to a processed fluid, at least two processing members, that is, a first processing member 10 arranged in a sealed fluid flow path through which a processed fluid at the predetermined pressure flows and a second processing member 20 capable of approaching to and separating from the first processing member 10, at least two processing surfaces of a first processing surface 1 and a second processing surface 2 arranged in a position in which they are faced with each other in the processing members 10 and 20, and a rotation drive mechanism that relatively rotates the first processing member 10 and the second processing member 20, wherein at least two processed fluids are mixed (and reacted when the mixing is accompanied by reaction) between the processing surfaces 1 and 2. Of the first processing member 10 and the second processing member 20, at least the second processing member 20 has a pressure-receiving surface, at least a part of the pressure-receiving surface is comprised of the second processing surface 2, and the pressure-receiving surface receives pressure applied by the fluid pressure imparting mechanism to at least one of the fluids to generate a force to move in the direction of separating the second processing surface 2 from the first processing surface 1. In this apparatus, the processed fluid that has received said pressure passes through the space between the first processing surface 1 and the second processing surface 2 capable of approaching to and separating from each other, thereby generating a desired mixing (reaction) between the processed fluids with the processed fluids being passed between the processing surfaces 1 and 2 and forming a fluid film of predetermined thickness.

In this fluid processing apparatus, at least one of the first processing surface 1 and the second processing surface 2 is preferably provided with a buffer mechanism for regulation of micro-vibration and alignment.

In this processing apparatus, one of or both the first processing surface 1 and the second processing surface 2 is preferably provided with a displacement regulating mechanism capable of regulating the displacement in the axial direction caused by abrasion or the like thereby maintaining the thickness of a fluid film between the processing surfaces 1 and 2.

In this fluid processing apparatus, a pressure device such as a compressor for applying predetermined feeding pressure to a fluid can be used as the fluid pressure imparting mechanism.

As the pressure device, a device capable of regulating an increase and decrease in feeding pressure is used. This is because the pressure device should be able to keep established pressure constant and should be able to regulate an increase and decrease in feeding pressure as a parameter to regulate the distance between the processing surfaces.

The fluid processing apparatus can be provided with a separation preventing part for defining the maximum distance between the first processing surface 1 and the second processing surface 2 and preventing the processing surfaces 1 and 2 from separating from each other by the maximum distance or more.

The fluid processing apparatus can be provided with an approach preventing part for defining the minimum distance between the first processing surface 1 and the second processing surface 2 and preventing the processing surfaces 1 and 2 from approaching to each other by the minimum distance or less.

The fluid processing apparatus can be one wherein both the first processing surface 1 and the second processing surface 2 are rotated in opposite directions.

The fluid processing apparatus can be provided with a temperature-regulating jacket for regulating the temperature of either or both of the first processing surface 1 and the second processing surface 2.

The fluid processing apparatus is preferably one wherein at least a part of either or both of the first processing surface 1 and the second processing surface 2 is mirror-polished.

The fluid processing apparatus can be one wherein one of or both the first processing surface 1 and the second processing surface 2 is provided with depressions.

The fluid processing apparatus preferably includes, as a means for feeding one processed fluid to be mixed (reacted) with another processed fluid, a separate introduction path independent of a path for another processed fluid, at least one of the first processing surface and the second processing surface is provided with an opening leading to the separate introduction path, and another processed fluid sent through the separate introduction path is introduced into the processed fluid.

The fluid processing apparatus for carrying out the present invention comprises a fluid pressure imparting mechanism that imparts predetermined pressure to a fluid, at least two processing surfaces of a first processing surface 1 and a second processing surface 2 capable of approaching to and separating from each other which are connected to a sealed fluid flow path through which the processed fluid at the predetermined pressure is passed, a surface-approaching pressure imparting mechanism that imparts surface-approaching pressure to the space between the processing surfaces 1 and 2, and a rotation drive mechanism that relatively rotates the first processing surface 1 and the second processing surface 2, whereby at least two processed fluids are mixed (reacted) between the processing surfaces 1 and 2, at least one processed fluid pressurized with the fluid pressure imparting mechanism is passed through the space between the first processing surface 1 and the second processing surface 2 rotating to each other and supplied with surface-approaching pressure, and another processed fluid is passed, so that the processed fluid pressurized with the fluid pressure imparting mechanism, while being passed between the processing surfaces and forming a fluid film of predetermined thickness, is mixed with another processed fluid, whereby a desired mixing (reaction) is caused between the processed fluids.

The surface-approaching pressure imparting mechanism can constitute a buffer mechanism of regulating micro-vibration and alignment and a displacement regulation mechanism in the apparatus described above.

The fluid processing apparatus for carrying out the present invention comprises a first introduction part that introduces, into the apparatus, at least one of two processed fluids to be mixed (reacted), a fluid pressure imparting mechanism p that is connected to the first introduction part and imparts pressure to the processed fluid, a second introduction part that introduces at least the other fluid of the two processed fluids to be mixed (reacted), at least two processing members, that is, a first processing member 10 arranged in a sealed fluid flow path through which the other processed fluid is passed and a second processing member 20 capable of relatively approaching to and separating from the first processing member 10, at least two processing surfaces, that is, a first processing surface 1 and a second processing surface 2 arranged so as to be opposite to each other in the processing members 10 and 20, a holder 21 that accepts the second processing member 20 so as to expose the second processing surface 2, a rotation drive mechanism that relatively rotates the first processing member 10 and the second processing member 20, and a surface-approaching pressure imparting mechanism 4 that presses the second processing member 20 against the first processing surface 1 such that the second processing surface 2 is contacted against or made close to the first processing surface 1, wherein the processed fluids are mixed (reacted) between the processing surfaces 1 and 2, the holder 21 is provided with an opening of the first introduction part and is not movable so as to influence the space between the processing surfaces 1 and 2, at least one of the first processing member 10 and the second introduction part 20 is provided with an opening of the second introduction part, the second processing member 20 is circular, the second processing surface 2 slides along the holder 21 and approaches to and separates from the first processing surface 1, the second processing member 20 includes a pressure-receiving surface, the pressure-receiving surface receives pressure applied from the fluid pressure imparting mechanism p to the processed fluid to generate a force to move in the direction of separating the second processing surface 2 from the first processing surface 1, at least a part of the pressure-receiving surface is comprised of the second processing surface 2, one of the processed fluids to which pressure was applied is passed through the space between the first processing surface 1 and the second processing surface 2 rotating to each other and capable of approaching to and separating from each other, and the other processed fluid is supplied to the space between the processing surfaces 1 and 2, whereby both the processed fluids form a fluid film of predetermined thickness and pass through the space between both the processing surfaces 1 and 2, the passing processed fluid are mixed thereby promoting a desired mixing (reaction) between the processed fluids, and the minimum distance for generating the fluid film of predetermined thickness is kept between the processing surfaces 1 and 2 by the balance between the surface-approaching pressure by the surface-approaching pressure imparting mechanism 4 and the force of separating the processing surfaces 1 and 2 from each other by the fluid pressure imparted by the fluid pressure imparting mechanism p.

In this processing apparatus, the second introduction part can be, similarly being connected to the first processing member 1, arranged to be connected to a separate fluid pressure imparting mechanism and to be pressurized. The processed fluid introduced from the second introduction part is not pressurized by the separate fluid pressure imparting mechanism, but is sucked and supplied into the space between the processing surfaces 1 and 2 by negative pressure generated in the second introduction part by the fluid pressure of the processed fluid introduced into the first introduction part. Alternatively, the other processed fluid flows downward by its weight in the second introduction part and can be supplied into the space between the processing surfaces 1 and 2.

As described above, the apparatus is not limited to the one wherein the opening of the first introduction part as an inlet for feeding the other processed fluid into the apparatus is arranged in the second holder, and the opening of the first introduction part may be arranged in the first holder. The opening of the first introduction part may be formed with at least one of the processing surfaces. However, when the processed fluid to be previously introduced into the space between the processing surfaces 1 and 2 should, depending on the reaction, be supplied from the first introduction part, the opening of the second introduction part as an inlet for feeding the other processed fluid into the apparatus should be arranged downstream from the opening of the first introduction part in any of the processing surfaces.

As the fluid processing apparatus for carrying out the present invention, the following apparatus can be used.

This processing apparatus comprises a plurality of introduction parts that separately introduce two or more processed fluids to be mixed (reacted), a fluid pressure imparting mechanism p that imparts pressure to at least one of the two or more processed fluids, at least two processing members, that is, a first processing member 10 arranged in a sealed fluid flow path through which the processed fluid is passed and a second processing member 20 capable of approaching to and separating from the first processing member 10, at least two processing surfaces 1 and 2, that is, a first processing surface 1 and a second processing surface 2 arranged in a position in which they are faced with each other in the processing members 10 and 20, and a rotation drive mechanism that relatively rotates the first processing member 10 and the second processing member 20, wherein the processed fluids are mixed (reacted) between the processing surfaces 1 and 2, at least the second processing member 20 of the first processing member 10 and the second processing member 20 includes a pressure-receiving surface, at least a part of the pressure-receiving surface is comprised of the second processing surface 2, the pressure-receiving surface receives pressure applied by the fluid pressure imparting mechanism to the processed fluid to generate a force to move in the direction of separating the second processing surface 2 from the first processing surface 1, the second processing member 20 includes an approach regulating surface 24 that is directed to the opposite side of the second processing surface 2, the approach regulating surface 24 receives predetermined pressure applied to the processed fluid to generate a force to move in the direction of approaching the second processing surface 2 to the first processing surface 1, a force to move in the direction of separating the second processing surface 2 from the first processing surface 1 as a resultant force of total pressure received from the processed fluid is determined by the area ratio of the projected area of the approach regulating surface 24 in the approaching and separating direction to the projected area of the pressure-receiving surface in the approaching and separating direction, the processed fluid to which pressure was applied is passed through the space between the first processing surface 1 and the second processing surface 2 that rotate relative to each other and capable of approaching to and separating from each other, the other processed fluid to be mixed (reacted) with the processed fluid is mixed in the space between the processing surfaces, and the mixed processed fluid forms a fluid film of predetermined thickness and simultaneously passes through the space between the processing surfaces 1 and 2, thereby giving a desired product while passing through the space between the processing surfaces.

The fluid processing method according to the present invention is summarized as follows. The fluid processing method comprises applying predetermined pressure to a first fluid, connecting at least two processing surfaces, that is, a first processing surface 1 and a second processing surface 2, which are capable of approaching to and separating from each other, to a sealed fluid flow path through which the processed fluid that has received the predetermined pressure is passed, applying a surface-approaching pressure of approaching the first processing surface 1 and the second processing surface 2 each other, rotating the first processing surface 1 and the second processing surface 2 relative to each other, and introducing the processed fluid into the space between the processing surfaces 1 and 2, wherein the second processed fluid to be mixed (reacted) with the processed fluid is introduced through a separate flow path into the space between the processing surfaces 1 and 2 thereby mixing (reacting) both the processed fluids, the predetermined pressure applied to at least the first processed fluid functions as a separating force for separating the processing surfaces 1 and 2 from each other, and the separating force and the surface-approaching pressure are balanced via the processed fluid between the processing surfaces 1 and 2, whereby the distance between the processing surfaces 1 and 2 is kept in a predetermined minute space, the processed fluid is passed as a fluid film of predetermined thickness through the space between the processing surfaces 1 and 2, and when both the processed fluids are uniformly mixed (reacted) with each other while passing and accompanied by separation, a desired reaction product is crystallized or separated.

Figure 25:
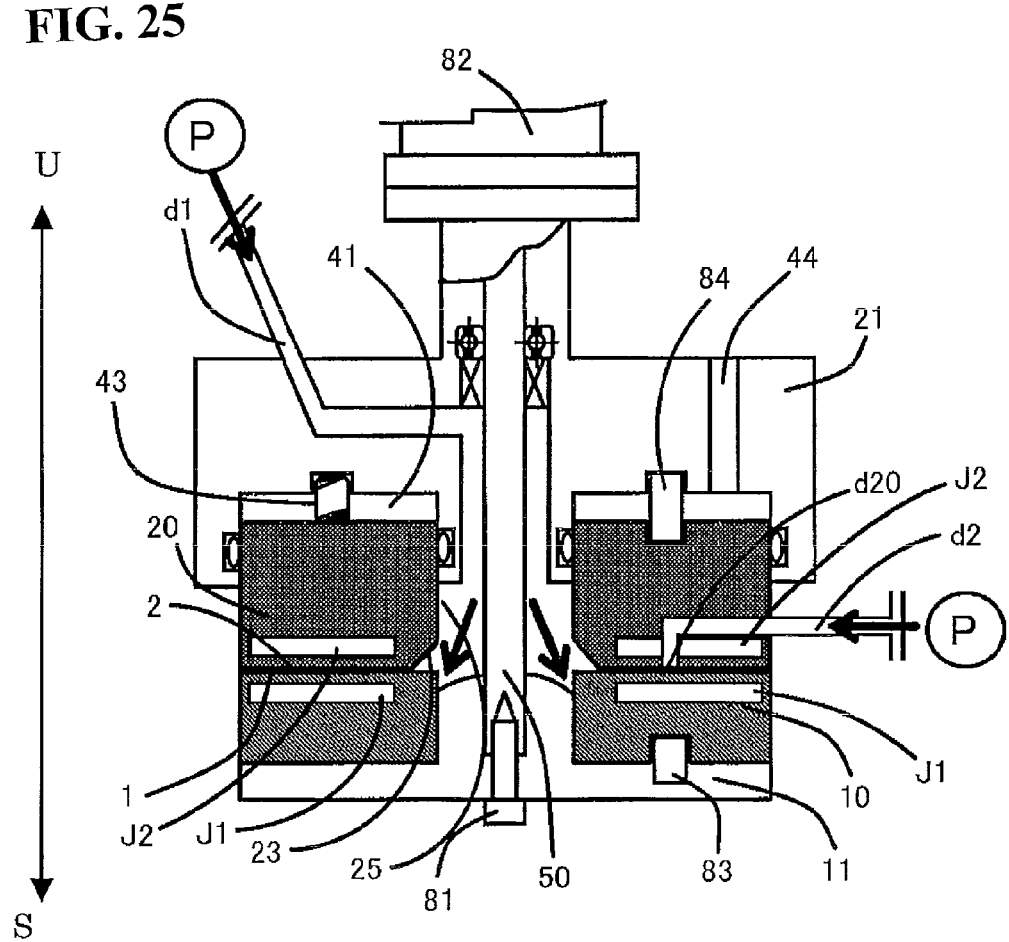
FIG. 25 is a schematic vertical sectional view showing outline of the apparatus of the present invention.
Figure 26A:
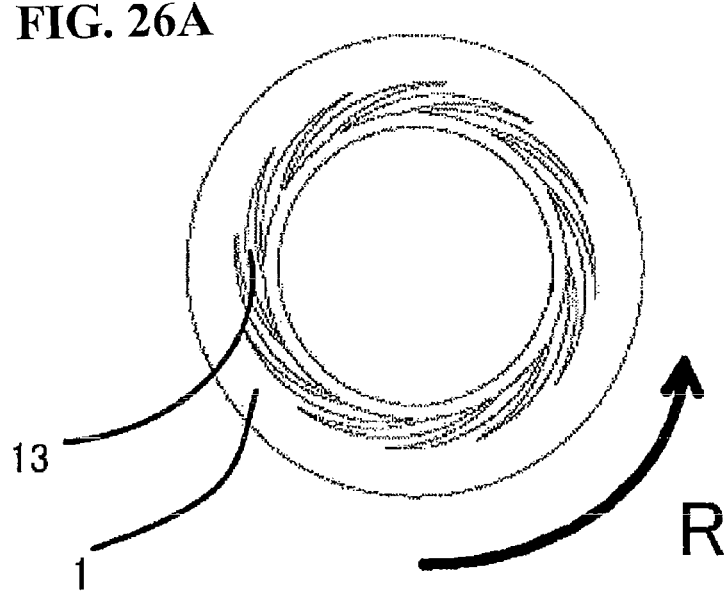
FIG. 26(A) is a schematic plane view of the first processing surface in the apparatus shown in FIG. 25.
Figure 26B:
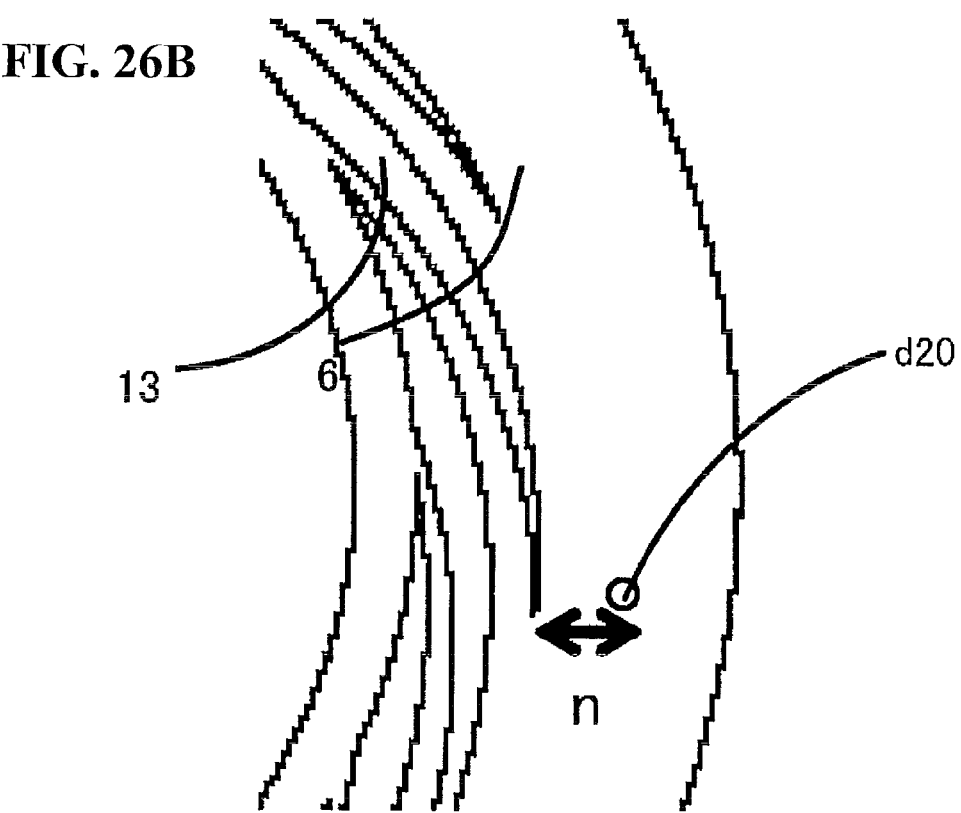
FIG. 26(B) is an enlarged view showing an important part of the first processing surface in the apparatus shown in FIG. 25.
Figure 27A:
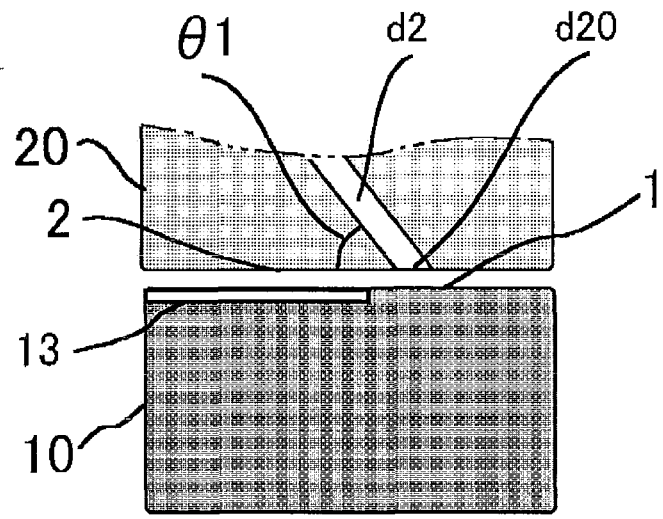
FIG. 27(A) is a sectional view of the second introduction path.
Figure 27B:
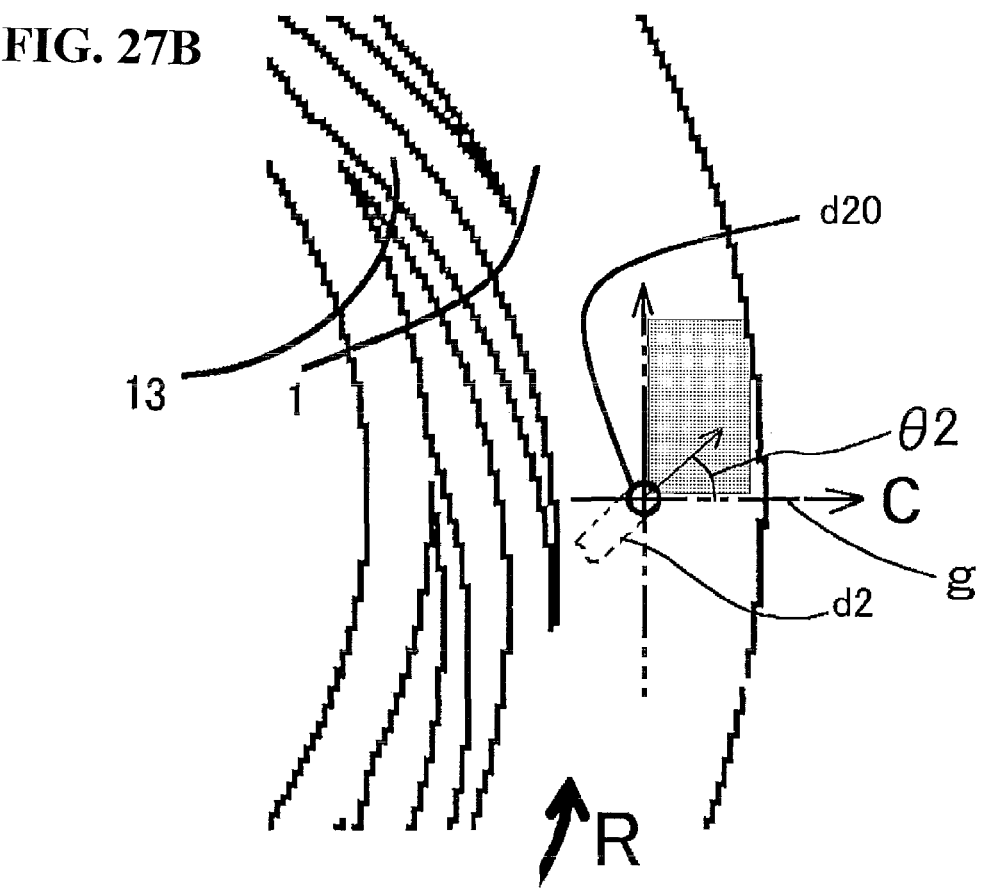
FIG. 27(B) is an enlarged view showing an important part of the processing surface for explaining the second introduction path.

Hereinafter, other embodiments of the present invention are described in detail. FIG. 25 is a schematic sectional view of a fluid processing apparatus wherein materials to be processed are processed between processing surfaces, at least one of which rotates to the other, and which are capable of approaching to and separating from each other. FIG. 26(A) is a schematic plane view of the first processing surface in the apparatus shown in FIG. 25, and FIG. 26(B) is an enlarged view of an important part of the processing surface in the apparatus shown in FIG. 25. In FIG. 27(A) is a sectional view of the second introduction path, and FIG. 27(B) is an enlarged view of an important part for explaining the second introduction path.

In FIG. 25, arrows U and S show upward and downward directions respectively. In FIG. 26(A) and FIG. 27(B), arrow R shows the direction of rotation. In FIG. 27(B), arrow C shows the direction of centrifugal force (radial direction).

This apparatus uses at least two fluids, at least one of which contains at least one kind of material to be processed, and the fluids join together in the space between the processing surfaces arranged to be opposite so as to be able to approach to and separate from each other, at least one of which rotates relative to the other, thereby forming a thin film fluid, and the materials to be processed are processed in the thin film fluid. The "process" includes not only a form in which the processed material is reacted, but also a form in which only mixing or dispersion is conducted without accompanying reaction.

As shown in FIG. 25, this apparatus includes a first holder 11, a second holder 21 arranged over the first holder 11, a fluid pressure imparting mechanism P and a surface-approaching pressure imparting mechanism. The surface-approaching pressure imparting mechanism is comprised of a spring 43 and an air introduction part 44.

The first holder 11 is provided with a first processing member 10 and a rotary shaft 50. The first processing member 10 is a circular body called a maintaining ring and provided with a mirror-polished first processing surface 1. The rotary shaft 50 is fixed to the center of the first holder 11 with a fixing device 81 such as a bolt and is connected at its rear end to a rotation drive device 82 (rotation drive mechanism) such as a motor, and the drive power of the rotation drive device 82 is transmitted to the first holder 1 thereby rotating the first holder 11. The first processing member 10 is integrated with the first holder 11 and rotated.

A receiving part capable of receiving the first processing member 10 is arranged on the upper part of the first holder 11, wherein the first processing member 10 has been fixed to the first holder 11 by insertion to the receiving part. The first processing member 10 has been fixed with a rotation preventing pin 83 so as not to be rotated relative to the first holder 11. However, a method such as fitting by burning may be used for fixing in place of the rotation-preventing pin 83 in order to prevent rotation.

The first processing surface 1 is exposed from the first holder 11 and faced with the second holder 21. The material for the first processing surface includes ceramics, sintered metal, abrasion-resistant steel, other hardened metals, and rigid materials subjected to lining, coating or plating.

The second holder 21 is provided with a second processing member 20, a first introduction part d1 for introducing a fluid from the inside of the processing member, a spring 43 as a surface-approaching pressure imparting mechanism, and an air introduction part 44.

The second processing member 20 is a circular member called a compression ring and includes a second processing surface 2 subjected to mirror polishing and a pressure-receiving surface 23 (referred to hereinafter as a separation regulating surface 23) which is located inside the second processing surface 2 and adjacent to the second processing surface 2. As shown in the figure, the separation regulating surface 23 is an inclined surface. The method of the mirror polishing to which the second processing surface 2 was subjected is the same as that to the first processing surface 1. The material for the second processing member 20 may be the same as one for the first processing member 10. The separation regulating surface 23 is adjacent to the inner periphery 25 of the circular second processing member 20.

A ring-accepting part 41 is formed in the bottom (lower part) of the second holder 21, and the second processing member 20 together with an O-ring is accepted in the ring-accepting part 41. The second processing member 20 is accepted with a rotation preventive 84 so as not to be rotated relative to the second holder 21. The second processing surface 2 is exposed from the second holder 21. In this state, the second processing surface 2 is faced with the first processing surface 1 of the first processing member 10.

The ring-accepting part 41 arranged in the second holder 21 is a depression for mainly accepting that side of the second ring 20 which is opposite to the processing surface 2 and is a groove formed in a circular form when viewed in a plane.

The ring-accepting part 41 is formed in a larger size than the second ring 20 and accepts the second ring 20 with sufficient clearance between itself and the second ring 20.

By this clearance, the second processing member 20 is accepted in the ring-accepting part 41 such that it can be displaced not only in the axial direction of the accepting part 41 but also in a direction perpendicular to the axial direction. The second processing member 20 is accepted in the ring-accepting part 41 such that the central line (axial direction) of the second processing member 20 can be displaced so as not to be parallel to the axial direction of the ring-accepting part 41.

The spring 43 is arranged as a processing member-biasing part in at least the ring-accepting part 41 of the second holder 21. The spring 43 biases the second processing member 20 toward the first processing member 10. As another bias method, air pressure such as one in the air introduction part 44 or another pressurization means for applying fluid pressure may be used to bias the second processing member 20 held by the second holder 21 in the direction of approaching the second processing member 20 to the first processing member 10.

The surface-approaching pressure imparting mechanism such as the spring 43 or the air introduction part 44 biases each position (each position in the processing surface) in the circumferential direction of the second processing member 20 evenly toward the first processing member 10.

The first introduction part d1 is arranged on the center of the second holder 21, and the fluid which is pressure-fed from the first introduction part d1 to the outer periphery of the processing member is first introduced into the space surrounded with the second processing member 20 held by the second holder 21, the first processing member 10, and the first holder 11 that holds the first processing member 10. Then, the feeding pressure (supply pressure) of the fluid by the fluid pressure imparting mechanism P is applied to the pressure-receiving surface 23 arranged in the second processing member 20, in the direction of separating the second processing member 20 from the first processing member 10 against the bias of the biasing part.

Figure 29A:
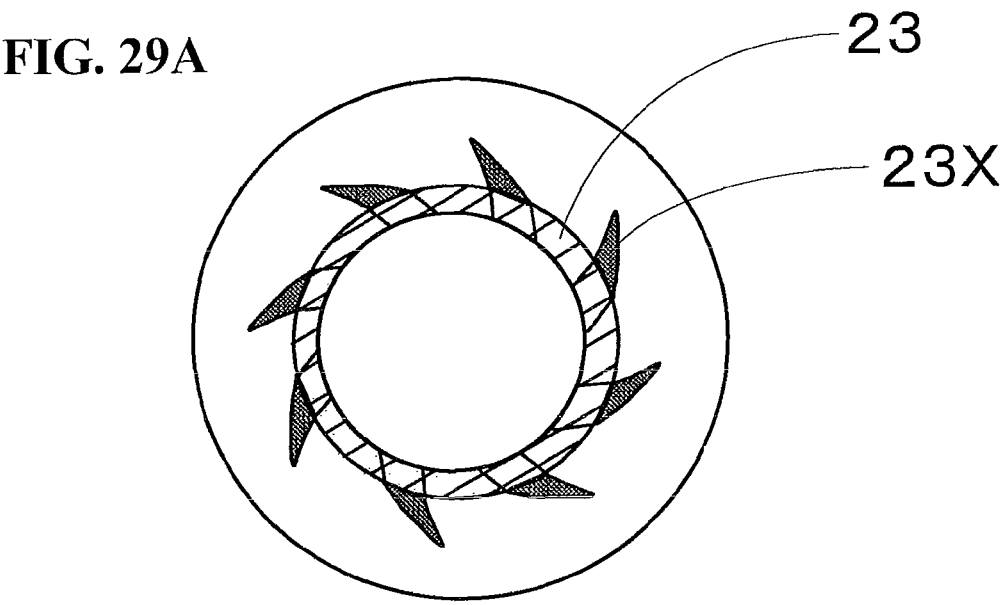
FIG. 29(A) is a bottom view of the second processing member.
Figure 29B:
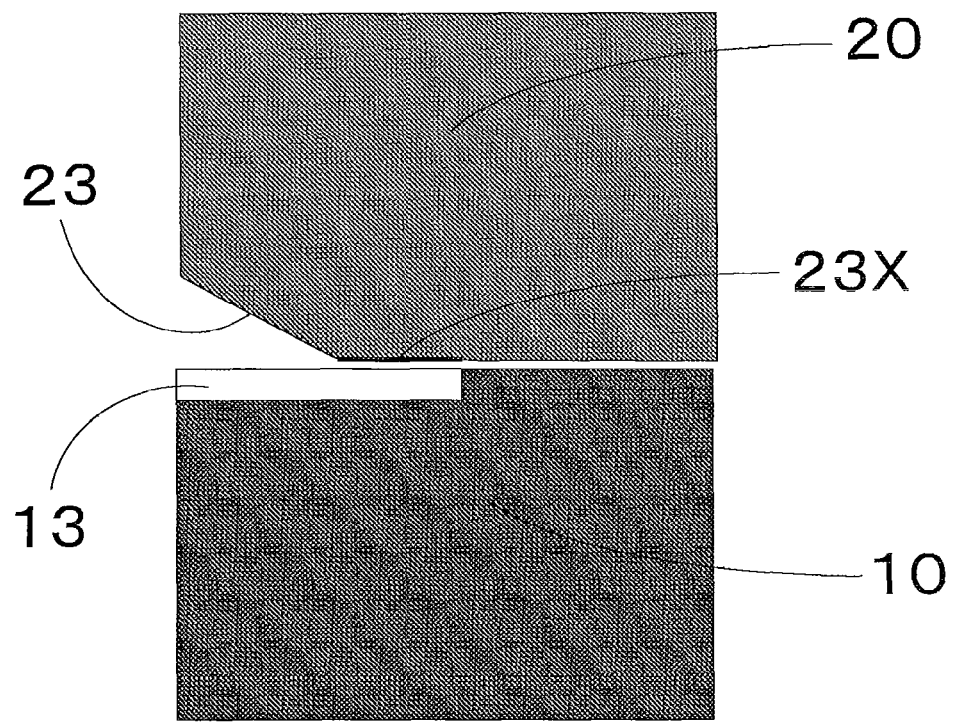
FIG. 29(B) is an enlarged sectional view showing an important part thereof.

For simplifying the description of other components, only the pressure-receiving surface 23 is described, as shown in FIG. 29(A) and FIG. 29(B), properly speaking, together with the pressure-receiving surface 23, a part 23X not provided with the pressure-receiving surface 23, out of the projected area in the axial direction relative to the second processing member 20 in a grooved depression 13 described later, serves as a pressure-receiving surface and receives the feeding pressure (supply pressure) of the fluid by the fluid pressure imparting mechanism P.

The apparatus may not be provided with the pressure-receiving surface 23. In this case, as shown in FIG. 26(A), the effect (micro-pump effect) of introduction of the processed fluid into the space between the processing surfaces formed by rotation of the first processing surface 1 provided with the grooved depression 13 formed to function the surface-approaching pressure imparting mechanism may be used. The micro-pump effect is an effect by which the fluid in the depression 13 advances with speed toward the end in the circumferential direction by rotation of the first processing surface 1 and then the fluid sent to the end of the depression 13 further receives pressure in the direction of the inner periphery of the depression 13 thereby finally receiving pressure in the direction of separating the processing surface and simultaneously introducing the fluid into the space between the processing surfaces. Even if the first processing surface 1 is not rotated, the pressure applied to the fluid in the depression 13 arranged in the first processing surface 1 finally acts on the second processing surface 2 to be separated as a pressure-receiving surface.

For the depression 13 arranged on the processing surface, its total area in the horizontal direction relative to the processing surface, and the depth, number, and shape of depressions, can be established depending on the physical properties of a fluid containing materials to be processed and reaction products.

The pressure-receiving surface 23 and the depression 13 may be arranged in the same apparatus.

The depression 13 is a depression having a depth of 1 μm to 50 μm, preferably 3 μm to 20 μm, which is arranged on the processing surface, the total area thereof in the horizontal direction is 5% to 50%, preferably 15% to 25%, based on the whole of the processing surface, the number of depressions is 3 to 50, preferably 8 to 24, and the depression extends in a curved or spiral form on the processing surface or bends at a right angle, having depth changing continuously, so that fluids with high to low viscosity, even containing solids, can be introduced into the space between the processing surfaces stably by the micro-pump effect. The depressions arranged on the processing surface may be connected to one another or separated from one another in the side of introduction, that is, inside the processing surface.

As described above, the pressure-receiving surface 23 is inclined. This inclined surface (pressure-receiving surface 23) is formed such that the distance in the axial direction between the upstream end in the direction of flow of the processed fluid and the processing surface of the processing member provided with the depression 13 is longer than the distance between the downstream end and the aforesaid processing surface. The downstream end of this inclined surface in the direction of flow of the processed fluid is arranged preferably on the projected area in the axial direction of the depression 13.

Figure 28A:
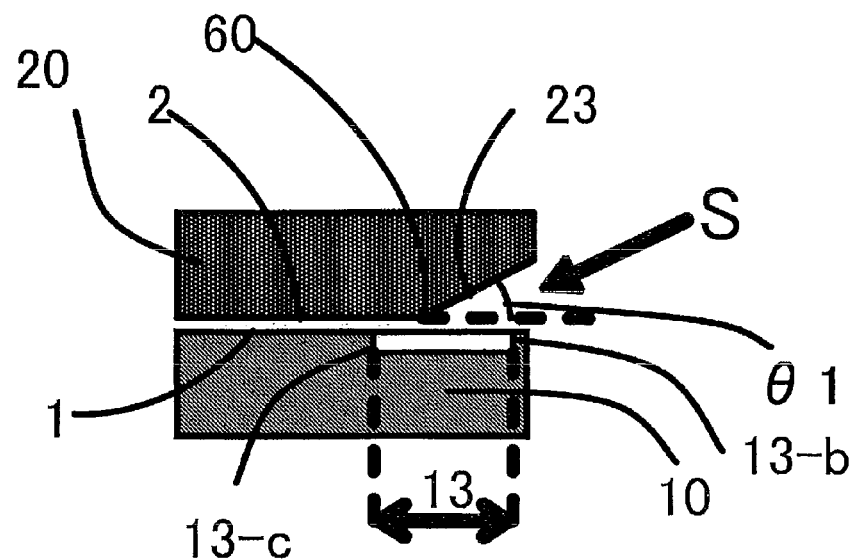
FIG. 28(A) and FIG. 28(B) are each an enlarged sectional view of an important part for explaining an inclined surface arranged in the processing member.
Figure 28B:
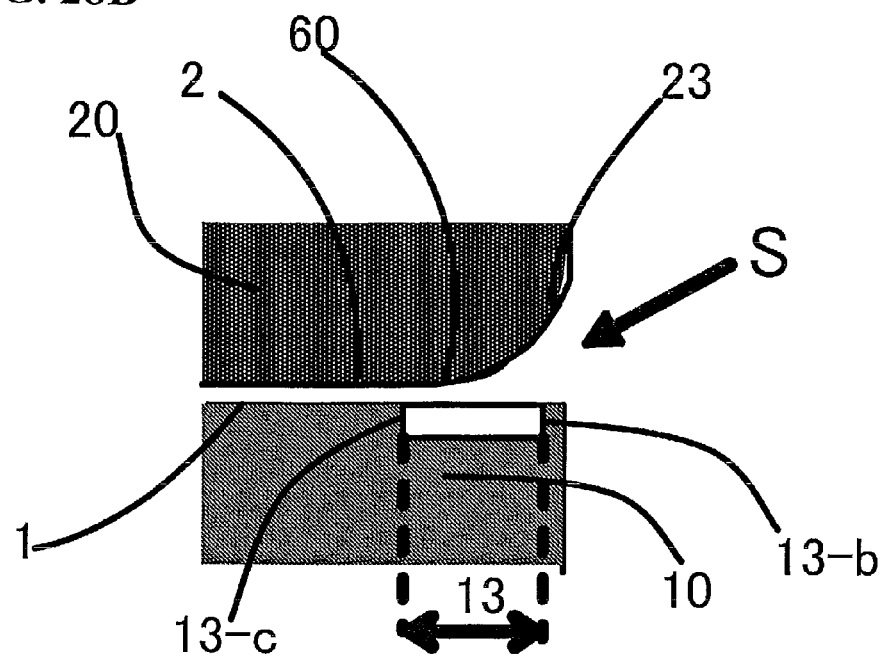

Specifically, as shown in FIG. 28(A), a downstream end 60 of the inclined surface (pressure-receiving surface 23) is arranged on the projected area in the axial direction of the depression 13. The angle θ1 of the inclined surface to the second processing surface 2 is preferably in the range of 0.1° to 85°, more preferably in the range of 10° to 55°, still more preferably in the range of 15° to 45°. The angle θ1 can vary depending on properties of the processed product before processing. The downstream end 60 of the inclined surface is arranged in the region extending from the position apart downstream by 0.01 mm from an upstream end 13-b to the position apart upstream by 0.5 mm from a downstream end 13-c in the depression 13 arranged in the first processing surface 1. The downstream end 60 of the inclined surface is arranged more preferably in the region extending from the position apart downstream by 0.05 mm from the upstream end 13-b to the position apart upstream by 1.0 mm from the downstream end 13-c. Like the angle of the inclined surface, the position of the downstream end 60 can vary depending on properties of a material to be processed. As shown in FIG. 28(B), the inclined surface (pressure-receiving surface 23) can be a curved surface. The material to be processed can thereby be introduced more uniformly.

The depressions 13 may be connected to one another or separated from one another as described above. When the depressions 13 are separated, the upstream end at the innermost peripheral side of the first processing surface 1 is 13-b, and the upstream end at the outermost peripheral side of the first processing surface 1 is 13-c.

In the foregoing description, the depression 13 was formed on the first processing surface 1 and the pressure-receiving surface 23 was formed on the second processing surface 2. On the contrary, the depression 13 may be formed on the second processing surface 2, and the pressure-receiving surface 23 may be formed on the first processing surface 1.

Alternatively, the depression 13 is formed both on the first processing surface 1 and the second processing surface 2, and the depression 13 and the pressure-receiving surface 23 are alternately arranged in the circumferential direction of each of the respective processing surfaces 1 and 2, whereby the depression 13 formed on the first processing surface 1 and the pressure-receiving surface 23 formed on the second processing surface 2 are faced with each other and simultaneously the pressure-receiving surface 23 formed on the first processing surface 1 and the depression 13 formed on the second processing surface 2 are faced with each other.

A groove different from the depression 13 can be formed on the processing surface. Specifically, as shown in FIG. 16(F) and FIG. 16(G), a radially extending novel depression 14 instead of the depression 13 can be formed outward in the radial direction (FIG. 16(F)) or inward in the radial direction (FIG. 16(G)). This is advantageous for prolongation of retention time between the processing surfaces or for processing a highly viscous fluid.

The groove different from the depression 13 is not particularly limited with respect to the shape, area, number of depressions, and depth. The groove can be formed depending on the object.

The second introduction part d2 independent of the fluid flow path introduced into the processing surface and provided with the opening d20 leading to the space between the processing surfaces is formed on the second processing member 20.

Specifically, as shown in FIG. 27(A), the direction of introduction of the second introduction part d2 from the opening d20 of the second processing surface 2 is inclined at a predetermined elevation angle (θ1) relative to the second processing surface 2. The elevation angle (θ1) is arranged at more than 0° and less than 90°, and when the reaction speed is high, the angle (θ1) is preferably arranged at 1° to 45°.

As shown in FIG. 27(B), the direction of introduction of the second processing surface 2 from the opening d20 has directionality in a plane along the second processing surface 2. The direction of introduction of the second fluid is in the direction in which a component on the processing surface is made apart in the radial direction and in the direction in which the component is forwarded in the rotation direction of the fluid between the rotating processing surfaces. In other words, a predetermined angle (θ2) exists facing the rotation direction R from a reference line g in the outward direction and in the radial direction passing through the opening d20.

The angle (θ2) is also arranged at more than 0° and less than 90° at which the fluid is discharged from the opening d20 in the shaded region in FIG. 27(B). When the reaction speed is high, the angle (θ2) may be small, and when the reaction speed is low, the angle (θ2) is preferably arranged larger. This angle can vary depending on various conditions such as the type of fluid, the reaction speed, viscosity, and the rotation speed of the processing surface.

The bore diameter of the opening d20 is preferably 0.2 μm to 3000 μm, more preferably 10 μm to 1000 μm. When the diameter of the opening d20 does not substantially influence the flow of a fluid, the diameter of the second introduction part d2 may be established in this range. Depending on whether the fluid is intended to be transferred straight or dispersed, the shape of the opening d20 is preferably changed and can be changed depending on various conditions such as the type of fluid, reaction speed, viscosity, and rotation speed of the processing surface.

The opening d20 in the separate flow path may be arranged at a position nearer to the outer diameter than a position where the direction of flow upon introduction by the micro-pump effect from the depression arranged in the first processing surface 1 is converted into the direction of flow of a spiral laminar flow formed between the processing surfaces. That is, in FIG. 26(B), the distance n from the outermost side in the radial direction of the processing surface of the depression 13 arranged in the first processing surface 1 to the outside in the radial direction is preferably 0.5 mm or more. When a plurality of openings are arranged for the same fluid, the openings are arranged preferably concentrically. When a plurality of openings are arranged for different fluids, the openings are arranged preferably concentrically in positions different in radius. This is effective for the reactions such as cases (1) A+B→C and (2) C+D→E should occur in due order, but other case, i.e., A+B+C→F should not occur, or for circumventing a problem that an intended reaction does not occur due to insufficient contact among the processed materials.

The processing members are dipped in a fluid, and a fluid obtained by mixing (reaction) between the processing surfaces can be directly introduced into a liquid outside the processing members or into a gas other than air.

Further, ultrasonic energy can be applied to the processed material just after being discharged from the space between the processing surfaces or from the processing surface.

Then, the case where temperature regulating mechanisms J1 and J2 are arranged in at least one of the first processing member 10 and the second processing member 20 for generating a temperature difference between the first processing surface 1 and the second processing surface 2 is described.

The temperature regulating mechanism is not particularly limited. A cooling part is arranged in the processing members 10 and 20 when cooling is intended. Specifically, a piping for passing ice water and various cooling media or a cooling element such as a Peltier device capable of electric or chemical cooling is attached to the processing members 10 and 20.

When heating is intended, a heating part is arranged in the processing members 10 and 20. Specifically, steam as a temperature regulating medium, a piping for passing various hot media, and a heating element such as an electric heater capable of electric or chemical heating is attached to the processing members 10 and 20.

An accepting part for a new temperature regulating medium capable of directly contacting with the processing members may be arranged in the ring-accepting part. The temperature of the processing surfaces can be regulated by heat conduction of the processing members. Alternatively, a cooling or heating element may be embedded in the processing members 10 and 20 and electrified, or a path for passing a cooling medium may be embedded, and a temperature regulating medium (cooling medium) is passed through the path, whereby the temperature of the processing surfaces can be regulated from the inside. By way of example, the temperature regulating mechanisms J1 and J2 which are pipes (jackets) arranged inside the processing members 10 and 20 are shown in FIG. 25.

By utilizing the temperature regulating mechanisms J1 and J2, the temperature of one of the processing surfaces is made higher than that of the other, to generate a temperature difference between the processing surfaces. For example, the first processing member 10 is heated to 60° C. by any of the methods, and the second processing member 20 is set at 15° C. by any of the methods. In this case, the temperature of the fluid introduced between the processing surfaces is changed from 60° C. to 15° C. in the direction from the first processing surface 1 to the second processing surface 2. That is, the fluid between the processing surfaces has a temperature gradient. The fluid between the processing surfaces initiates convection due to the temperature gradient, and a flow in a direction perpendicular to the processing surface is generated. The "flow in a direction perpendicular to the processing surface" refers to a flow in which components flowing in a direction perpendicular to at least the processing surface are contained in flowing components.

Even when the first processing surface 1 or the second processing surface 2 rotates, the flow in a direction perpendicular to the processing surface is continued, and thus the flow in a direction perpendicular to the processing surface can be added to a spiral laminar flow between the processing surfaces caused by rotation of the processing surfaces. The temperature difference between the processing surfaces is 1° C. to 400° C., preferably 5° C. to 100° C.

The rotary shaft 50 in this apparatus is not limited to a vertically arranged shaft. For example, the rotation axis may be arranged at a slant. This is because the influence of gravity can be substantially eliminated by a thin fluid film formed between the processing surfaces 1 and 2 during processing. As shown in FIG. 25, the first introduction part d1 coincides with the shaft center of the second ring 20 in the second holder 21 and extends vertically. However, the first introduction part d1 is not limited to the one coinciding with the shaft center of the second ring 20, and as far as it can supply the first processing fluid to the space surrounded with the rings 10 and 20, the part d1 may be arranged at a position outside the shaft center in the central part 22 of the second holder 21 and may extend obliquely as well as vertically. Regardless of the angle at which the part d1 is arranged, a flow perpendicular to the processing surface can be generated by the temperature gradient between the processing surfaces.

When the temperature gradient of the fluid between the processing surfaces is low, heat conduction merely occurs in the fluid, but when the temperature gradient exceeds a certain border value, a phenomenon called Benard convection is generated in the fluid. This phenomenon is governed by Rayleigh number Ra, a dimensionless number, defined by the following equation:

$$Ra = L^3 \cdot g \cdot \beta \cdot \Delta T / (\alpha \cdot v)$$

wherein L is the distance between processing surfaces; g is gravitational acceleration; $\beta$ is coefficient of volumetric thermal expansion of fluid; $v$ is dynamic viscosity of fluid; $\alpha$ is heat diffusivity of fluid; and $\Delta T$ is temperature difference between processing surfaces. The critical Rayleigh number at which Benard convection is initiated to occur, although varying depending on the properties of a boundary phase between the processing surface and the processed fluid, is regarded as about 1700. At a value higher than this value, Benard convection occurs. Under the condition where the Rayleigh number Ra is a large value of about $10^{10}$ or more, the fluid becomes a turbulent flow. That is, the temperature difference $\Delta T$ between the processing surfaces or the distance L between the processing surfaces in this apparatus are regulated such that the Rayleigh number Ra becomes 1700 or more, whereby a flow perpendicular to the processing surface can be generated between the processing surfaces, and the mixing (reaction) procedures described above can be carried out.

However, the Benard convection hardly occurs when the distance between the processing surfaces is about 1 µm to 10 µm. Strictly, when the Rayleigh number is applied to a fluid between the processing surfaces having a distance of 10 µm or less therebetween to examine the conditions under which Benard convection is generated, the temperature difference should be several thousands of degrees or more in the case of water, which is practically difficult. Benard convection is one related to density difference in temperature gradient of a fluid, that is, to gravity. When the distance between the processing surfaces is 10 µm or less, there is high possibility of minute gravity field, and in such a place, buoyancy convection is suppressed. That is, it is the case where the distance between the processing surfaces is 10 µm or more that Benard convection actually occurs.

When the distance between the processing surfaces is about 1 µm to 10 µm, convection is generated not due to density difference but due to surface tension difference of a fluid resulting from temperature gradient. Such convection is Marangoni convection. This phenomenon is governed by Marangoni number, a dimensionless number, defined by the following equation:

$$Ma = \sigma \cdot \Delta T \cdot L / (\rho \cdot v \cdot \alpha)$$

wherein L is the distance between processing surfaces; ν is dynamic viscosity of fluid; α is heat diffusivity of fluid; ΔT is temperature difference between processing surfaces; ρ is density of fluid; and σ is temperature coefficient of surface tension (temperature gradient of surface tension). The critical Marangoni number at which Marangoni convection is initiated to occur is about 80, and under the conditions where the Marangoni number is higher than this value, Marangoni convection occurs. That is, the temperature difference ΔT between the processing surfaces or the distance L between the processing surfaces in this apparatus is regulated such that the Marangoni number Ma becomes 80 or more, whereby a flow perpendicular to the processing surface can be generated between the processing surfaces even if the distance therebetween is as small as 10 μm or less, and the mixing (reaction) procedures described above can be carried out.

For calculation of Rayleigh number, the following equations were used.

$$Ra = \frac{L^3 \cdot \beta \cdot g}{\nu \cdot \alpha} \Delta T \qquad \text{[Equation 1]}$$

$$\Delta T = (T_1 - T_0)$$

$$\alpha = \frac{k}{\rho \cdot C_p}$$

L is the distance (m) between processing surfaces; β is coefficient of volumetric thermal expansion (1/K); g is gravitational acceleration (m/s$^2$); ν is dynamic viscosity (m$^2$/s); α is heat diffusivity (m$^2$/s); ΔT is temperature difference (K) between processing surfaces;
ρ is density (kg/m$^3$); Cp is isobaric specific heat (J/kg·K);
k is heat conductivity (W/m·K);
$T_1$ is temperature (K) at high temperature side in processing surface; and $T_0$ is temperature (K) at low temperature side in processing surface.

When the Rayleigh number at which Benard convection is initiated to occur is the critical Rayleigh number $Ra_C$, the temperature difference $\Delta T_{C1}$ is determined as follows:

$$\Delta T_{C1} = \frac{Ra_C \cdot \nu \cdot \alpha}{L^3 \cdot \beta \cdot g} \qquad \text{[Equation 2]}$$

For calculation of Marangoni number, the following equations were used.

$$Ma = \frac{\sigma_t \cdot L}{\rho \cdot \nu \cdot \alpha} \Delta T \qquad \text{[Equation 3]}$$

$$\Delta T = (T_1 - T_0)$$

$$\alpha = \frac{k}{\rho \cdot C_p}$$

L is the distance (m) between processing surfaces; ν is dynamic viscosity (m$^2$/s); α is heat diffusivity (m$^2$/s);
ΔT is temperature difference (K) between processing surfaces;
ρ is density (kg/m$^3$); Cp is isobaric specific heat (J/kg·K);
k is heat conductivity (W/m·K); $\sigma_t$ is surface tension temperature coefficient (N/m·k);
$T_1$ is temperature (K) at high temperature side in processing surface; and $T_0$ is temperature (K) at low temperature side in processing surface.

When the Marangoni number at which Marangoni convection is initiated to occur is the critical Marangoni number $Ma_C$, the temperature difference $\Delta T_{C2}$ is determined as follows:

$$\Delta T_{C2} = \frac{Ma_C \cdot \rho \cdot \nu \cdot \alpha}{\sigma_t \cdot L} \qquad \text{[Equation 4]}$$

The materials for the processing surface arranged to be opposite to each other so as to be able to approach to and separate from each other, at least one of which rotates relative to the other, are not particularly limited, and the processing surfaces 1 and 2 can be prepared from ceramics, sintered metals, abrasion-resistant steels, other metals subjected to hardening treatment, or rigid materials subjected to lining, coating or plating. In the present invention, the distance between the processing surfaces 1 and 2 arranged to be opposite to each other so as to be able to approach to and separate from each other, at least one of which rotates relative to the other, is 0.1 μm to 100 μm, particularly preferably 1 μm to 10 μm.

Hereinafter, the reaction of formation of microparticles in the present invention is described in more detail with reference to aciclovir as an example. However, the present invention is not limited to these embodiments.

Aciclovir (general name: JAN, INN) (chemical name: 9-[(2-hydroxyethoxy)methyl]guanine) is an antiviral agent having a purine skeleton and is a compound used widely clinically as a therapeutic agent for infections caused by herpes simplex virus, chickenpox virus and herpes zoster virus, that is, herpes simplex, chickenpox, herpes zoster, encephalitis, meningitis, and the like, which have been developed in immune-compromised patients (malignant tumor, autoimmune disease, and the like). The solubility of aciclovir in water at ordinary temperatures is low (about 0.001 w/v % to 0.01 w/v %), but can be dissolved to about 8 w/v % by heating to a temperature of 70° C. or more.

This reaction occurs by forced uniform mixing between the processing surfaces 1 and 2 arranged to be opposite to each other so as to be able to approach to and separate from each other, at least one of which rotates relative to the other, in the apparatus shown in FIG. 1(A).

First, a cooling fluid containing an aqueous solvent at a lower temperature than a second fluid described later is introduced as a first fluid through one flow path, that is, the first introduction part d1 into the space between the processing surfaces 1 and 2 arranged to be opposite to each other so as to be able to approach to and separate from each other, at least one of which rotates relative to the other, thereby forming a first fluid film between the processing surfaces.

Then, a fluid wherein at least one kind of solution having aciclovir dissolved in water heated to 85° C. is introduced as a second fluid directly through another flow path, that is, the second introduction part d2 into the first fluid film produced between the processing surfaces 1 and 2.

As described above, the first and second fluids join together in a thin film fluid produced between the processing surfaces 1 and 2, the distance of which is regulated by the pressure balance between the supply pressure of the fluid and the pressure exerted between the rotating processing surfaces. The first and second fluids are mixed in the thin film fluid and when the temperature of the mixture of the first and second fluids becomes less than 70° C., aciclovir originally contained in the second fluid in the mixture is separated. Specifically, when the temperature of the aciclovir solution between the processing surfaces 1 and 2 is decreased, the solubility of aciclovir in water can be decreased to separate aciclovir microparticles. By the processing surfaces 1 and 2, at least one of which rotates relative to the other, the thin film fluid between the processing surfaces 1 and 2 is forcibly uniformly mixed, so that without forming an interface between the first and second fluids to cause insufficient mixing, the change in solubility by the temperature decrease is rapidly attained.

To effect the reaction (separation reaction) between the processing surfaces 1 and 2, the second fluid may be introduced through the first introduction part d1 and the first fluid through the second introduction part d2, as opposed to the above description. That is, the expression "first" or "second" for each fluid has a meaning for merely discriminating an $n^{th}$ fluid among a plurality of fluids present, and third or more fluids can also be present.

The same microparticle material may be contained in both the first and second fluids.

The particle size, monodispersity or crystal form of the obtained microparticles can be regulated by changing the number of revolutions of the processing surfaces 1 and 2, the distance between the processing surfaces 1 and 2 and the flow rate and temperature of the thin film fluid, and the concentration of materials.

The microparticle materials other than aciclovir are not particularly limited as long as their solubility in solution is changed by temperature. At this time, even if a curve of solubility (solubility curve) against temperature shows that the solubility is increased as the temperature increases, or that like calcium hydroxide or cesium sulfate, the solubility is decreased as the temperature increases, the method of the present invention can be applied. Even if the solubility such as that of sodium sulfate is maximized at a specific temperature (34.38° C. for sodium sulfate), the present method can be applied. In the case of aciclovir, a cooling fluid was introduced as the second fluid, and in the case of calcium hydroxide or cesium sulfate, a heating fluid may be introduced as the second fluid. In the case of sodium sulfate, a cooling fluid and a heating fluid may be appropriately selected depending on whether the temperature used is higher or lower the specific temperature.

As with the microparticle materials, the solvent used is not particularly limited either. Aqueous solvents such as water, ion-exchange water, ultrapure water, and aqueous acidic or alkaline solvents, or organic solvents such as methanol, ethanol and toluene can be used. Oils such as silicon oil, fats and oils containing unsaturated fats, sunflower oil or industrial gear oil may also be used.

The space between the processing surfaces 1 and 2 can be cooled or heated without using the cooling or heating fluid mentioned above. In this case, at least one of the first processing member 10 and the second processing 20 is provided with a temperature regulating mechanisms J1 and J2, and a microparticle material solution having solubility changing with temperature may be subjected to regulation of the temperature of the processing surfaces directly with the temperature regulating mechanisms, thereby separating microparticles between the processing surfaces 1 and 2.

The temperature regulating mechanism is not particularly limited. A cooling part is arranged in the processing members 10 and 20 when cooling is intended. Specifically, a piping for passing ice water and various cooling media or a cooling element such as a Peltier device capable of electric or chemical cooling is attached to the processing members 10 and 20.

When heating is intended, a heating part is arranged in the processing members 10 and 20. Specifically, steam as a temperature regulating medium, a piping for passing various hot media, and a heating element such as an electric heater capable of electric or chemical heating is attached to the processing members 10 and 20.

An accepting part for a new temperature regulating medium capable of directly contacting with the processing members may be arranged in the ring-accepting part. The temperature of the processing surfaces can be regulated by heat conduction of the processing members. Alternatively, a cooling or heating element may be embedded in the processing members 10 and 20 and electrified, or a path for passing a cooling medium may be embedded, and a temperature regulating medium (cooling medium) is passed through the path, whereby the temperature of the processing surfaces can be regulated from the inside. By way of example, the temperature regulating mechanisms J1 and J2 which are pipes (jackets) arranged inside the processing members 10 and 20 are shown in FIG. 25.

The whole of the processing members 10 and 20 may be dipped in a temperature regulating fluid. For example, the processing members 10 and 20 are accepted in a container, and a temperature regulating fluid is introduced into the container, thereby directly regulating the temperature of the processing members and the space between the processing surfaces.

Such mechanism can be used in combination with a temperature regulating fluid which is used for example as the second fluid.

At least one of solutions to be mixed such as the first and second fluids may contain a surfactant.

The surfactant that is used may be a known surfactant or a newly synthesized one and is not particularly limited. Various surfactants having excellent solubility in a solution and being capable of excellently dispersing separated microparticles in a solution can be used. The surfactants include various kinds of cationic surfactants, anionic surfactants and nonionic surfactants, sodium dodecylbenzene sulfonate, sodium dodecyl sulfate, sodium tetradecyl sulfate, sodium pentadecyl sulfate, sodium octyl sulfate, sodium oleate, sodium laurate, sodium stearate, calcium stearate, sucrose fatty acid esters, Tween 20 and Tween 80 (which are polyoxyethylene sorbitan fatty acid esters available from ICI Specialty Chemicals), polyvinyl pyrrolidone, tyloxapol, Pluronic F68 and F108 (which are ethylene oxide/propylene oxide block copolymers available from BASF), Tetronic 908 (T908) (which is a tetrafunctional block copolymer derived from an adduct of ethylene diamine to which ethylene oxide and propylene oxide are continuously added, available from BASF), dextran, lecithin, Aerosol OT (which is a dioctyl ester of sodium sulfosuccinate, available from American Cyanamid), Duponol P (which is sodium lauryl sulfate available from DuPont), Triton X-200 (which is an alkylaryl polyether sulfonate available from Rohm and Haas), Carbowax 3350 and 934 (which are polyethylene glycols available from Union Carbide), Crodesta F-110 (which is a mixture of sucrose stearate and sucrose distearate, available from Croda Inc.), Crodesta 5L-40 (which is available from Croda Inc.), and SA90HCO (which is $C_{18}H_{37}CH_2—(CON(CH_3)CH_2(CHOH)_4CH_2OH)_2$). These materials can be used depending on the objective microparticles.

In addition, the space between the processing surfaces may be heated (warmed), may be irradiated with ultraviolet ray (UV), or may be supplied with ultrasonic energy. Particularly, when a difference in temperature is set between the first processing surface 1 and the second processing surface 2, there is an advantage that since convection can be generated in a thin film fluid, the reaction can be promoted.

Specifically for heating (warming), at least one of the processing members 10 and 20 can be provided for example with a heater or a jacket for passing a heat medium, to heat (warm) the thin film fluid, as described above. For irradiation with ultraviolet ray (UV), at least one of the processing member 10 and the processing member 20 can be provided, for example, with an element such as UV lamp to irradiate the thin film fluid with ultraviolet ray (UV) from the corresponding processing surface. For supplying with ultrasonic energy, at least one of the processing member 10 and the processing member 20 can be provided, for example, with an ultrasonic wave oscillator.

The separation reaction is conducted in a container capable of securing a depressurized or vacuum state, and a secondary side at which the fluid after processing is discharged can be depressurized or made vacuous to remove a gas generated during the reaction, to remove a gas contained in the fluid, or to remove the solvent of the fluid. Even when the separation processing and the removal processing of the solvent are simultaneously conducted, a fluid containing microparticles separated between the processing surfaces is discharged in an atomized state from the processing surfaces, so the surface area of the fluid is increased, thus bringing about the advantage of very high efficiency of removal of the solvent. Accordingly, formation processing of microparticles and removal of the solvent can be effected in substantially one step more easily than before.

In this manner, a suspension wherein microparticles having an average primary particle size of 0.5 nm to 10000 nm, preferably 1 nm to 500 nm, more preferably 10 nm to 200 nm, are dispersed can be prepared. When the surfactant is added to a solution having microparticle materials dissolved therein, a suspension wherein microparticles having the dispersant coordinated thereon are dispersed can be prepared, and the resulting microparticles are very excellent in re-dispersibility. Contamination with foreign substances is low in the production process, and when crystals are separated, the degree of crystallization can be highly controlled.

As described above, the processing apparatus can be provided with a third introduction part d3 in addition to the first introduction part d1 and the second introduction part d2. In this case, a temperature regulating fluid, a solution containing microparticle materials, and a surfactant for example can be introduced separately through the respective introduction parts into the processing apparatus. By doing so, the concentration and pressure of each fluid can be separately controlled, and the reaction of forming microparticles can be regulated more accurately. When the processing apparatus is provided with four or more introduction parts, the foregoing applies and fluids to be introduced into the processing apparatus can be subdivided in this manner.

EXAMPLES

Hereinafter, the present invention is described in detail with reference to Examples, but the present invention is not limited to Examples.

In the following examples, the term "from the center" means "through the first introduction part d1" in the processing apparatus shown in FIG. 1(A), the first fluid refers to the first processed fluid, and the second fluid refers to the second processed fluid introduced "through the second introduction part d2" in the processing apparatus shown in FIG. 1(A).

An aqueous solution of aciclovir at 85° C. is cooled in a thin film between the processing surfaces 1 and 2 arranged to be opposite to each other so as to be able to approach to and separate from each other, at least one of which rotates relative to the other, in use of a uniformly stirring and mixing reaction apparatus shown in FIG. 1(A), thereby separating aciclovir.

Example 1

As a first fluid, 5% Tween 80 aqueous solution was sent from the center at a supply pressure/back pressure of 0.15 MPa/0.01 MPa, at a revolution number of 500 rpm and at a sending solution temperature of 15° C., and 3% aciclovir aqueous solution at 85° C. was introduced as a second fluid at a rate of 10 mL/min. into the space between the processing surfaces 1 and 2. The first and second fluids were mixed with each other in the thin film, and an aciclovir microparticle dispersion solution was discharged from the processing surfaces. The temperature of the discharged fluid was 48° C.

When the particle size distribution of the aciclovir microparticles solution was measured with a particle size distribution measuring instrument utilizing a laser Doppler method (trade name: Microtrac UPA150, manufactured by Nikkiso Co., Ltd.), the average particle size was 88.6 nm.

The aciclovir dispersion solution was vacuum freeze dried, and the resulting powdery aciclovir microparticles were introduced again into ion-exchange water and then stirred with a high-speed stirring dispersing machine (trade name: CLEARMIX manufactured by M Technique Co., Ltd.), whereby an aciclovir microparticle dispersion was obtained again, its average particle size was 88.1 nm, same as before vacuum free drying, and it was thus confirmed that the resulting aciclovir microparticles was excellent in re-dispersibility.

In Examples 2 to 4, aciclovir microparticle dispersions and aciclovir powders were obtained using the same Tween 80 aqueous solution and the same aciclovir aqueous solution as in Example 1, by changing the number of revolutions, supply pressure, and back pressure.

Comparative Example

First, 4% Tween 80/2% aciclovir aqueous solution was dissolved under stirring by heating to 85C, further aciclovir being dissolved. Then, the solution was stirred with CLEARMIX (manufactured by M Technique Co., Ltd.), during which the solution was cooled to 48C to form an aciclovir microparticle dispersion. At this time, the number of revolutions of CLEARMIX was 20000 rpm. An aciclovir microparticle dispersion having an average particle size of 1340 nm was obtained. When its re-dispersibility was confirmed in the same manner as in Examples, the particle size after re-dispersion was 3800 nm, and the particles were aggregated stronger than before vacuum freeze drying.

The results are shown in Table 1.

TABLE 1

| Example | First Fluid | Second Fluid | Number of Revolutions [rpm] | Supply Pressure [MPaG] | Back Pressure [MPaG] | Average Particle Size [nm] | Redispersibility |
|---|---|---|---|---|---|---|---|
| Example 1 | 5% Tween 80 aqueous solution | 3% aciclovir aqueous solution | 500 | 0.15 | 0.01 | 88.6 | ○ |
| Example 2 | | | 1000 | 0.15 | 0.01 | 74.3 | ○ |
| Example 3 | | | | 0.30 | 0.01 | 101.5 | ○ |

TABLE 1-continued

| Example | First Fluid | Second Fluid | Number of Revolutions [rpm] | Supply Pressure [MPaG] | Back Pressure [MPaG] | Average Particle Size [nm] | Redispersibility |
|---|---|---|---|---|---|---|---|
| Example 4 | | | 2000 | 0.30 | 0.01 | 64.1 | ○ |
| Comparative Example 1 | 4% Tween 80/2% aciclovir aqueous solution | | 20000 | — | — | 1340 | x |

The amount of energy required for forming aciclovir microparticles in Examples in the present invention, as compared with Comparative Example, was about 1/200 for Example 1, about 1/24 for Example 2 or 3, and about 1/3 for Example 4. From this result, it was found that the production method in Examples is superior in energy efficiency, although the production methods in Examples can produce finer particles than in Comparative Example.

The results are shown in Table 2.

TABLE 2

| | Example 1 | Example 2 | Example 3 | Example 4 | Comparative Example 1 |
|---|---|---|---|---|---|
| Number of revolutions [rpm] | 500 | 1000 | 1000 | 2000 | 21500 |
| Particle diameter $D_{50}$ [nm] | 88.6 | 74.3 | 101.5 | 64.1 | 1340 |
| Amount of energy applied [—] | 0.005 | 0.041 | 0.041 | 0.330 | 1 |

The invention claimed is:

1. A method for producing microparticles, the method comprising the steps of:

introducing a fluid to be processed between a first processing surface and a second processing surface arranged to be opposite to each other and which are able to approach to and separate from each other, at least one of which rotates relative to the other, the fluid to be processed comprising of at least two kinds of fluids;

generating a force to move in the direction of separating the second processing surface from the first processing surface by pressure of the fluid to be processed;

maintaining a distance between the first processing surface and the second processing surface in a minute space by the force;

forming a thin film fluid of the fluid to be processed that is passed between the first processing surface and the second processing surface maintained in a minute space;

cooling or heating the thin film fluid to change saturation solubility, thereby separating microparticles, wherein the first fluid processing surface and the second processing surface are circular and one side of the outside and the center of the first processing surface and the second processing surface is an upstream end and the other side is a downstream end, and at least one of the first processing surface and the second processing surface is formed with a groove-like depression extending from upstream to downstream, one kind of the at least two kinds of fluids is introduced into the space between the first processing surface and the second processing surface by micro-pump effect by rotation of the processing surface provided with the depression;

providing another introduction path independent of the flow path through which the one kind of the fluids is passed; and providing at least one opening leading to the introduction path and being arranged in at least either the first processing surface or the second processing surface, wherein the opening is positioned downstream at a point where a direction of flow of the one kind of the fluids is changed to a direction of flow of a laminar flow formed between the at least two processing surfaces, and another kind of the at least two kinds of fluids is introduced from the opening between the processing surfaces, whereby each of the above-mentioned fluids is mixed in the thin film fluid, at least either the one kind of the fluids or the another kind of the fluids is a fluid in which at least one kind of microparticle material is dissolved, and the one kind of the fluids and the another kind of the fluids are mixed under the control of the laminar flow in the thin film fluid, thereby separating the microparticles.

2. A method for producing microparticles, the method comprising the steps of:

introducing a fluid to be processed between a first processing surface and a second processing surface arranged to be opposite to each other and which are able to approach to and separate from each other, at least one of which rotates relative to the other;

generating a force to move in the direction of separating the second processing surface from the first processing surface by pressure of the fluid to be processed;

maintaining a distance between the first processing surface and the second processing surface in a minute space by the force;

forming a thin film fluid of the fluid to be processed that is passed between the first processing surface and the second processing surface maintained in a minute space;

providing, as the fluid to be processed, at least two fluids, wherein at least one kind of the fluids contains at least one kind of microparticle materials, and at least one kind of a fluid other than the above fluid has a temperature different from the fluid containing said microparticle material;

joining together the respective fluids in the thin film fluid;

separating microparticles in the thin film fluid by using the change of saturation solubility due to the temperature difference of the fluid containing the microparticle material, wherein the first fluid processing surface and the second processing surface are circular and one side of the outside and the center of the first processing surface and the second processing surface is an upstream end and the other side is a downstream end, and at least one of the first processing surface and the second processing surface is formed with a groove-like depression extending from upstream to downstream, one kind of the at least two kinds of fluids is introduced into the space between the first processing surface and the second processing surface by micro-pump effect by rotation of the processing surface provided with the depression;

providing another introduction path independent of the flow path through which the one kind of the fluids is passed; and providing at least one opening leading to the introduction path and being arranged in at least either the first processing surface or the second processing surface, wherein the opening is positioned downstream at a point where a direction of flow of the one kind of the fluids is changed to a direction of flow of a laminar flow formed between the at least two processing surfaces, and another kind of the at least two kinds of fluids is introduced from the opening between the processing surfaces, whereby each of the above-mentioned fluids is mixed in the thin film fluid, and the one kind of the fluids and the another kind of the fluids are mixed under the control of the laminar flow in the thin film fluid, thereby separating the microparticles.

3. The method for producing microparticles according to claim 1, further comprising the steps of:

providing a fluid pressure imparting mechanism for imparting pressure to a fluid to be processed;

providing at least two processing members of a first processing member and a second processing member, the second processing member being capable of approaching to and separating from the first processing member;

providing a rotation drive mechanism for rotating the first processing member and the second processing member relative to each other, wherein the first processing member comprises a first processing surface, and the second processing member comprises a second processing surface, the first and second processing surfaces positioned facing each other, wherein each of the processing surfaces constitutes part of a sealed flow path through which the fluid under the pressure is passed, wherein two or more fluids to be processed, at least one of which contains a microparticle material, are uniformly mixed and positively reacted between the processing surfaces, wherein, of the first and second processing members, at least the second processing member is provided with a pressure-receiving surface, and at least part of the pressure-receiving surface is comprised of the second processing surface, wherein the pressure-receiving surface receives pressure applied to the fluid to be processed by the fluid pressure imparting mechanism thereby generating a force to move in the direction of separating the second processing surface from the first processing surface, wherein the fluid under the pressure is passed between the first and second processing surfaces being capable of approaching to and separating from each other and rotating relative to each other, whereby the fluid to be processed forms a thin film fluid while passing between both the processing surfaces, wherein at least one fluid to be processed sent from the introduction path is introduced into between the processing surfaces, whereby the microparticle material contained in at least any one of the aforementioned fluids to be processed, and a fluid other than any one of said fluids to be processed enable a state of desired reaction by mixing under uniform stirring in the thin film fluid.

4. The method for producing microparticles according to claim 1, wherein at least one kind of the fluid to be processed contains a surfactant.

5. The method for producing microparticles according claim 1, wherein heat is added between the processing surfaces; ultraviolet ray (UV) is irradiated between the processing surfaces; or ultrasonic energy is supplied between the processing surfaces.

6. The method for producing microparticles according to claim 1, wherein the reaction for separating microparticles is conducted in a container capable of securing a depressurized or vacuum state, at least to form a depressurized or vacuum state of a secondary side at which the fluid to be processed after processing is discharged thereby removing a gas generated during the reaction and a gas contained in the fluid, or to removing a solvent of the fluid to be processed.

7. The method for producing microparticles according to claim 1, wherein the average primary particle size of the obtained microparticles is 0.5 nm to 10000 nm.

8. The method for producing microparticles according to claim 2, further comprising the steps of:

providing a fluid pressure imparting mechanism for imparting pressure to a fluid to be processed;

providing at least two processing members of a first processing member and a second processing member, the second processing member being capable of approaching to and separating from the first processing member;

providing a rotation drive mechanism for rotating the first processing member and the second processing member relative to each other, wherein the first processing member comprises a first processing surface, and the second processing member comprises a second processing surface, the first and second processing surfaces positioned facing each other, wherein each of the processing surfaces constitutes part of a sealed flow path through which the fluid under the pressure is passed, wherein two or more fluids to be processed, at least one of which contains a microparticle material, are uniformly mixed and positively reacted between the processing surfaces, wherein, of the first and second processing members, at least the second processing member is provided with a pressure-receiving surface, and at least part of the pressure-receiving surface is comprised of the second processing surface, wherein the pressure-receiving surface receives pressure applied to the fluid by the fluid pressure imparting mechanism thereby generating a force to move in the direction of separating the second processing surface from the first processing surface, wherein the fluid under the pressure is passed between the first and second processing surfaces being capable of approaching to and separating from each other and rotating relative to each other, whereby the processed fluid forms a thin film fluid while passing between both the processing surfaces, wherein at least one fluid to be present sent from the introduction path is introduced into between the processing surfaces, whereby the microparticle material contained in at least any one of the aforementioned fluids to be processed, and a fluid other than any one of said fluids to be processed enable a state of desired reaction by mixing under uniform stirring in the thin film fluid.

9. The method for producing microparticles according to claim 2, wherein at least one kind of the fluid to be processed contains a surfactant.

10. The method for producing microparticles according to claim 3, wherein at least one kind of the fluid to be processed contains a surfactant.

11. The method for producing microparticles according to claim 2, wherein heat is added between the processing surfaces; ultraviolet ray (UV) is irradiated between the processing surfaces; or ultrasonic energy is supplied between the processing surfaces.

12. The method for producing microparticles according to claim 3, wherein heat is added between the processing surfaces; ultraviolet ray (UV) is irradiated between the processing surfaces; or ultrasonic energy is supplied between the processing surfaces.

13. The method for producing microparticles according to claim 4, wherein heat is added between the processing surfaces; ultraviolet ray (UV) is irradiated between the processing surfaces; or ultrasonic energy is supplied between the processing surfaces.

14. The method for producing microparticles according to claim 2, wherein the reaction for separating microparticles is conducted in a container capable of securing a depressurized or vacuum state, at least to form a depressurized or vacuum state of a secondary side at which the fluid after processing is discharged thereby removing a gas generated during the reaction and a gas contained in the fluid, or to removing a solvent of the fluid.

15. The method for producing microparticles according to claim 3, wherein the reaction for separating microparticles is conducted in a container capable of securing a depressurized or vacuum state, at least to form a depressurized or vacuum state of a secondary side at which the fluid after processing is discharged thereby removing a gas generated during the reaction and a gas contained in the fluid, or to removing a solvent of the fluid.

16. The method for producing microparticles according to claim 4, wherein the reaction for separating microparticles is conducted in a container capable of securing a depressurized or vacuum state, at least to form a depressurized or vacuum state of a secondary side at which the fluid after processing is discharged thereby removing a gas generated during the reaction and a gas contained in the fluid, or to removing a solvent of the fluid.

17. The method for producing microparticles according to claim 5, wherein the reaction for separating microparticles is conducted in a container capable of securing a depressurized or vacuum state, at least to form a depressurized or vacuum state of a secondary side at which the fluid after processing is discharged thereby removing a gas generated during the reaction and a gas contained in the fluid, or to removing a solvent of the fluid.

18. The method for producing microparticles according to claim 1, further comprising the step of providing at least one temperature regulating mechanism to generate a temperature difference between the two processing surfaces, and the temperature difference is 5° C. to 100° C.

19. The method for producing microparticles according to claim 3, wherein the opening is positioned downstream at a point where a direction of flow of the fluid to be processed under the pressure is changed to a direction of flow of the spiral laminar flow formed between the at least two processing surfaces.

20. The method for producing microparticles according to claim 8, wherein the opening is positioned downstream at a point where a direction of flow of the fluid to be processed under the pressure is changed to a direction of flow of the spiral laminar flow formed between the at least two processing surfaces.

* * * * *